United States Patent [19]

Ries et al.

[11] Patent Number: 5,519,138

[45] Date of Patent: May 21, 1996

[54] PHENYLALKYL DERIVATIVES, WITH PHARMACEUTICAL ACTIVITY

[75] Inventors: Uwe Ries; Manfred Reiffen; Wolfgang Grell, all of Biberach; Norbert Hauel, Eberhardzell; Berthold Narr; Armin Heckel, both of Biberach; Andreas Bomhard, Duesseldorf; Jacques van Meel, Mittelbiberach; Wolfgang Wienen, Apfingen; Michael Entzeroth, Warthausen, all of Germany

[73] Assignee: Dr. Karl Thomae GmbH, Biberach an der Riss, Germany

[21] Appl. No.: 348,650

[22] Filed: Dec. 1, 1994

Related U.S. Application Data

[63] Continuation of Ser. No. 914,182, Jul. 15, 1992, abandoned.

[30] Foreign Application Priority Data

Jul. 15, 1991 [DE] Germany ............................ 41 23 341.7

[51] Int. Cl.⁶ .................... A61K 31/41; C07D 401/14; C07D 403/14; C07D 405/14; C07D 471/04; C07D 487/04

[52] U.S. Cl. .................... 544/287; 546/118; 546/119; 546/153; 548/304.4; 548/305.4; 548/305.7; 548/310.1; 548/113; 548/114; 548/253; 548/254; 548/252

[58] Field of Search ............... 548/304.4, 305.7, 548/305.4, 114, 253, 254, 319.1, 252, 113, 310.1; 546/118, 119, 153; 544/287; 514/259, 274, 317, 381, 394

[56] References Cited

U.S. PATENT DOCUMENTS

| | | | |
|---|---|---|---|
| 4,439,226 | 3/1984 | Pilgram | 548/304.4 X |
| 4,714,762 | 12/1987 | Hoefle et al. | 514/303 |
| 4,880,804 | 11/1989 | Carini et al. | 514/234.5 |
| 5,030,643 | 7/1991 | Bernstein et al. | 514/373 |
| 5,084,575 | 1/1992 | Kreft et al. | 546/172 |
| 5,116,860 | 5/1992 | Buerstinghaus et al. | 514/399 |
| 5,128,359 | 7/1992 | Bru-Magniez et al. | 514/394 |
| 5,171,748 | 12/1992 | Roberts et al. | 514/381 |
| 5,216,003 | 6/1993 | Vaquez | 514/381 |
| 5,314,880 | 5/1994 | Whittaker et al. | 514/80 |
| 5,389,634 | 2/1995 | Fortin et al. | 514/248 |

FOREIGN PATENT DOCUMENTS

| | | | |
|---|---|---|---|
| 0360098 | 3/1990 | European Pat. Off. | 548/304.4 |
| 0385850 | 9/1990 | European Pat. Off. | 548/305.4 |
| 4142366 | 6/1993 | Germany | 548/304.4 |

*Primary Examiner*—Floyd D. Higel
*Attorney, Agent, or Firm*—R. P. Raymond; M–E. M. Devlin; A. R. Stempel

[57] ABSTRACT

A phenylalkyl derivative of the formula

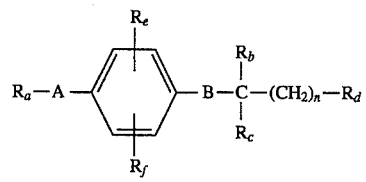

wherein $R_a$ to $R_f$, A and B are substituents and n is the number 0 or 1.

These phenylalkyl derivatives possess angiotensin antagonist activity.

6 Claims, No Drawings

PHENYLALKYL DERIVATIVES, WITH PHARMACEUTICAL ACTIVITY

This is a continuation of prior application Ser. No. 07/914,182, filed Jul. 15, 1992, and now abandoned.

The present invention relates to phenylalkyl derivatives of general formula

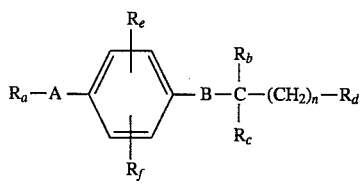
(I)

and the compound 5,7-dimethyl-2-ethyl-3-[4-[α-(1H-tetrazol-5-yl)benzyloxy] -3,5-dichlorobenzyl]imidazo-[4,5-b]pyridine, the isomer mixtures thereof, the tautomers, enantiomers and salts thereof, more particularly for pharmaceutical use the physiologically acceptable salts thereof with inorganic or organic acids or bases.

In the above general formula n represents the number 0 or 1,

A represents a straight-chained or branched alkylene group,

B represents an oxygen atom, a carbonyl, hydroxy-methylene, sulphenyl, sulphinyl or sulphonyl group, a straight-chained or branched alkylene group, a $C_{2-4}$-alkylidene group, a 1,1-cycloalkylene group or an imino group optionally substituted by an alkyl group or by a $C_{1-4}$-alkanoyl group, $R_a$ represents a chlorine or bromine atom, a hydroxy, alkylsulphonyloxy, phenylsulphonyloxy or phenylalkyl-sulphonyloxy group or a group of the formula

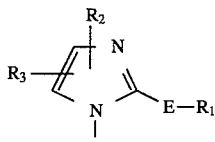

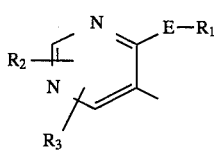

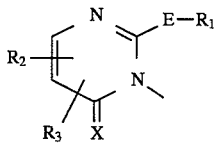

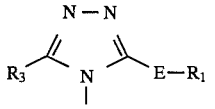

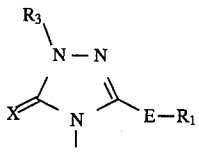

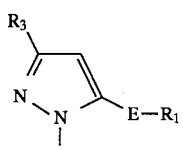

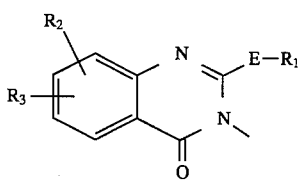

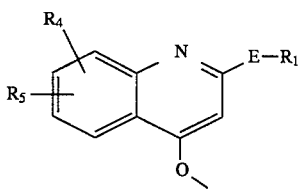

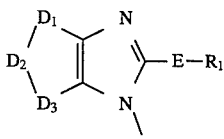

or

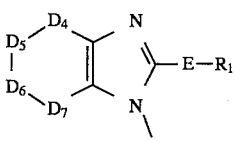

wherein one of the groups $D_1$, $D_2$ or $D_3$ represents a methylene or imino group and the remaining groups $D_1$ to $D_3$ are each methine groups, whilst additionally a methine group may be replaced by a nitrogen atom and one of the methine groups may be substituted by the group $R_5$ and, optionally, another of the methine groups may be substituted by the group R4, none, one or two of the groups $D_4$, $D_5$, $D_6$ or $D_7$ may represent a nitrogen atom and the remaining groups $D_4$, $D_5$, $D_6$ or $D_7$ may each represent methine groups, whilst additionally a methine group may be substituted by the group $R_4$ and another methine group may be substituted by the group $R_5$, E represents a carbon-carbon bond, an oxygen or sulphur atom, a hydroxymethylene or carbonyl group or an imino group optionally substituted by a $C_{1-6}$-alkyl group, by a cycloalkyl group, by a $C_{2-5}$-alkanoyl group or by an allyl, phenyl or benzyl group, X represents an oxygen or sulphur,atom or an imino group optionally substituted by an alkyl, phenyl or phenylalkyl group, $R_1$ represents a straight-chained or branched $C_{1-9}$-alkyl group, a straight-chained or branched $C_{2-6}$-alkenyl or $C_{2-6}$-alkynyl group, whilst the above-mentioned saturated and unsaturated alkyl moieties may each be substituted by a cycloalkyl group, by a fluorine, chlorine or bromine atom, by a hydroxy, amino, alkylamino, dialkylamino or α,α-difluoroethane group, or $R_1$ may represent a $C_{1-4}$-perfluoroalkyl group or a cycloalkyl group, which may be mono- or di-substituted by a trifluoromethyl group or by an alkyl group, $R_2$ represents a hydrogen, fluorine, chlorine or bromine atom, a $C_{1-5}$-alkyl or $C_{1-5}$-perfluoroalkyl group, a cyano or nitro group, $R_3$ represents a hydrogen atom, a cyano group, a $C_{1-6}$-alkyl group optionally substituted by a hydroxy or alkoxy group, a $C_{1-6}$-perfluoroalkyl group, a $C_{3-6}$-alkenyl group optionally substituted by fluorine atoms, a phenylalkyl or phenyl($C_{2-4}$)alkenyl group, a $C_{1-5}$-alkyl group which is terminally substituted by an imidazol-1-yl, triazolyl, tetrazolyl, phthalimido, $R_6COO$—, $R_7S$—, $R_7SO$—, $R_7SO_2$—, $R_7CO$—, $R_7NHCOO$—, $R_7NHCO$—, $R_7NHCONR_7$—, $R_8CONR_7$- or $R_8SO_2NR_7$- group, whilst the triazolyl group may additionally be mono- or di-substituted by an acetoxy or alkyl group and $R_6$ represents a $C_{1-8}$-alkyl or $C_{1-8}$-perfluoroalkyl group, a cycloalkyl, phenyl, benzyl, phenylethyl, adamantyl, naphthyl, naphthylmethyl or naphthylethyl group, $R_7$ represents a hydrogen atom or has the meanings given for $R_6$ hereinbefore, $R_8$ has the meanings given for $R_7$ hereinbefore or represents a piperazino group optionally substituted by an alkyl or phenyl group in the 4-position, or $R_8$ represents a pyrrolidino, piperidino, hexamethyleneimino, morpholino, $R_7O$- or $(R_7)_2N$-group, $R_4$ represents a hydrogen, fluorine, chlorine or bromine atom, a trifluoromethyl group, a cycloalkyl group, a $C_{1-6}$-alkyl group optionally substituted by a cycloalkyl, hydroxy, alkoxy, alkylamino, dialkylamino, alkoxycarbonyl, alkylaminocarbonyl or dialkylamino-carbonyl group, and $R_5$ represents a hydrogen, fluorine, chlorine or bromine atom, a straight-chained or branched $C_{1-6}$-alkyl or $C_{1-6}$-perfluoroalkyl group, a $C_{2-6}$-alkenyl or $C_{2-6}$-alkynyl group, whilst the above-mentioned alkyl and alkenyl moieties may each be mono- or disubstituted by a heteroaryl, hydroxy, alkoxy, amino, alkylamino, dialkylamino, alkylcarbonylamino, N-alkyl-alkylcarbonylamino, carboxy, alkoxycarbonyl, alkylcarbonyloxy, piperidinocarbonyl, morpholinocarbonyl, aminocarbonyl, alkylaminocarbonyl, dialkylaminocarbonyl, tetrazol-5-yl, tetrazol-5-yl-aminocarbonyl, alkylsulphenyl, alkylsulphinyl, alkylsulphonyl, aminosulphonyl, alkylaminosulphonyl, dialkylaminosulphonyl, alkylsulphonylaminocarbonyl, heteroarylaminosulphonyl or alkylcarbonylaminosulphonyl group, a $C_{1-7}$-alkoxy group which is substituted in the 2, 3-, 4-, 5-, 6- or 7-position by an imidazolyl, tetrazolyl, benzimidazolyl or tetrahydrobenzimidazolyl group, or a phenylalkoxy group optionally substituted in the alkoxy moiety by a 1H-tetrazol-5-yl or 1-triphenylmethyl-tetrazol-5-yl group, a carboxy group or a group which is metabolically converted into a carboxy group in vivo, a $C_{1-4}$-alkylsulphonyloxy group, a benzenesulphonyloxy or phenylalkylsulphonyloxy group, an acylamino group optionally substituted at the nitrogen atom by a $C_{1-6}$-alkyl group or by a phenyl, cycloalkyl, phenylalkyl, cycloalkylalkyl, bicyclohexyl or biphenyl group, wherein the acyl group is a $C_{1-7}$-alkanoyl group, an alkoxycarbonyl group with a total of 2 to 4 carbon atoms, a $C_{1-6}$-alkylsulphonyl group, a benzoyl, benzenesulphonyl, phenylalkanesulphonyl, naphthylenesulphonyl, cycloalkylcarbonyl, phenylalkanoyl or cycloalkylalkanoyl group, whilst the above-mentioned phenyl nuclei may each be mono- or di-substituted by a fluorine, chlorine or bromine atom or by a methyl or methoxy group and the substituents may be identical or different, a phthalimino, homophthalimino, 2-carboxyphenylcarbonyl-amino or 2-carboxyphenylmethylamino group, whilst a carbonyl group in a phthalimino group may be replaced by a methylene, alkyl-methylene or dialkyl-methylene group and a methylene group in a homophthalimino group may be substituted by one or two alkyl groups, wherein the phenyl nuclei in any of said groups may be additionally mono- or di-substituted by alkyl or alkoxy groups and may be additionally wholly or partially hydrogenated, in which the substituents may be identical or different, a 5-, 6- or 7-membered alkyleneimino or alkenyleneimino group optionally substituted by one or two alkyl groups or by a tetramethylene or pentamethylene group, wherein a methylene group of the alkyleneimino or alkenyleneimino group may be replaced by a carbonyl or sulphonyl group, a bicycloalkane-2,3-dicarboxylic acid imino or bicycloalkene-2,3-dicarboxylic acid imino group, wherein the bicycloalkane and bicycloalkene moieties each contain 9 or 10 carbon atoms, may be substituted by 1, 2 or 3 methyl groups and may have an endomethylene group replaced by an oxygen atom, a glutaric acid imino group, in which the n-propylene group may be perfluorinated, and may be substituted by one or two alkyl groups or by a tetramethylene or pentamethylene group, a maleic acid imido or succinimido group optionally mono- or di-substituted by an alkyl or phenyl group, wherein the substituents may be identical or different, a 5-membered heteroaromatic ring bound via a carbon atom or via an imino group, which contains an imino group, an oxygen or sulphur atom, or which contains an imino group and an oxygen, sulphur or nitrogen atom, or $R_5$ represents a 6-membered heteroaromatic ring bound via a carbon atom which contains 1 or 2 nitrogen atoms, whilst both the 5-membered and the 6-membered heteroaromatic rings are each attached, via two adjacent carbon atoms to an n-propylene, n-butylene or 1,3-butadienyl group or are each attached via an imino group and an adjacent carbon atom to an n-propylene, n-butylene or 1,3-butadienyl group and, in an anellated pyridine ring thus formed, a methine group may be replaced by a nitrogen atom and a vinylene group in the 3-, 4-position relative to the nitrogen atom of the pyridine ring formed may be replaced by a sulphur atom or, in an anellated phenyl ring thus formed, one or two methine groups may be replaced by N-atoms, whilst additionally the above-mentioned aromatic or heteroaromatic fused rings may be monosubstituted in the carbon structure by a fluorine, chlorine or bromine atom, by an alkyl, alkoxy, hydroxy, phenyl, nitro, amino, alkylamino, dialkylamino, alkanoylamino, cyano, carboxy, alkoxycarbonyl, aminocarbonyl, alkylaminocarbonyl, dialkylaminocarbonyl, trifluoromethyl, alkanoyl, aminosulphonyl, alkylamino-sulphonyl or dialkylaminosulphonyl group or may be disubstituted by fluorine or chlorine atoms or by methyl, methoxy or hydroxy groups, and any -NH- group present in an imidazole ring may be substituted by a $C_{1-6}$-alkyl group or by a cycloalkyl group, a pyrrolidine, piperidine or pyridine ring bound via a carbon atom, wherein a phenyl group may be fused onto the pyridine ring via two adjacent carbon atoms and a methylene group adjacent to the N-atom in a pyrrolidine or piperidine ring may be replaced by a carbonyl group, an imidazolidinedione group optionally substituted by an alkyl, phenylalkyl, tetramethylene, pentamethylene or hexamethylene group, a pyridazin-3-one or dihydro-pyridazin-3-one group which may be substituted in the 2-position by an optionally phenyl-substituted alkyl group, and in the carbon structure may additionally be substituted by 1 or 2 alkyl groups, or an $R_{11}$—$NR_{10}$—CO—$NR_9$ group, wherein $R_9$ represents a hydrogen atom, a $C_{1-8}$-alkyl group or a phenylalkyl group, $R_{10}$ represents a hydrogen atom, a $C_{1-8}$-alkyl group, a $C_{3-5}$-alkenyl group, a phenylalkyl group or a $C_{5-7}$-cycloalkyl group, $R_{11}$ represents a hydrogen atom or a $C_{1-6}$-alkyl group or one of the groups $R_9$, $R_{10}$ or $R_{11}$ may also represent a bicyclohexyl or biphenylyl group or $R_{10}$ and $R_{11}$ together with the nitrogen atom between them represent a straight-chained $C_{4-6}$-alkyleneimino group or a morpholino group or $R_9$ and $R_{11}$ together represent a $C_{2-4}$-alkylene group, $R_b$ represents a cyano, trifluoromethylcarbonylamino, trifluoromethylcarbonylaminomethyl, trifluoromethylsulphonylamino, trifluoromethylsulphonylaminomethyl, alkylsulphonylamino, alkylsulphonylaminomethyl, arylsulphonylamino, arylsulphonylaminomethyl, aralkylsulphonylamino, aralkylsulphonylaminomethyl, arylsulphonylaminocarbonyl, benzylsulphonylamino-carbonyl, sulpho, aminosulphonyl, alkylaminosulphonyl, aralkylaminosulphonyl, arylaminosulphonyl, alkylcarbonylaminosulphonyl, aralkylcarbonylamino-sulphonyl, arylcarbonylaminosulphonyl, sulphomethyl, aminosulphonylmethyl, alkylaminosulphonylmethyl, aralkylaminosulphonylaminomethyl, arylaminosulphonyl-methyl, alkylcarbonylaminosulphonylmethyl, aralkyl-carbonylaminosulphonylmethyl, arylcarbonylaminosulphonylmethyl, phosphino, O-alkyl-phosphino, O-aralkylphosphino, O-aryl-phosphino, phosphono, O-alkyl-phosphono, O-aralkyl-phosphono, O-aryl-phosphono, OO-dialkylphosphono, phosphono-methyl, O-alkyl-phosphono-methyl, O-aralkyl-phosphonomethyl, O-aryl-phosphono-methyl, OO-dialkylphosphono-methyl, phosphato, O-alkyl-phosphato, O-aralkyl-phosphato, O-arylphosphato or OO-dialkoxy-phosphoryl group, a 1H-tetrazolyl, 1H-tetrazolylalkyl, 1H-tetrazolylaminocarbonyl or triazolyl group optionally substituted by an alkyl, trifluoromethyl, phenylalkyl or triphenylmethyl group, or an ($C_{1-6}$alkyl)sulphonylaminocarbonyl or perfluoro-($C_{1-6}$alkyl)-sulphonylaminocarbonyl group, a carboxy group, a group which is metabolically converted into a carboxy group in vivo, or an aralkoxycarbonyl group, $R_c$ represents a hydrogen atom, an alkyl, aralkyl, aryl, carboxy or alkoxycarbonyl group, $R_d$ represents a straight-chained or branched $C_{1-10}$-alkyl chain, a straight-chained or branched $C_{2-10}$-alkenyl or $C_{2-10}$-alkynyl group, a cycloalkyl or cycloalkylalkyl group, a phenyl group optionally mono- or di-substituted by fluorine, chlorine or bromine atoms or by methyl or methoxy groups, or a biphenyl, naphthyl or heteroaryl group, $R_e$ and $R_f$ represent hydrogen atoms and if $R_5$ represents a phthalimino, homophthalimino, 2-carboxyphenylcarbonyl-amino or 2-carboxyphenylmethylamino group, wherein a carbonyl group in a phthalimino group may be replaced by a methylene, alkyl-methylene or dialkyl-methylene group and a methylene group in a homophthalimino group may be substituted by one or two alkyl groups, wherein the phenyl nuclei in any of said groups may be additionally mono- or disubstituted by alkyl or alkoxy groups and may be additionally wholly or partially hydrogenated, in which the substituents may be the same or different, a carboxy group or a group which is metabolically converted into a carboxy group in vivo, a 5-, 6- or 7-membered alkyleneimino or alkenyleneimino group optionally substituted by one or two alkyl groups or by a tetramethylene or pentamethylene group, wherein a methylene group of the alkyleneimino or alkenyleneimino group may be replaced by a carbonyl or sulphonyl group, a bicycloalkane-2,3-dicarboxylic acid imino or bicycloalkene-2,3-dicarboxylic acid imino group, wherein the bicycloalkane and bicycloalkene moieties may each contain 9 or 10 carbon atoms and may be substituted by 1, 2 or 3 methyl groups and an endomethylene group may be replaced by an oxygen atom, a glutaric acid imino group wherein the n-propylene group may be perfluorinated or substituted by one or two alkyl groups or by a tetramethylene or pentamethylene group, a maleic acid imido or succinimido group optionally mono- or disubstituted by an alkyl or phenyl group, in which the substituents may be identical or different, a 5-membered heteroaromatic ring bound via a carbon atom or via an imino group and containing an imino group, an oxygen or sulphur atom or containing an imino group and an oxygen, sulphur or nitrogen atom, or a 6-membered heteroaromatic ring bound via a carbon atom and containing 1 or 2 nitrogen atoms, wherein both the 5-membered and the 6-membered heteroaromatic rings are each attached, via two adjacent carbon atoms to an n-propylene, n-butylene or 1,3-butadienyl group, or are each attached via an imino group and an adjacent carbon atom to an n-propylene, n-butylene or 1,3-butadienyl group, and in the anellated pyridine ring thus formed, a methine group may be replaced by a nitrogen atom and a vinylene ring in the 3-, 4-position relative to the nitrogen atom of the pyridine ring formed may be replaced by a sulphur atom or, in an anellated phenyl ring thus formed, one or two methine groups may be replaced by N-atoms, whilst additionally the above-mentioned aromatic or heteroaromatic fused rings may be monosubstituted in the carbon skeleton by a fluorine, chlorine or bromine atom or by an alkyl, alkoxy, hydroxy, phenyl, nitro, amino, alkylamino, dialkylamino, alkanoylamino, cyano, carboxy, alkoxycarbonyl, aminocarbonyl, alkylaminocarbonyl, dialkylaminocarbonyl, trifluoromethyl, alkanoyl, aminosulphonyl, alkylaminosulphonyl or dialkylaminosulphonyl group or may be disubstituted by fluorine or chlorine atoms or by methyl, methoxy or hydroxy groups and any -NH- group present in an imidazole ring may be substituted by a $C_{1-6}$-alkyl group or by a cycloalkyl group, or a pyrrolidine, piperidine or pyridine ring bound via a carbon atom, in which a phenyl group may be condensed onto the pyridine ring via two adjacent carbon atoms and a methylene group adjacent to the N-atom in a pyrrolidine or piperidine ring may be replaced by a carbonyl group, an imidazolidinedione group optionally substituted by an alkyl, phenylalkyl, tetramethylene, pentamethylene or hexamethylene group, a pyridazin-3-one or dihydro-pyridazin-3-one group which may be substituted in the 2-position by an optionally phenyl-substituted alkyl group and may additionally be substituted in the carbon skeleton by 1 or 2 alkyl groups, or an $R_{11}$—$NR_{10}$—CO—$NR_9$ group, wherein $R_9$, $R_{10}$ and $R_{11}$ are defined as hereinbefore, then $R_e$ may also represent a hydrogen, fluorine, chlorine or bromine atom or an alkyl or alkoxy group and $R_f$ may also represent a fluorine, chlorine or bromine atom or an alkoxy group, especially those compounds wherein $R_a$ to $R_f$, A, B and n are as hereinbefore defined with the proviso that $D_4$ to $D_7$ represent methine groups with the additional provisos (a) to (j) or $D_7$ represents a nitrogen atom and the groups $D_4$, $D_5$ and $D_6$ represent methine groups with the additional provisos (a) to (g) and (k) to (m) or (a) to (g) and (n) to (p) or one of the groups $D_4$, $D_5$ or $D_6$ represents a nitrogen atom and the remaining groups of groups $D_4$ to $D_6$ and $D_7$ represent methine groups or two of the groups $D_4$ to $D_7$ represent nitrogen atoms and the remaining groups of groups $D_4$ to $D_7$ represent methine groups, with the additional provisos that either (a) n represents the number 1 or (b) E has the meanings given for E hereinbefore with the exception of the carbon-carbon bond or (c) A has the meanings given for A hereinbefore with the exception of the methylene group or (d) B has the meanings for B given hereinbefore with the exception of the oxygen atom or (e) $R_b$ has the meanings given for $R_b$ hereinbefore with the exception of the carboxyl group or (f) $R_c$ has the meanings given for $R_c$ hereinbefore with the exception of the hydrogen atom or (g) $R_d$ has the meanings given for $R_d$ hereinbefore with the exception of the phenyl group or (h) $R_1$ has the meanings given for $R_1$ hereinbefore with the exception of the n-butyl group or (i) $R_4$ has the meanings given for $R_4$ hereinbefore with the exception of the methyl group in position 7 or (j) $R_5$ has the meanings given for $R_5$ hereinbefore with the exception of the hydrogen atom or (k) $R_1$ has the meanings given for $R_1$ hereinbefore with the exception of the ethyl group or (l) $R_4$ has the meanings given for $R_4$ hereinbefore with the exception of the methyl group in position 7 or (m) $R_5$ has the meanings given for $R_5$ hereinbefore with the exception of the methyl group in position 5 or (n) $R_1$ has the meanings given for $R_1$ hereinbefore with the exception of the n-propyl group or (o) $R_4$ has the meanings given for $R_4$ hereinbefore with the exception of the hydrogen atom or (p) $R_5$ has the meanings given for $R_5$ hereinbefore with the exception of the hydrogen atom and the other groups have the meanings given hereinbefore, whilst additionally a methine group mentioned in the above definitions of groups $D_4$ to $D_7$ may be substituted by a group $R_4$ and a further methine group mentioned in the above definitions of groups $D_4$ to $D_7$ may be substituted by a group $R_5$, whilst, unless otherwise stated, the above-mentioned alkyl, alkylene or alkoxy moieties may each contain 1 to 4 carbon atoms and the cycloalkyl moieties may each contain 3 to 7 carbon atoms, and the term "an aryl group" refers to a phenyl group optionally mono- or di-substituted by a fluorine, chlorine or bromine atom or by a hydroxy, alkyl, alkoxy, phenylalkoxy, phenyl, nitro, amino, alkylamino, dialkylamino, alkanoylamino, cyano, carboxy, alkoxycarbonyl, aminocarbonyl, alkylaminocarbonyl, dialkylaminocarbonyl, trifluoromethyl, alkanoyl, aminosulphonyl, alkylaminosulphonyl or dialkylamino-sulphonyl group, wherein the alkyl moiety may contain 1 to 4 carbon atoms in each case, or to a naphthyl group, the term "a heteroaryl group" refers to a 5-membered heteroaromatic ring which contains an imino group, an oxygen or sulphur atom, or contains an imino group and an oxygen, sulphur or nitrogen atom, or contains an imino group and 2 or 3 nitrogen atoms, and a 6-membered heteroaromatic ring which contains 1, 2 or 3 nitrogen atoms, whilst the above-mentioned rings may additionally be mono- or di-substituted by a fluorine, chlorine or bromine atom or by an alkyl, alkoxy, hydroxy, phenyl, nitro, amino, alkylamino, dialkylamino, alkanoylamino, cyano, carboxy, alkoxycarbonyl, aminocarbonyl, alkylaminocarbonyl, dialkylaminocarbonyl, trifluoromethyl, alkanoyl, aminosulphonyl, alkylaminosulphonyl or dialkylamino-sulphonyl group, and the above-mentioned phrase "a group which is metabolically converted into a carboxy group in vivo" refers, for example, to the esters of formulae

—CO—OR',

—CO—O—(HCR")—O—CO—R''' and

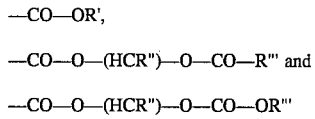

wherein

R' represents a straight-chained or branched $C_{1-6}$-alkyl group, a $C_{5-7}$-cycloalkyl group, a benzyl, 1-phenylethyl, 2-phenylethyl, 3-phenylpropyl, pivaloyloxymethyl, phthalidylmethyl, (1,3-dioxa-2-oxo-4-methyl-cyclopenten-5-yl)-methyl, methoxymethyl or cinnamyl group, R" represents a hydrogen atom or a methyl group and R''' represents a straight-chained or branched $C_{1-6}$-alkyl group, a $C_{5-7}$-cycloalkyl group, a phenyl, benzyl, 1-phenylethyl, 2-phenylethyl or 3-phenylpropyl group.

The new compounds of general formula I above wherein $R_a$ represents a chlorine or bromine atom, a hydroxy, alkylsulphonyloxy, phenylsulphonyloxy or phenylalkylsulphonyloxy group, are valuable intermediate products and the other compounds of general formula I above and the physiologically acceptable salts thereof have valuable pharmacological properties, being angiotensin-antagonists, especially angiotensin-II-antagonists.

The present invention thus relates to the new above-mentioned phenylalkyl derivatives, whilst the corresponding O-substituted phosphono or phosphato compounds and the corresponding cyano, alkoxycarbonyl or triphenylmethyl compounds are also valuable intermediate products.

The present invention thus also relates to new pharmaceutical compositions containing one of the above-mentioned pharmacologically active compounds of general formula I or a corresponding physiologically acceptable addition salt and are particularly suitable for treating hypertension and cardiac insufficiency, also for treating ischaemic peripheral circulatory disorders, myocardial ischaemia (angina), for preventing the progression of cardiac insufficiency after myocardial infarction, for treating diabetic nepthropathy, glaucoma, gastrointestinal disorders and diseases of the bladder.

Examples of the heteroaromatic groups mentioned hereinbefore in the definitions of groups $D_4$, $D_5$, $D_6$ and $D_7$ include the pyrido, pyrimido, pyrazino or pyridazino groups which may be substituted in the carbon skeleton by the groups $R_4$ and $R_5$.

Preferred compounds of general formula I above are, with the exception of (i) 2-n-butyl-1-[4-[(α-carboxy)benzyloxy]-benzyl]-benzimidazole, (ii) 2-n-propyl-7-methyl-3-[4-[(α-carboxy)benzyloxy]-benzyl]imidazo[4,5-b]pyridine and (iii) 5,7-dimethyl-2-ethyl-3-[4-[(α-carboxy)benzyloxy]-benzyl]imidazo[4,5-b]pyridine those wherein n represents the number 0 or 1, A represents a straight-chained or branched alkylene group B represents an oxygen atom, a straight-chained or branched $C_{1-3}$-alkylene group or an imino group optionally substituted by an alkyl group or by a $C_{1-4}$-alkanoyl group, $R_a$ represents a group of the formula

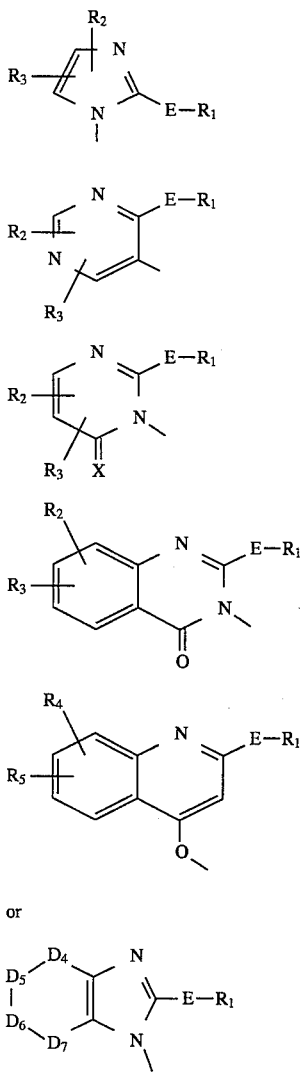

wherein none, one or two of the groups $D_4$, $D_5$, $D_6$ or $D_7$ represents a nitrogen atom and the remaining groups $D_4$, $D_5$, $D_6$ or $D_7$ each represent methine groups, whilst additionally a methine group may be substituted by the group $R_4$ and a further methine group may be substituted by the group $R_5$, E represents a carbon-carbon bond, an oxygen or sulphur atom or an imino group optionally substituted by a $C_{1-4}$-alkyl group, X represents an oxygen or sulphur atom, $R_1$ represents a straight-chained or branched $C_{1-6}$-alkyl group, a straight-chained or branched $C_{2-6}$-alkenyl or $C_{2-6}$-alkynyl group, whilst the above-mentioned saturated and unsaturated alkyl moieties may each be substituted by a fluorine, chlorine or bromine atom or by a hydroxy or amino group, or a $C_{3-6}$-cycloalkyl group, $R_2$ represents a hydrogen, fluorine, chlorine or bromine atom, a $C_{1-5}$-alkyl or $C_{1-5}$-perfluoroalkyl group or a cyano or nitro group, $R_3$ represents a hydrogen atom, a cyano group, a $C_{1-3}$-alkyl group optionally substituted by a hydroxy or alkoxy group, a $C_{1-3}$-perfluoroalkyl group, a $C_{3-6}$-alkenyl group optionally substituted by fluorine atoms, a $C_{1-3}$-alkyl group which is substituted in the terminal position by an $R_6COO-$, $R_7S-$, $R_7SO-$, $R_7SO_2-$, $R_7CO-$, $R_7NHCOO-$, $R_7NHCO-$, $R_7NHCONR_7-$, $R_8CONR_7-$ or $R_8SO_2NR_7$-group, wherein $R_6$ represents a $C_{1-4}$-alkyl or $C_{1-4}$-perfluoroalkyl group or a cycloalkyl, phenyl, benzyl or phenylethyl group, $R_7$ represents a hydrogen atom or has the meanings given for $R_6$ hereinbefore, $R_8$ has the meanings given for $R_7$ hereinbefore, $R_4$ represents a hydrogen, fluorine, chlorine or bromine atom, a trifluoromethyl group, a cycloalkyl group, a $C_{1-6}$-alkyl group optionally substituted by a hydroxy, alkoxy or alkoxycarbonyl group and $R_5$ represents a hydrogen, fluorine, chlorine or bromine atom, a straight-chained or branched $C_{1-6}$-alkyl or $C_{1-6}$-perfluoroalkyl group, a $C_{2-6}$-alkenyl or $C_{2-6}$-alkynyl group, whilst the above-mentioned alkyl and alkenyl moieties may each be mono- or di-substituted by a heteroaryl, hydroxy, alkoxy, amino, alkylamino, dialkylamino, alkylcarbonylamino, N-alkyl-alkylcarbonylamino, carboxy, alkoxycarbonyl, alkylcarbonyloxy, aminocarbonyl, alkylaminocarbonyl, dialkylaminocarbonyl or tetrazol-5-yl group, a $C_{1-5}$-alkoxy group or an α-(1H-tetrazol-5-yl)-benzyloxy group, a carboxy group or a group which is metabolically converted into a carboxy group in vivo, a $C_{1-4}$-alkylsulphonyloxy group or a benzenesulphonyloxy or phenylalkylsulphonyloxy group, an acylamino group optionally substituted at the nitrogen atom by a $C_{1-6}$-alkyl group or by a phenyl, cycloalkyl, phenylalkyl or cycloalkylalkyl group, in which the acyl group is a $C_{1-5}$-alkanoyl group, an alkoxycarbonyl group with a total of 2 to 4 carbon atoms, a $C_{1-6}$-alkylsulphonyl group, a benzoyl, benzenesulphonyl, cycloalkylcarbonyl, phenylalkanoyl or cycloalkylalkanoyl group, whilst the above-mentioned phenyl nuclei may each be mono- or di-substituted by a fluorine, chlorine or bromine atom or by a methyl or methoxy group and the substituents may be identical or different, a phthalimino or homophthalimino group, wherein a carbonyl group in a phthalimino group may be replaced by a methylene, alkyl-methylene or dialkyl-methylene group, and a methylene group in a homophthalimino group may be substituted by one or two alkyl groups, wherein the phenyl nuclei in any of said groups may be additionally mono- or disubstituted by alkyl or alkoxy groups and may be additionally wholly or partially hydrogenated, in which the substituents may be the same or different, a 5-, 6- or 7-membered alkyleneimino group optionally substituted by one or two alkyl groups or by a tetramethylene or pentamethylene group, wherein a methylene group of the alkyleneimino group may be replaced by a carbonyl or sulphonyl group, a maleic acid imido or succinimido group optionally mono- or disubstituted by an alkyl or phenyl group, wherein the substituents may be identical or different, a 5-membered heteroaromatic ring bound via a carbon atom or via an imino group, which contains an imino group, an oxygen or sulphur atom or which contains an imino group and an oxygen, sulphur or nitrogen atom, or a 6-membered heteroaromatic ring bound via a carbon atom which contains 1 or 2 nitrogen atoms, whilst both the 5-membered and the 6-membered heteroaromatic rings are each connected, via two adjacent carbon atoms to an n-propylene, n-butylene or 1,3-butadienyl group or are each attached via an imino group and an adjacent carbon atom to an n-propylene, n-butylene or 1,3-butadienyl group and, in an anellated pyridine ring thus formed, a methine group may be replaced by a nitrogen atom and a vinylene group in the 3-, 4-position relative to the nitrogen atom of the pyridine ring formed may be replaced by a sulphur atom or, in an anellated phenyl ring thus formed, one or two methine groups may be replaced by N-atoms, whilst additionally the above-mentioned aromatic or heteroaromatic fused rings may be monosubstituted in the carbon structure by a fluorine, chlorine or bromine atom or by an alkyl, alkoxy, hydroxy, phenyl, nitro, amino, alkylamino, dialkylamino, alkanoylamino, cyano, carboxy, alkoxycarbonyl, aminocarbonyl, alkylaminocarbonyl, dialkylaminocarbonyl, trifluoromethyl, alkanoyl, aminosulphonyl, alkylamino-sulphonyl or dialkylaminosulphonyl group or may be disubstituted by fluorine or chlorine atoms or by methyl, methoxy or hydroxy groups, and any -NH- group present in an imidazole ring may be substituted by a $C_{1-6}$-alkyl group, or an $R_{11}$—$NR_{10}$—CO—$NR_9$ group wherein $R_9$ represents a hydrogen atom, a $C_{1-6}$-alkyl group or a phenylalkyl group, $R_{10}$ represents a hydrogen atom, a $C_{1-6}$-alkyl group, a phenylalkyl group or a $C_{5-7}$-cycloalkyl group, $R_{11}$ represents a hydrogen atom or a $C_{1-6}$-alkyl group or $R_{10}$ and $R_{11}$ together with the nitrogen atom between them represent a straight-chained $C_{4-6}$-alkyleneimino group or a morpholino group or $R_9$ and $R_{11}$ together represent a $C_{2-4}$-alkylene group, $R_b$ represents a cyano, carboxy, arylsulphonylamino-carbonyl, benzylsulphonylaminocarbonyl, sulpho, alkylcarbonylaminosulphonyl, aralkylcarbonylamino-sulphonyl, arylcarbonylaminosulphonyl, alkylcarbonylaminosulphonylmethyl, aralkylcarbonylaminosulphonylmethyl, arylcarbonylaminosulphonylmethyl, phosphino, O-alkyl-phosphino, phosphono, O-alkyl-phosphono, OO-dialkylphosphono, phosphonomethyl, O-alkyl-phosphonomethyl, OO-dialkylphosphono-methyl, phosphato or O-alkyl-phosphato group, a 1-H-tetrazolyl or 1H-tetrazolyl-alkyl group optionally substituted by a phenylalkyl or triphenylmethyl group, an $(C_{14\ 6}$alkyl)sulphonylamino-carbonyl or perfluoro($C_{1-6}$alkyl)sulphonylaminocarbonyl, a group which is metabolically converted into a carboxy group in vivo, or an aralkoxycarbonyl group, $R_c$ represents a hydrogen atom, a methyl, phenyl, benzyl, carboxy or alkoxycarbonyl group and $R_d$ represents a straight-chained or branched $C_{1-6}$-alkyl group, a straight-chained or branched $C_{2-6}$-alkenyl or $C_{2-6}$alkynyl group, a cycloalkyl or cycloalkylalkyl group, a phenyl group optionally mono- or disubstituted by fluorine, chlorine or bromine atoms or by methyl or methoxy groups, or a biphenyl, naphthyl or heteroaryl group, $R_e$ and $R_f$ represent a hydrogen atom and, if $R_5$ represents a phthalimino or homophthalimino group, wherein a carbonyl group in a phthalimino group may be replaced by a methylene, alkylmethylene or dialkylmethylene group and a methylene group in a homophthalimino group may be substituted by one or two alkyl groups, wherein the phenyl nuclei in any of said groups may be additionally mono- or disubstituted by alkyl or alkoxy groups and may be additionally wholly or partially hydrogenated, in which the substituents may be the same or different, a carboxy group or a group which is metabolically converted into a carboxy group in vivo, a 5-, 6- or 7-membered alkyleneimino group optionally substituted by one or two alkyl groups or by a tetramethylene or pentamethylene group, wherein a methylene group of the alkyleneimino group may be replaced by a carbonyl or sulphonyl group, a maleic acid imido or succinimido group optionally mono- or di-substituted by an alkyl or phenyl group, the substituents being identical or different, a 5-membered heteroaromatic ring bound via a carbon atom or via an imino group, which contains an imino group, an oxygen or sulphur atom or which contains an imino group and an oxygen, sulphur or nitrogen atom, or a 6-membered heteroaromatic ring bound via a carbon atom which contains 1 or 2 nitrogen atoms, whilst both the 5-membered and the 6-membered heteroaromatic rings are each attached via two adjacent carbon atoms to an n-propylene, n-butylene or 1,3-butadienyl group or are each attached via an imino group and an adjacent carbon atom to an n-propylene, n-butylene or 1,3-butadienyl group and, in an anellated pyridine ring thus formed, a methine group may be replaced by a nitrogen atom and a vinylene group in the 3-, 4-position relative to the nitrogen atom of the pyridine ring formed may be replaced by a sulphur atom or, in an anellated phenyl ring thus formed, one or two methine groups may be replaced by N-atoms, whilst additionally the above-mentioned aromatic or heteroaromatic fused rings may be monosubstituted in the carbon structure by a fluorine, chlorine or bromine atom or by an alkyl, alkoxy, hydroxy, phenyl, nitro, amino, alkylamino, dialkylamino, alkanoylamino, cyano, carboxy, alkoxycarbonyl, aminocarbonyl, alkylaminocarbonyl, dialkylaminocarbonyl, trifluoromethyl, alkanoyl, aminosulphonyl, alkylamino-sulphonyl or dialkylaminosulphonyl group or may be disubstituted by fluorine or chlorine atoms or by methyl, methoxy or hydroxy groups, and any -NH- group present in an imidazole ring may be substituted by a $C_{1-6}$-alkyl group, or an $R_{11}$—$NR_{10}$—CO—$NR_9$ group wherein $R_9$ to $R_{11}$ are defined as hereinbefore, then $R_e$ may also represent a hydrogen, fluorine, chlorine or bromine atom or an alkyl or alkoxy group and $R_f$ may also represent a fluorine, chlorine or bromine atom or an alkoxy group, whilst unless otherwise specified the expression used hereinbefore "a group which is converted metabolically into a carboxy group in vivo" is defined as hereinbefore, the above-mentioned alkyl, alkylene or alkoxy moieties may each contain 1 to 4 carbon atoms and the cycloalkyl moieties may each contain 3 to 7 carbon atoms, and the expression "an aryl group" denotes a phenyl group optionally mono- or disubstituted by a fluorine, chlorine or bromine atom or by a hydroxy, alkyl, alkoxy, phenylalkoxy, phenyl or nitro group, wherein each alkyl moiety may contain from 1 to 4 carbon atoms, or a naphthyl group and "a heteroaryl group" denotes a 5-membered heteroaromatic ring which contains an imino group, an oxygen or sulphur atom or which contains an imino group and an oxygen, sulphur or nitrogen atom or which contains an imino group and 2 or 3 nitrogen atoms, and a 6-membered heteroaromatic ring which contains 1, 2 or 3 nitrogen atoms, whilst the above-mentioned rings may additionally be mono-or disubstituted by a fluorine, chlorine or bromine atom or by an alkyl, alkoxy, hydroxy, phenyl or nitro group, the isomer mixtures thereof, the tautomers, enantiomers and salts thereof.

Particularly preferred compounds of general formula I above are, with the exception of (i) 2-n-butyl-1-[4-[(α-carboxy)benzyloxy]benzyl]-benzimidazole, (ii) 2-n-propyl-7-methyl-3-[4-[(α-carboxy)benzyloxy]-benzyl]imidazo[4,5-b]pyridine and (iii) 5,7-dimethyl-2-ethyl-3-[4-[(α-carboxy)benzyloxy]-benzyl]imidazo[4,5-b]pyridine, those wherein n represents the number 0, A denotes a methylene, ethylene or ethylidene group, B denotes an oxygen atom, a methylene, imino, methylimino or acetylimino group, $R_a$ denotes a group of the formula

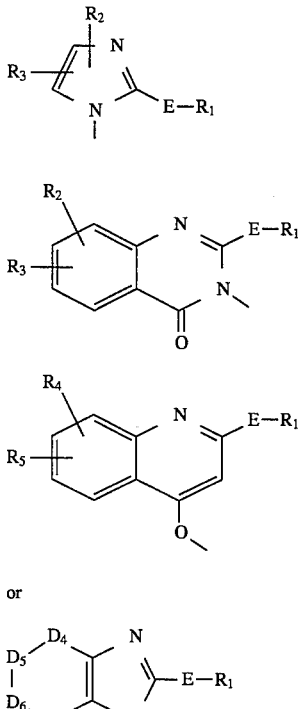

or wherein none, one or two of the groups $D_4$, $D_5$, $D_6$ or $D_7$ represents a nitrogen atom and the remaining groups $D_4$, $D_5$, $D_6$ or $D_7$ each represent methine groups, whilst additionally a methine group may be substituted by a group $R_4$ and another methine group may be substituted by a group $R_5$, E represents an oxygen atom or a carbon-carbon bond, $R_1$ represents a straight-chained or branched $C_{1-6}$-alkyl group, $R_2$ represents a hydrogen, fluorine, chlorine or bromine atom, $R_3$ represents a hydroxyalkyl group having 1 or 2 carbon atoms, $R_4$ represents a hydrogen atom or a $C_{1-3}$-alkyl group and $R_5$ represents a hydrogen, fluorine, chlorine or bromine atom, a straight-chained or branched $C_{1-3}$-alkyl group or an α-(1H-tetrazol-5-yl)-benzyloxy group, an amino or nitro group, a carboxy group or an alkoxycarbonyl group with a total of 2 to 4 carbon atoms, an acylamino group optionally substituted at the nitrogen atom by a $C_{1-5}$-alkyl group, wherein the acyl group is a $C_{1-5}$-alkanoyl group or a benzenesulphonyl group, the above-mentioned phenyl nucleus optionally being mono- or di-substituted by a methyl or methoxy group and the substituents being identical or different, a 5-, 6- or 7-membered alkyleneimino group optionally substituted by one or two methyl groups, wherein a methylene group of the alkyleneimino group may be replaced by a carbonyl or sulphonyl group, or a 2,3-dimethylsuccinimido, phthalimino, homophthalimino or isoindolin-1-on-yl group, a benzimidazol-2-yl group optionally substituted in the 1-position by a $C_{1-3}$-alkyl group or an $R_{11}$—$NR_{10}$—CO—$NR_9$ group wherein $R_9$ represents a hydrogen atom, a $C_{1-5}$-alkyl group or a phenylalkyl group having 1 to 3 carbon atoms in the alkyl moiety, $R_{10}$ represents a hydrogen atom, a $C_{1-5}$-alkyl group or a cyclohexyl group, $R_{11}$ represents a hydrogen atom, a benzyl group or a $C_{1-5}$-alkyl group or $R_9$ and $R_{11}$ together represent a $C_{2-3}$-alkylene group, $R_b$ represents a carboxy, 1H-tetrazolyl or O-alkylphosphono or alkylsulphonylaminocarbonyl group having 1 to 3 carbon atoms in the alkyl moiety, $R_c$ represents a hydrogen atom or a phenyl group, $R_d$ represents a straight-chained or branched $C_{1-4}$-alkyl group, a cyclohexyl, cyclohexylmethyl, phenyl, biphenyl, methoxyphenyl, chlorophenyl, pyridyl or naphthyl group, $R_e$ and $R_f$ represent hydrogen atoms and, if $R_5$ represents a benzimidazol-2-yl group optionally substituted in the 1-position by a $C_{1-3}$-alkyl group, a 2,3-dimethylsuccinimino group, a 5-, 6- or 7-membered alkyleneimino group optionally substituted by one or two methyl groups, wherein a methylene group may be replaced by a carbonyl or sulphonyl group, or an $R_{11}$—$NR_{10}$—CO—$NR_9$ group, wherein $R_9$ to $R_{11}$ are defined as hereinbefore, then $R_e$ may also represent a hydrogen, chlorine or bromine atom or a methoxy group and $R_f$ may also represent a chlorine or bromine atom or a methoxy group, the isomer mixtures thereof, the tautomers, enantiomers and salts thereof.

According to the invention, the compounds of general formula I are obtained by the following methods:

a) reacting a compound of general formula

wherein $R_a$ is as hereinbefore defined, with a compound of general formula

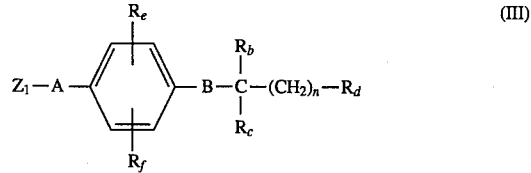

wherein A, B, n and $R_c$ to $R_f$ are as hereinbefore defined and $Z_1$ represents a nucleophilic leaving group such as a halogen atom, e.g. a chlorine, bromine or iodine atom, or a substituted sulphonyloxy group, e.g. a methanesulphonyloxy, phenylsulphonyloxy or p-toluene-sulphonyloxy group, followed by hydrolysis if required.

The reaction is conveniently carried out in a solvent or mixture of solvents such as methylene chloride, diethylether, tetrahydrofuran, dioxane, dimethylsulphoxide, dimethylformamide or benzene, optionally in the presence of an acid binding agent such as sodium carbonate, potassium carbonate, sodium hydroxide, potassium tert.-butoxide, triethylamine or pyridine, whilst the latter two may simultaneously also be used as solvent, preferably at temperatures between 0° and 100° C., e.g. at temperatures between ambient temperature and 50° C.

The subsequent hydrolysis is appropriately carried out either in the presence of an acid such as hydrochloric acid, sulphuric acid, phosphoric acid, trichloroacetic acid or trifluoroacetic acid or in the presence of a base such as sodium hydroxide or potassium hydroxide in a suitable solvent such as water, water/methanol, ethanol, water/ethanol, water/isopropanol or water/dioxane at temperatures between −10° C. and 120° C., e.g. at temperatures between ambient temperature and the boiling temperature of the reaction mixture.

In the reaction, a mixture of possible isomers is preferably obtained which may subsequently, if desired, be resolved into the corresponding isomers, preferably by chromatography, using a carrier such as silica gel or aluminium oxide.

b) Reacting a compound of general formula

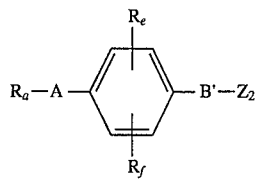
(IV)

wherein $R_a$, $R_e$, $R_f$ and A are defined as hereinbefore,

B' represents a straight-chained or branched $C_{1-4}$-alkylene group and $Z_2$ represents a nucleophilic leaving group such as a halogen atom, e.g. a chlorine, bromine or iodine atom, or a substituted sulphonyloxy group, e.g. a methanesulphonyloxy, phenylsulphonyloxy or p-toluenesulphonyloxy group, with a compound of general formula

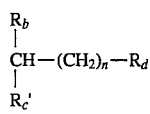
(V)

wherein $R_b$, $R_d$ and n are as hereinbefore defined and $R_c'$ represents an alkoxycarbonyl group, if necessary with subsequent hydrolysis and/or decarboxylation.

The reaction is conveniently carried out in a solvent or mixture of solvents such as methylene chloride, diethylether, tetrahydrofuran, dioxane, dimethylsulphoxide, dimethylformamide or benzene, optionally in the presence of an acid binding agent such as sodium carbonate, potassium carbonate, sodium hydroxide, potassium tert.-butoxide, triethylamine or pyridine, whilst the latter two may simultaneously also be used as solvent, preferably at temperatures between 0° and 100° C., e.g. at temperatures between ambient temperature and 50° C.

The subsequent hydrolysis is appropriately carried out either in the presence of an acid such as hydrochloric acid, sulphuric acid, phosphoric acid, trichloroacetic acid or trifluoroacetic acid or in the presence of a base such as sodium hydroxide or potassium hydroxide in a suitable solvent such as water, water/methanol, ethanol, water/ethanol, water/isopropanol or water/dioxane at temperatures between −10° C. and 120° C., e.g. at temperatures between ambient temperature and the boiling temperature of the reaction mixture.

The subsequent decarboxylation is conveniently carried out in the presence of an acid such as hydrochloric acid, sulphuric acid, phosphoric acid, acetic acid, trichloroacetic acid or trifluoroacetic acid in a suitable solvent such as water, water/methanol, ethanol, water/ethanol, water/isopropanol or water/dioxane at temperatures between 50° C. and 120° C., e.g. at temperatures between 60° C. and the boiling temperature of the reaction mixture.

c) In order to prepare compounds of general formula I wherein B represents an oxygen or sulphur atom or an optionally alkyl-substituted imino group:

Reacting a compound of general formula

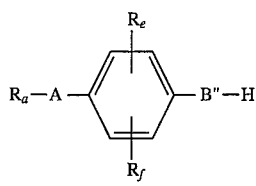
(VI)

wherein $R_a$, $R_e$, $R_f$ and A are as hereinbefore defined and B" represents an oxygen or sulphur atom or an optionally alkyl-substituted imino group, with a compound of general formula

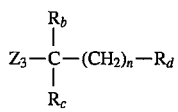
(VII)

wherein $R_b$ to $R_d$ and n are as hereinbefore defined and $Z_3$ represents a nucleophilic leaving group such as a halogen atom, e.g. a chlorine, bromine or iodine atom, or a substituted sulphonyloxy group, e.g. a methanesulphonyloxy, phenylsulphonyloxy or p-toluene-sulphonyloxy group, if necessary with subsequent hydrolysis.

The reaction is conveniently carried out in a solvent or mixture of solvents such as methylene chloride, diethylether, tetrahydrofuran, dioxane, dimethylsulphoxide, dimethylformamide or benzene, optionally in the presence of an acid binding agent such as sodium acetate, sodium carbonate, potassium carbonate, sodium hydroxide, potassium tert.-butoxide, triethylamine or pyridine, whilst the latter two may simultaneously also be used as solvent, preferably at temperatures between 0° and 100° C., e.g. at temperatures between ambient temperature and the boiling temperature of the reaction mixture.

The subsequent hydrolysis is appropriately carried out either in the presence of an acid such as hydrochloric acid, sulphuric acid, phosphoric acid, trichloroacetic acid or trifluoroacetic acid or in the presence of a base such as sodium hydroxide or potassium hydroxide in a suitable solvent such as water, water/methanol, ethanol, water/ethanol, water/isopropanol or water/dioxane at temperatures between −10° C. and 120° C., e.g. at temperatures between ambient temperature and the boiling temperature of the reaction mixture.

d) In order to prepare a compound of general formula I wherein $R_b$ represents a carboxy group:

Converting a compound of general formula

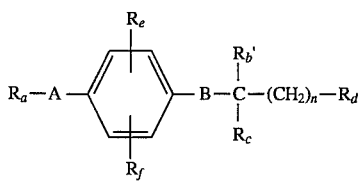
(VIII)

wherein $R_a$, $R_c$ to $R_f$, A, B and n are as hereinbefore defined and $R_b'$ represents a group which may be converted into a carboxy group by hydrolysis, thermolysis or hydrogenolysis.

For example, functional derivatives of the carboxy group such as the unsubstituted or substituted amides, esters, thiolesters, orthoesters, iminoethers, amidines or anhydrides, the nitrile group or the tetrazolyl group may be converted by hydrolysis into a carboxy group, esters with tertiary alcohols, e.g. the tert.butylester, may be converted by thermolysis into a carboxy group and esters with aralkanols, e.g. the benzylester, may be converted by hydrogenolysis into a carboxy group.

The hydrolysis is appropriately carried out either in the presence of an acid such as hydrochloric acid, sulphuric acid, phosphoric acid, trichloroacetic acid or trifluoroacetic acid or in the presence of a base such as sodium hydroxide or potassium hydroxide in a suitable solvent such as water, water/methanol, ethanol, water/ethanol, water/isopropanol or water/dioxane at temperatures between −10° C. and 120° C., e.g. at temperatures between ambient temperature and the boiling temperature of the reaction mixture. When hydrolysis is carried out in the presence of an organic acid such as trichloroacetic acid or trifluoroacetic acid, any alcoholic hydroxy groups present may simultaneously be converted into a corresponding acyloxy group such as the trifluoroacetoxy group.

If $R_b'$ in a compound of general formula VIII represents a cyano or aminocarbonyl group, these groups may also be converted into the carboxy group with a nitrite, e.g. sodium nitrite, in the presence of an acid such as sulphuric acid, which may simultaneously also be used as solvent, at temperatures between 0° and 50° C.

If $R_b'$ in a compound of general formula VIII represents for example the tert.-butyloxycarbonyl group, the tert.-butyl group may also be thermally cleaved, optionally in an inert solvent such as methylene chloride, chloroform, benzene, toluene, tetrahydrofuran or dioxane and preferably in the presence of a catalytic amount of an acid such as trifluoroacetic acid, p-toluenesulphonic acid, sulphuric acid, phosphoric acid or polyphosphoric acid, preferably at the boiling temperature of the solvent used, e.g. at temperatures between 40° C. and 100° C.

If $R_b'$ in a compound of general formula VIII represents the benzyloxycarbonyl group, for example, the benzyl group may also be hydrogenolytically cleaved in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between 0° and 50° C., e.g. at ambient temperature, under a hydrogen pressure of 1 to 5 bar. During hydrogenolysis, other groups may be reduced at the same time, e.g. a nitro group may be reduced to the amino group, a benzyloxy group to the hydroxy group, a vinylidene group to the corresponding alkylidene group or a cinnamic acid group to the corresponding phenylpropionic acid group, or they may be replaced by hydrogen atoms, e.g. a halogen may be replaced by a hydrogen atom.

e) In order to prepare a compound of general formula I wherein $R_b$ represents a 1H-tetrazolyl group:

Cleaving a protective group from a compound of general formula

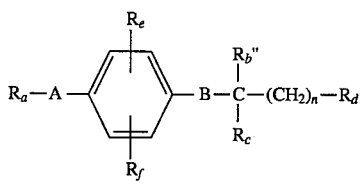

(IX)

wherein $R_a$, $R_c$ to $R_f$, A, B and n are as hereinbefore defined and $R_b''$ represents a 1H-tetrazolyl group protected in the 1- or 2-position by a protecting group.

Suitable protecting groups include, for example, the triphenylmethyl, tributyl tin or triphenyl tin groups.

The cleaving of a protecting group used is preferably carried out in the presence of a hydrohalic acid, preferably in the presence of hydrochloric acid, in the presence of a base such as sodium hydroxide or alcoholic ammonia in a suitable solvent such as methylene chloride, methanol, methanol/ammonia, ethanol or isopropanol at temperatures between 0° and 100° C., but preferably at ambient temperature or, if the reaction is carried out in the presence of alcoholic ammonia, at elevated temperatures, e.g. at temperatures between 100° and 150° C., preferably at temperatures between 120° and 140° C.

f) In order to prepare a compound of general formula I wherein $R_b$ represents a 1H-tetrazolyl group:

Reacting a compound of general formula

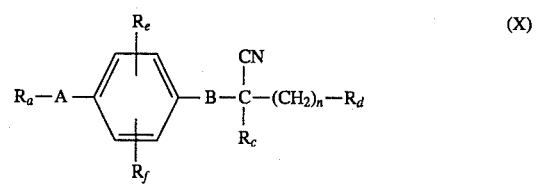

(X)

wherein $R_a$, $R_c$ to $R_f$, A, B and n are as hereinbefore defined, with hydrazoic acid or the salts thereof.

The reaction is preferably carried out in a solvent such as benzene, toluene or dimethylformamide at temperatures between 80° and 150° C., preferably at 125° C. Appropriately, either the hydrazoic acid is liberated during the reaction from an alkali metal azide, e.g. sodium azide, in the presence of a weak acid such as ammonium chloride or the tetrazolide salt obtained in the reaction mixture during the reaction with a salt of hydrazoic acid, preferably with aluminium azide or tributyl tin azide, which is also preferably produced in the reaction mixture by reacting aluminium chloride or tributyl tin chloride with an alkali metal azide such as sodium azide, is subsequently liberated by acidification with a dilute acid such as 2N hydrochloric or 2N sulphuric acid.

g) In order to prepare compounds of general formula I wherein $R_a$ represents a group of the formula

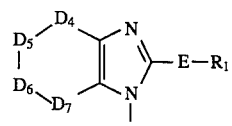

cyclising a compound of general formula

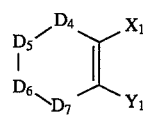

(XI)

wherein $D_1$ to $D_7$ are as hereinbefore defined, one of the groups $X_1$ or $Y_1$ represents a group of general formula

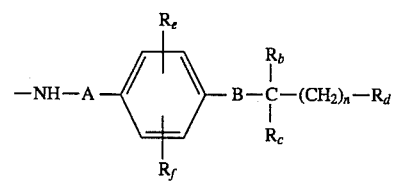

and the other group $X_1$ or $Y_1$ represents a group of general formula

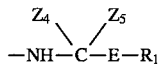

wherein $R_1$, A, B, E, n and $R_b$ to $R_f$ are as hereinbefore defined, $Z_4$ and $Z_5$, which may be identical or different, represent optionally substituted amino groups or hydroxy or mercapto groups optionally substituted by lower alkyl groups or $Z_4$ and $Z_5$ together represent an oxygen or sulphur atom, an imino group optionally substituted by a $C_{1-3}$-alkyl group, or an alkylenedioxy or alkylenedithio group each having 2 or 3 carbon atoms.

The cyclisation is conveniently carried out in a solvent or mixture of solvents such as ethanol, isopropanol, glacial acetic acid, benzene, chlorobenzene, toluene, xylene, glycol, glycol-monomethylether, diethyleneglycoldimethylether, sulpholane, dimethylformamide, tetraline or in an excess of the acylating agent used to prepare the compound of general formula XI, e.g. in the corresponding nitrile, anhydride, acid halide, ester or amide, e.g. at temperatures between 0° and 250° C., but preferably at the boiling temperature of the reaction mixture, optionally in the presence of a condensing agent such as phosphorusoxychloride, thionylchloride, sulphurylchloride, sulphuric acid, p-toluenesulphonic acid, methanesulphonic acid, hydrochloric acid, phosphoric acid, polyphosphoric acid, acetic anhydride or optionally in the presence of a base such as potassium ethoxide or potassium tert.-butoxide. However, cyclisation may also be carried out without a solvent and/or condensing agent.

However, it is particularly advantageous to carry out the reaction by preparing a compound of general formula XI in the reaction mixture by reducing a corresponding o-nitroamino compound, optionally in the presence of a carboxylic acid of general formula $R_a$—E—COOH, or by acylation of a corresponding o-diamino compound. When the reduction of the nitro group is broken off at the hydroxylamine stage, the N-oxide of a compound of general formula I is obtained in the subsequent cyclisation. The resulting N-oxide is then converted by reduction into a corresponding compound of general formula I.

The subsequent reduction of the N-oxide of formula I obtained is preferably carried out in a solvent such as water, water/ethanol, methanol, glacial acetic acid, ethyl acetate or dimethylformamide with hydrogen in the presence of a hydrogenation catalyst such as Raney nickel, platinum or palladium/charcoal, with metals such as iron, tin or zinc in the presence of an acid such as acetic acid, hydrochloric acid or sulphuric acid, with salts such as iron(II)sulphate, tin(II)chloride or sodium dithionite, or with hydrazine in the presence of Raney nickel at temperatures between 0° and 50° C., but preferably at ambient temperature.

h) In order to prepare compounds of general formula I wherein $R_5$ represents an $R_{11}$—$NR_{10}$—CO—$NR_9$ group:

Reacting a compound of formula

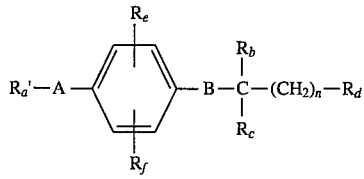
(XII)

wherein $R_b$ to $R_f$, A, B and n are as hereinbefore defined and $R_a'$ represents one of the groups mentioned for $R_a$ hereinbefore wherein $R_5$ is an amino group, a $C_{1-8}$-alkylamino group or a phenyl($C_{1-4}$alkyl)amino group, with a compound of formula

(XIII)

wherein $R_{10}$ represents a hydrogen atom, a $C_{1-8}$-alkyl group, a $C_{3-5}$-alkenyl group, a phenylalkyl group or a $C_{5-7}$-cycloalkyl group, $R_{11}$ represents a hydrogen atom or a $C_{1-6}$-alkyl group or one of the groups $R_{10}$ or $R_{11}$ also represents a bicyclohexyl or biphenylyl group or $R_{10}$ and $R_{11}$ together with the nitrogen atom between them represent a straight-chained $C_{4-6}$-alkyleneimino group or a morpholino group and $Z_6$ represents a nucleophilic leaving group such as a chlorine or bromine atom or, if one of the groups $R_{10}$ or $R_{11}$ represents a hydrogen atom, $Z_6$ together with $R_{10}$ or $R_{11}$ represents a nitrogen-carbon bond.

The reaction is preferably carried out in a solvent such as tetrahydrofuran, dioxane, ethylene chloride or benzene, optionally in the presence of an acid-binding agent such as triethylamine or pyridine, expediently at temperatures between 0° and 100° C., preferably at temperatures between 20° and 80° C.

i) In order to prepare compounds of general formula I wherein $R_5$ represents an acylamino group optionally substituted at the nitrogen atom by a $C_{1-6}$-alkyl group or by a phenyl, cycloalkyl, phenylalkyl, cycloalkylalkyl, bicyclohexyl or biphenyl group, wherein the acyl group is a $C_{1-7}$-alkanoyl group, a $C_{2-4}$-(alkoxycarbonyl) group, a $C_{1-6}$-alkylsulphonyl group, a benzoyl, benzenesulphonyl, phenylalkanesulphonyl, naphthalenesulphonyl, cycloalkylcarbonyl, phenylalkanoyl or cycloalkylalkanoyl group, whilst the above-mentioned phenyl nuclei may each be mono- or di-substituted by a fluorine, chlorine or bromine atom, by a methyl or methoxy group and the substituents may be identical or different, a phthalimino or homophthalimino group wherein the phenyl nucleus in each case may be mono- or di-substituted by $C_{1-3}$-alkyl or $C_{1-3}$-alkoxy groups, or a maleic acid imido or succinimido group optionally mono- or di-substituted by an alkyl or phenyl group, wherein the substituents may be identical or different:

Acylating a compound of formula

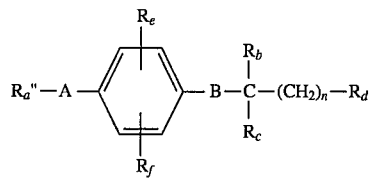
(XIV)

wherein $R_b$ to $R_f$, A, B and n are as hereinbefore defined and $R_a''$ represents one of the groups mentioned as a definition for $R_a$ hereinbefore, wherein $R_5$ represents an amino group optionally substituted by a $C_{1-6}$-alkyl group or by a phenyl, cycloalkyl, phenylalkyl, cycloalkyalkyl, bicyclohexyl or biphenyl group, with a compound of formula HO—U—$R_{12}$ 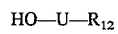 (XV)

wherein

U represents a carbonyl or sulphonyl group and $R_{12}$ represents a $C_{1-6}$-alkyl group, a $C_{1-3}$-alkoxy group, a phenyl, phenylalkyl, naphthyl or cycloalkyl group, wherein the above-mentioned phenyl nuclei may each be mono- or disubstituted by a fluorine, chlorine or bromine atom or by a methyl or methoxy group and the substituents may be identical or different, or, if U represents a carbonyl group, $R_{12}$ may also represent a hydrogen atom, a phenyl group which is substituted in the o-position by a carboxy or carboxymethyl group and wherein the phenyl nucleus may be mono- or di-substituted by $C_{1-3}$-alkyl or $C_{1-3}$-alkoxy groups and may additionally be wholly or partially hydrogenated, a 2-carboxy-ethyl or 2-carboxy-ethenyl group in which the ethyl and ethenyl moiety may each be mono- or di-substituted by an alkyl or phenyl group, or with a reactive derivative thereof such as an acid halide, acid ester or acid anhydride thereof.

Examples of reactive derivatives of a compound of formula XV include the esters thereof such as the methyl, ethyl or benzylester, the thioesters thereof such as the methylthio or ethylthioester, the halides thereof such as the acid chloride and the anhydrides or imidazolides thereof.

The reaction is conveniently carried out in a solvent or mixture of solvents such as water, methylene chloride, chloroform, ether, tetrahydrofuran, dioxane or dimethylformamide with a corresponding carboxylic acid in the presence of an acid activating or dehydrating agent such as thionylchloride, with the anhydrides thereof such as acetic acid anhydride, with the esters thereof such as ethyl acetate, with the halides thereof such as acetylchloride or methanesulphonyl chloride, optionally in the presence of an inorganic or tertiary organic base such as sodium hydroxide, potassium carbonate, triethylamine or pyridine, whilst the latter two may simultaneously also be used as solvent, at temperatures between −25° and 100° C., but preferably at temperatures between −10° and 80° C.

j) In order to prepare compounds of general formula I wherein $R_b$ represents a phosphono or O-alkyl-phosphono group:

Hydrolysis of a compound of general formula

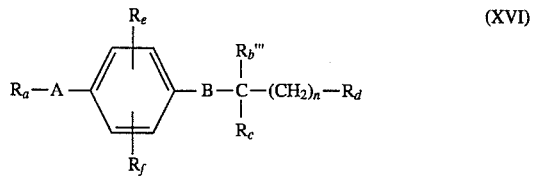

(XVI)

wherein

A, B, $R_a$, $R_c$ to $R_f$ and n are defined as hereinbefore and $R_b'''$ represents an O-alkyl- or OO-dialkyl-phosphono group in which each alkyl moiety may contain 1 to 5 carbon atoms.

The reaction is preferably carried out in a solvent such as methanol, methanol/water, ethanol or isopropanol in order to prepare a corresponding O-alkylphosphono compound of general formula I in the presence of a base such as potassium hydroxide or potassium methoxide or in order to prepare a corresponding phosphono compound of general formula I in the presence of an acid such as hydrobromic acid at the boiling temperature of the reaction mixture.

It is particularly advantageous to prepare a phosphono compound of general formula I by reacting a corresponding O-alkyl or OO-dialkyl compound of general formula XVI with bromine/trimethylchlorosilane in acetonitrile with subsequent hydrolysis using water at ambient temperature.

If according to the invention a compound of general formula I is obtained wherein $R_2$ or $R_5$ represents a nitro group, this may be converted by reduction into a corresponding compound of general formula I wherein $R_2$ or $R_5$ represents an amino group, or if according to the invention a compound of general formula I is obtained wherein B represents an imino group, this may be converted by alkanoylation into a corresponding compound of general formula I wherein B represents an imino group substituted by a $C_{1-4}$-alkanoyl group, or if according to the invention a compound of general formula I is obtained wherein B represents an imino group, this may be converted by alkylation into a corresponding compound of general formula I wherein B represents an imino group substituted by a $C_{1-3}$-alkyl group, or if according to the invention a compound of general formula I is obtained wherein $R_b$ or $R_b$ and $R_5$ each represent a carboxy group, this may be converted by esterification into a corresponding compound of general formula I wherein $R_b$ or $R_b$ and $R_5$ represent a group which is metabolically converted in vivo into a carboxy group, or if according to the invention a compound of general formula I is obtained wherein $R_b$ represents a carboxy group, this may, after conversion into a corresponding acid halide, be converted by reaction with a corresponding sulphonamide into a compound of general formula I wherein $R_b$ represents an alkanesulphonylaminocarbonyl, perfluoroalkanesulphonylaminocarbonyl, arylsulphonylaminocarbonyl or benzylsulphonylaminocarbonyl group.

The subsequent reduction of the nitro group is preferably carried out in a solvent such as water, water/ethanol, methanol, glacial acetic acid, ethyl acetate or dimethylformamide, suitably with hydrogen in the presence of a hydrogenation catalyst such as Raney nickel, platinum or palladium/charcoal, with metals such as iron, tin or zinc in the presence of an acid, with salts such as iron(II)sulphate, tin(II)chloride, sodium sulphide, sodium hydrogen sulphite or sodium dithionite, or with hydrazine in the presence of Raney nickel at temperatures between 0° and 80° C., but preferably at temperatures between 20° and 40° C.

The subsequent alkanoylation is suitably carried out in a solvent or mixture of solvents such as water, methylene chloride, chloroform, ether, tetrahydrofuran, dioxane or dimethylformamide with a corresponding carboxylic acid in the presence of an acid-activating or dehydrating agent such as thionylchloride, with the anhydrides thereof such as acetic anhydride, with the esters thereof such as ethyl acetate, with the halides thereof such as acetylchloride, optionally in the presence of an inorganic or tertiary organic base, such as sodium hydroxide, potassium carbonate, triethylamine or pyridine, whilst the latter two may simultaneously also be used as solvent, at temperatures between −25° and 100° C., but preferably at temperatures between −10° and 80° C.

The subsequent alkylation is suitably carried out in a solvent or mixture of solvents such as methylene chloride, diethylether, tetrahydrofuran, dioxane, dimethylsulphoxide, dimethylformamide or benzene, optionally in the presence of an acid binding agent such as sodium carbonate, potassium carbonate, sodium hydroxide, potassium tert.butoxide, triethylamine or pyridine, whilst the latter two may simultaneously also be used as solvent, with an alkylating agent such as methyliodide, ethyliodide, isopropylbromide, dimethyl-sulphate, diethylsulphate or methyl p-toluenesulphonate, preferably at temperatures between 0° and 100° C., e.g. at temperatures between ambient temperature and 50° C.

The conversion of a carboxyl group into a group which is metabolically converted in vivo into a carboxy group, is conveniently carried out by esterification with a corresponding alcohol or with a corresponding reactive acyl derivative, suitably in a solvent or mixture of solvents such as water, methylene chloride, chloroform, ether, tetrahydrofuran, dioxane or dimethylformamide or in an excess of the acylating agent as solvent, optionally in the presence of an acid-activating or dehydrating agent such as thionylchloride, with the anhydrides, esters or halides thereof, optionally in the presence of an inorganic or tertiary organic base, such as sodium hydroxide, potassium carbonate, triethylamine or pyridine, whilst the latter two may simultaneously also be used as solvent, at temperatures between −25° and 100° C., but preferably at temperatures between −10° and 80° C.

The subsequent reaction of an acid halide with a corresponding sulphonamide is suitably carried out in a solvent such as acetone, tetrahydrofuran or dioxane in the presence of a base such as triethylamine at temperatures between 0° and 50° C., preferably at temperatures between 10° and 30° C.

In the reactions described hereinbefore, any reactive groups present such as hydroxy, amino or alkylamino groups may optionally be protected during the reaction by conventional protecting groups which are split off again after the reaction.

Examples of protecting groups for a hydroxy group are the trimethylsilyl, acetyl, benzoyl, methyl, ethyl, tert.-butyl, benzyl or tetrahydropyranyl groups and protecting groups for an amino, alkylamino or imino group include the acetyl, benzoyl, ethoxycarbonyl and benzyl groups.

The optional subsequent cleaving of a protecting group is preferably carried out by hydrolysis in an aqueous solvent, e.g. in water, isopropanol/water, tetrahydrofuran/water or dioxane/water, in the presence of an acid such as hydrochloric acid or sulphuric acid or in the presence of an alkali metal base such as sodium hydroxide or potassium hydroxide at temperatures between 0° and 100° C., preferably at the boiling temperature of the reaction mixture. However, a benzyl group is preferably split off by hydrogenolysis, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures between 0° and 50° C., but preferably at ambient temperature, under a hydrogen pressure of 1 to 7 bar, preferably of 3 to 5 bar.

An isomer mixture of a compound of general formula I thus obtained may if desired be resolved by chromatography using a substrate such as silica gel or aluminium oxide.

Moreover, the compounds of general formula I obtained may be converted into the acid addition salts thereof, more particularly for pharmaceutical use the physiologically acceptable salts thereof with inorganic or organic acids. Suitable acids for this purpose include hydrochloric acid, hydrobromic acid, sulphuric acid, phosphoric acid, fumaric acid, succinic acid, lactic acid, citric acid, tartaric acid or maleic acid.

Furthermore, the new compounds of general formula I thus obtained, if they contain a carboxy or 1H-tetrazolyl group, may if desired subsequently be converted into the addition salts thereof with inorganic or organic bases, more particularly for pharmaceutical use into the physiologically acceptable addition salts thereof. Suitable bases include for example sodium hydroxide, potassium hydroxide, cyclohexylamine, ethanolamine, diethanolamine and triethanolamine.

The compounds of general formulae II to XVI used as starting materials are known from the literature in some cases or may be obtained by methods known from the literature.

Thus, for example, substituted pyrimidines of general formula II are described in Ep-A-0424317, substituted pyrimidinones are described in Ep-A-0407342 and Ep-A-0419048, substituted triazoles are described in Ep-A-0409332, substituted triazolinones, triazolthiones and triazolimines are described in Ep-A-0412594, substituted pyrazoles in Ep-A-0411507, substituted quinazolinones in Ep-A-0411766, substituted quinolines in Ep-A-0412848, 5-membered condensed imidazo derivatives in Ep-A-0407102, benzimidazoles in Ep-A-0392317, imidazopyridines and purines in Ep-A-0400974 and Ep-A-0399731 and substituted imidazoles in Ep-A-0253310.

The compounds of general formulae III and IV used as starting materials are obtained by reacting a corresponding alcohol with hydrohalic acid, with tetrabromomethane/triphenylphosphine or with a corresponding sulphonic acid halide.

The compounds of general formulae VIII, IX, X, XII, XIV and XVI used as starting materials are obtained by alkylating a corresponding compound with a compound analogous to a compound of general formula III.

The new compounds of general formula I and the physiologically acceptable addition salts thereof have valuable pharmacological properties. They are angiotensin antagonists, particularly angiotensin-II-antagonists.

For example, the compounds

A=2-n-propyl-4-methyl-1-[4-[(α-carboxy)benzyloxy]-benzyl]benzimidazole,

B=2-n-butyl-1-[4-[(α-carboxy)benzyloxy]benzyl]-6-dimethylaminocarbonylamino-benzimidazole, C=2-n-propyl-6-(1-methyl-benzimidazol-2-yl)-4-methyl-1-[4-[(α-carboxy)benzyloxy] benzyl]benzimidazole, D=2-methyl-4-[4'-[(α-carboxy)benzyloxy]benzyloxy]-quinoline, E=2-n-butyl-8-methyl-3-[4-[(α-carboxy)benzyloxy]-benzyl]quinazolin-4-one-semihydrate, F=2-n-propyl-4-methyl-6-(1-methyl-benzimidazol-2-yl)-1-[4-[α-(1H-tetrazol-5 -yl)benzyloxy]benzyl]-benzimidazole, G=2-n-butyl-6-(N-propionyl-methylamino)-1-[4-[(1-carboxy-3-methyl) butyloxy]benzyl]benzimidazole, H=2-n-butyl-5-methyl-6-(3-benzyl-3,4,5,6-tetrahydro-2(1H)-pyrimidinon-1 -yl)-3-[4-[α-(1H-tetrazol-5-yl)benzyloxy] benzyl]imidazol[4,5-b]pyridine and I=2-n-butyl-1-[4-[[α-[α-ethyl-phosphono]benzylamino] benzyl]benzimidazole were investigated for their biological effects as follows:
Description of method: Angiotensin II-receptor bonding The tissue (rats lung) is homogenised in Tris-buffer (50 mMol Tris, 150 mMol NaCl, 5 mMol EDTA, pH 7.40) and centrifuged twice for 20 minutes at 20,000x g. The finished pellets are resuspended in incubating buffer (50 mMol Tris, 5 mMol MgCl$_2$, 0.2% BSA, pH 7.40) 1:75, based on the moist weight of the tissue. Each 0.1 ml of homogenate is incubated for 60 minutes at 37° C. with 50 pM [$^{125}$I]-angiotensin II (NEN, Dreieich, FRG) with increasing concentrations of the test substance in a total volume of 0.25 ml.

Incubation is ended by rapid filtration through glass fibre filter mats. The filters are each washed with 4 ml of ice cold buffer (25 mMol Tris, 2.5 mMol $MgCl_2$, 0.1% BSA, pH 7.40). The bound radioactivity is measured using a gamma-counter. The corresponding $IC_{50}$ value is obtained from the dose-activity curve.

In the test described, substances A to I show the following $IC_{50}$ values:

| Substance | $IC_{50}$ [nM] |
|---|---|
| A | 76 |
| B | 8 |
| C | 4 |
| D | 2000 |
| E | 2000 |
| F | 12 |
| G | 830 |
| H | 27 |
| I | 560 |

Moreover, when the above-mentioned compounds were administered in a dose of 30 mg/kg i.v. no toxic side effects, e.g. negative inotropic effects or disorders in heart rhythm, were observed. The compounds are therefore well tolerated.

In view of their pharmacological properties, the new compounds and the physiologically acceptable addition salts thereof are suitable for the treatment of hypertension and cardiac insufficiency and also for treating ischaemic peripheral circulatory disorders, myocardial ischaemia (angina), for the prevention of the progression of cardiac insufficiency after myocardial infarction and for treating diabetic nephropathy, glaucoma, gastrointestinal diseases and bladder diseases.

The new compounds and the physiologically acceptable addition salts thereof are also suitable for treating pulmonary diseases, e.g. lung oedema and chronic bronchitis, for preventing arterial re-stenosis after angioplasty, for preventing thickening of blood vessel walls after vascular operations, and for preventing arteriosclerosis and diabetic angiopathy. In view of the effects of angiotensin on the release of acetylcholine and dopamine in the brain, the new angiotensin antagonists are also suitable for alleviating central nervous system disorders, e.g. depression, Alzheimer's disease, parkinson syndrome, bulimia and disorders of cognitive function.

The dosage required to achieve these effects in adults is appropriately, when administered intravenously, 20 to 100 mg, preferably 30 to 70 mg, and, when administered orally, 50 to 200 mg, preferably 75 to 150 mg, 1 to 3 times a day. For this purpose, the compounds of general formula I prepared according to the invention, optionally in conjunction with other active substances, such as hypotensives, diuretics and/or calcium antagonists, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene-glycol, propyleneglycol, cetylstearyl alcohol, carboxymethylcellulose or fatty substances such as hard fat or suitable mixtures thereof, in conventional galenic preparations such as plain or coated tablets, capsules, powders, suspensions or suppositories.

Additional active substances which may be included in the combinations mentioned above might be, for example, bendroflumethiazide, chlorothiazide, hydrochlorothiazide, spironolactone, benzothiazide, cyclothiazide, ethacrinic acid, furosemide, metoprolol, prazosine, atenolol, propranolol, (di)hydralazine-hydrochloride, diltiazem, felodipin, nicardipin, nifedipin, nisoldipin and nitrendipin. The dosage for these active substances is appropriately one fifth of the lowest recommended dose up to ½ of the normally recommended dose, i.e., for example, 15 to 200 mg of hydrochlorothiazide, 125 to 2000 mg of chlorothiazide, 15 to 200 mg of ethacrinic acid, 5 to 80 mg of furosemide, 20 to 480 mg of propranolol, 5 to 60 mg of felodipine, 5 to 60 mg of nifedipin or 5 to 60 mg of nitrendipin.

The Examples which follow are intended to illustrate the invention:

EXAMPLE A 4-(α-Ethoxycarbonyl-benzyloxy)benzylbromide a) Ethyl 2-bromo-phenylacetate 43.0 g (0.2 mol) of DL-2-bromo-phenylacetic acid are dissolved in 400 ml of ethanol at ambient temperature with stirring. At 5°–10° C. 11.8 g (0.2 mol) of thionylchloride are slowly added dropwise whilst cooling with ice. After 12 hours at ambient temperature the solvent is distilled off and the residue is taken up in ethyl acetate. After extraction with saturated sodium bicarbonate solution and saturated saline solution the product is dried over sodium sulphate and evaporated down.

Yield: 41.85 g (86% of theory), $R_f$ value: 0.60 (silica gel; eluant: ethyl acetate/petroleum ether=1:19)

b) 4-(α-Ethoxycarbonyl-benzyloxy)benzyl alcohol 41.8 g (0.172 mol) of ethyl 2-bromo-phenylacetate and 21.3 g (0.172 mol) of 4-hydroxybenzyl alcohol are dissolved in 850 ml of acetone and 24.8 g (0.18 mol) of potassium carbonate and 5.0 g (0.03 mol) of potassium iodide are added thereto. The reaction mixture is refluxed for 60 hours with stirring. Then the inorganic salts are filtered off and the residue is washed with hot acetone. The filtrate is evaporated down and the residue is purified over a silica gel column (particle size: 0.063–0.02 mm), initially using petroleum ether as eluant and then using mixtures of petroleum ether and ethyl acetate of increasing polarity (9:1, 8:2 and 7:3). The unified fractions are evaporated down in vacuo.

Yield: 30.65 g (62.5% of theory), $R_f$ value: 0.40 (silica gel; eluant: ethyl acetate/petroleum ether=3:7)

c) 4(α-Ethoxycarbonyl-benzyloxy)benzylbromide 28.6 g (0.1 mol) of 4-(α-ethoxycarbonyl-benzyloxy)benzyl alcohol are dissolved in 300 ml of dichloromethane and mixed with 31.6 g (0.12 mol) of triphenylphosphine. Whilst cooling with ice, a solution of 40.0 g (0.12 mol) of carbon tetrabromide in 100 ml of dichloromethane is added dropwise. The mixture is stirred for 30 minutes at ambient temperature and then concentrated by evaporation. The residue is purified over a silica gel column (particle size: 0.063–0.02 mm), using as eluant first petroleum ether and then mixtures of petroleum ether and ethyl acetate of increasing polarity (9:1 and 8:2). The unified fractions are evaporated down in vacuo.

Yield: 20.45 g (59% of theory), Oil, $R_f$ value: 0.70 (silica gel; eluant: ethyl acetate/petroleum ether=1:4) $C_{17}H_{16}BrO_3$ (349.24) Calculated: C 58.20 H 4.95 Br 22.80 Found: 58.23 4.84 23.12

EXAMPLE 1

2-n-Propyl-4-methyl-1-[4-[(α-carboxy)benzyloxy]benzyl]benzimidazole

2-n-Propyl-4-methyl-1-[4-[(α-ethoxycarbonyl)benzyloxy]benzyl]benzimidazole 350 mg (2.0 mMol) of 2-n-propyl-4-methyl-benzimidazole (prepared analogously to Chemistry of Heterocyclic Compounds, Vol. 40, part 1, 6–12) are added to a solution of 220 mg of potassium tert.butoxide in 30 ml of dimethylsulphoxide. After 30 minutes at ambient temperature a solution of 700 mg (2.0 mMol) of 4-(α-ethoxycarbonyl-benzyloxy)benzylbromide in 5 ml of dimethylsulphoxide is added dropwise. After 12 hours at ambient temperature the reaction solution is stirred into ice water and extracted 3 times with 100 ml of ethyl acetate. The combined organic phases are washed with 100 ml of saline solution and dried over sodium sulphate. After the solvent has been eliminated, the residue is purified over a silica gel column (particle size 0.063–0.02 mm), using as eluant methylene chloride to start with, then mixtures of methylene chloride and ethanol of increasing polarity (50:1 and 25:1). The uniform fractions are concentrated by evaporation in vacuo.

Yield: 500 mg (55% of theory), Oil, $R_f$ value: 0.55 (silica gel; eluant: methylene chloride/methanol=19:1)

b) 2-n-Propyl-4-methyl-1-[4-[(α-carboxy)benzyloxy]benzyl]benzimidazole 500 mg (1.1 mMol) of 2-n-propyl-4-methyl-1-[4-[(α-ethoxycarbonyl)benzyloxy]benzyl] benzimidazole are dissolved in 10 ml of ethanol and mixed with 10 ml of 1N sodium hydroxide solution. The mixture is stirred at ambient temperature for 30 minutes. Then the mixture is concentrated by evaporation and taken up in water. The solution is acidified by the addition of glacial acetic acid. The precipitate formed is suction filtered, washed with water until neutral and dried. The crude product is taken up in methylene chloride and purified over a silica gel column (particle size 0.063–0.02 mm), using as eluant a mixture of methylene chloride and methanol (19: 1). The uniform fractions are concentrated by evaporation in vacuo and the residue is triturated with hexane/ether and suction filtered.

Yield: 60 mg (13% of theory), Melting point: amorphous $C_{26}H_{26}N_2O_3$ (414.51) Mass spectrum: $(M+H)^+=415$

EXAMPLE 2

2-n-Butyl-1-[4-[(α-carboxy)benzyloxy]benzyl]-6-propionylamino-benzimidazole-hydrochloride a) 2-n-butyl-1-[4-[(α-ethoxycarbonyl)benzyloxy]benzyl]- 6-nitro-benzimidazole and 2-n-butyl-1-[4-[(α-ethoxycarbonyl)benzyloxy]benzyl]-5-nitro-benzimidazole Prepared analogously to Example 1a from 2-n-butyl-5-nitrobenzimidazole (prepared analogously to Chemistry of Heterocyclic Compounds, Vol. 40, Part 1, 6–12) and 4-[(α-ethoxycarbonyl)benzyloxy]benzylbromide.

Yield: 70.5% of theory, Oil, $R_f$ value: 0.25 (silica gel; eluant: methylene chloride/ethanol=50:1)

b) 2-n-Butyl-6-amino-1-[4-[(α-ethoxycarbonyl)benzyloxy]-benzyl]-benzimidazole Prepared by catalytic hydrogenation of 2-n-butyl-1-[4-[(α-ethoxycarbonyl)benzyloxy]benzyl] -5/6-nitro-benzimidazole in the presence of Raney nickel in ethanol at 50° C. under 5 bars of hydrogen pressure, followed by chromatographic separation of the 5-amino-2-n-butyl-1-[4-[(α-ethoxycarbonyl)-benzyloxy]benzyl]benzimidazole.

Yield: 21.8% of theory, Oil, $R_f$ value: 0.30 (silica gel; eluant: petroleum ether/methylene chloride/ethanol=7:2:1)

2-n-Butyl-6-propionylamino-1-[4-[(α-ethoxycarbonyl)-benzyloxy]benzyl]benzimidazole Prepared from 2-n-butyl-6-amino-1-[4-[(α-ethoxycarbonyl)benzyloxy]benzyl]benzimidazole and propionyl chloride/pyridine.

Yield: 70.2% of theory, Melting point: 207°–209° C.

d) 2-n-Butyl-1-[4-[(α-carboxy)benzyloxy]benzyl]-6-propionylamino-benzimidazole-hydrochloride Prepared analogously to Example 1b from 2-n-butyl-6-propionylamino-1-[4-[(α-ethoxycarbonyl)benzyloxy] benzyl]benzimidazole and 1N sodium hydroxide solution in ethanol.

Yield: 43.5% of theory, Melting point: sinters from 93° C. $C_{29}H_{31}N_3O_4 \times HCl$ (522.67) Calculated: C 66.50 H 6.12 N 8.08 Found: 66.73 6.34 7.81

EXAMPLE 3

2-n-Butyl-1-[4-[(α-carboxy)benzyloxy]benzyl]-6-dimethylaminocarbonylamino-benzimidazole Prepared analogously to Example 1b from 2-n-butyl-1-[4-[(α-ethoxycarbonyl)benzyloxy]benzyl]-6 -dimethylamino-carbonylaminobenzimidazole and 2N sodium hydroxide solution in ethanol.

Yield: 80% of theory, Melting point: 183°–185° C. $C_{29}H_{32}N_4O_4$ (500.60) Calculated: C 69.59 H 6.44 N 11.19 Found: 69.54 6.43 10.66

EXAMPLE 4

2-n-Butyl-1-[4-[(α-carboxy)benzyloxy]benzyl]-6 -cyclohexylaminocarbonylamino-benzimidazole-hydrochloride a) 2-n-Butyl-1-[4-[(α-ethoxycarbonyl)benzyloxy]benzyl]-6-cyclohexylaminocarbonylamino-benzimidazole Prepared from 2-n-butyl-1-[4-[(α-ethoxycarbonyl)benzyloxy]benzyl]-6-amino-benzimidazole and cyclohexylisocyanate/triethylamine in tetrahydrofuran.

Yield: 65.4% of theory, Oil, $R_f$ value: 0.40 (silica gel; eluant: methylene chloride/ethanol=19:1)

b) 2-n-Butyl-1-[4-[(α-carboxy)benzyloxy]benzyl]-6 -cyclohexylaminocarbonylamino-benzimidazole-hydrochloride Prepared analogously to Example 1b from 2-n-butyl-1-[4-[(α-ethoxycarbonyl)benzyloxy]benzyl]-6 -cyclohexylamino-carbonylaminobenzimidazole and 1N sodium hydroxide solution in ethanol.

Yield: 40.7% of theory, Melting point: sinters from 184° C. $C_{33}H_{38}N_4O_4 \times HCl$ (591.17) Calculated: C 67.00 H 6.60 N 9.45 Found: 67.15 6.71 9.30

EXAMPLE 5

2-n-Butyl-1-[4-[(α-carboxy)benzyloxy]benzyl]-5-cyclohexylaminocarbonylamino-benzimidazole-hydrochloride Prepared analogously to Example 1b from 2-n-butyl-1-[4-[(α-ethoxycarbonyl)benzyloxy]benzyl]-5 -cyclohexylamino-carbonylaminobenzimidazole and 1N sodium hydroxide solution in ethanol.

Yield: 46.1% of theory, Melting point: sinters from 196° C. $C_{33}H_{38}N_4O_4 \times HCl$ (591.17) Calculated: C 67.00 H 6.60N 9.45 Found: 67.22 6.74 9.49

EXAMPLE 6

2-n-Butyl-1-[4-[(α-carboxy)benzyloxy]benzyl]-6-(3,4,5,6-tetrahydro-2(1H)-pyrimidinon-1-yl)-benzimidazole Prepared analogously to Example 1b from 2-n-butyl-1-[4-[(α-ethoxycarbonyl)benzyloxy]benzyl]-6 -(3,4,5,6-tetrahydro-2(1H)-pyrimidinon-1-yl)-benzimidazole and 1N sodium hydroxide solution in ethanol.

Yield: 8.8% of theory, Melting point: 260°–262° C. $C_{30}H_{32}N_4O_4$ (512.61) Mass spectrum: $(M+H)^+=513$

EXAMPLE 7

2-n-Butyl-1-[4-[(α-carboxy)benzyloxy]benzyl]-6-(3-benzyl-3,4,5,6-tetrahydro-2(1H)-pyrimidinon-1-yl)-benzimidazole Prepared analogously to Example 1b from 2-n-butyl-1-[4-[(α-ethoxycarbonyl)benzyloxy]benzyl]-6 -(3-benzyl-3,4,5,6-tetrahydro-2(1H)-pyrimidinon-1-yl)-benzimidazole and 1N sodium hydroxide solution in ethanol.

Yield: 80.4% of theory, Melting point: 124°–126° C. $C_{37}H_{38}N_4O_4$ (602.74) Calculated: C 73.73 H 6.35N 9.30 Found: 73.47 6.50 9.05

EXAMPLE 8

2-n-Butyl-1-[4-[(α-carboxy)benzyloxy]benzyl]-6-(N-cyclohexylaminocarbonyl-methylamino)-benzimidazole a)
2-n-Butyl-1-[4-[(α-ethoxycarbonyl)benzyloxy]benzyl]-6 -(N-cyclohexylaminocarbonyl-methylamino)-benzimidazole Prepared analogously to Example 1a from 2-n-butyl-6-(N-cyclohexylaminocarbonyl-methylamino)benzimidazole and 4-[(α-ethoxycarbonyl)-benzyloxy]benzylbromide and subsequent chromatographic separation of the 2-n-butyl-1-[4-[(α-ethoxycarbonyl)benzyloxy]benzyl]-5 -(N-cyclohexylaminocarbonyl-methylamino)-benzimidazole.

Yield: 50.0% of theory, Oil, $R_f$ value: 0.50 (silica gel; eluant: methylethyl ketone/xylene=1:1)

b) 2-n-Butyl-1-[4-[(α-carboxy)benzyloxy]benzyl]-6-(N-cyclohexylaminocarbonyl-methylamino) benzimidazole Prepared analogously to Example 1b from 2-n-butyl-1-[4-[(α-ethoxycarbonyl)benzyloxy]benzyl]-6 -(N-cyclohexyl-aminocarbonylmethylamino)benzimidazole and 1N sodium hydroxide solution in ethanol.

Yield: 93.0% of theory, Melting point: 168°–169° C. $C_{34}H_{40}N_4O_4$ (568.72) Calculated: C 71.81 H 7.09N 9.85 Found: 71.78 7.02 9.71

EXAMPLE 9

2-n-propyl-5-(2-methyl-propionylamino)-3-[4-[(α-carboxy)benzyloxy]benzyl]imidazo[4,5-b]pyridine a) 2-n-Propyl-5-(2-methyl-propionylamino)-imidazo[4,5-b]pyridine 2.62 g (15 mMol) of 2-n-propyl-5-amino-imidazo[4,5-b]pyridine are suspended in 100 ml of absolute methylene chloride and 3.16 g (30 mMol) of isobutyric acid chloride are added, with stirring and cooling with ice. Then, at −5° C., a solution of 3.03 g (30 mMol) of triethylamine in 5 ml of methylene chloride is added dropwise. After one hour at ambient temperature the reaction mixture is combined with 100 ml of 2N hydrochloric acid and the mixture is stirred for a further hour. Then the solution is poured onto ice water and mixed with saturated sodium hydrogen carbonate solution. The aqueous phase is extracted 3 times with 100 ml of ethyl acetate, the combined organic phases are then washed with saline solution, dried over sodium sulphate and concentrated by evaporation. The crude product is taken up in methylene chloride and purified over a silica gel column (particle size 0.063–0.2 mm), using as eluant methylene chloride to begin with, followed by mixtures of methylene chloride and ethanol of increasing polarity (25:1 and 19:1). The unified fractions are concentrated by evaporation and the residue is triturated with petroleum ether/ether=1:1 and suction filtered.

Yield: 2.05 g (56% of theory), Melting point: 206° C. $C_{13}H_{18}N_4O$ (246.30) Calculated: C 63.39 H 7.37N 22.75 Found: 63.64 7.57 22.98 b) 2-n-Propyl-5-(2-methyl-propionylamino)-3-[4-[(α-ethoxycarbonyl)benzyloxy]benzyl]imidazo[4,5-b]-pyridine Prepared analogously to Example 1a from 2-n-propyl-5-(2-methylpropionylamino)imidazo[4,5-b]pyridine and 4-[(α-ethoxycarbonyl)benzyloxy]benzylbromide.

Yield: 33.7% of theory, Melting point: 100°–101° C.

c) 2-n-Propyl-5-(2-methyl-propionylamino)-3-[4-[(α-carboxy)benzyloxy]benzyl]imidazo[4,5-b]pyridine Prepared analogously to Example 1b from 2-n-propyl-5-(2-methylpropionylamino)-3-[4 -[(α-ethoxycarbonyl)benzyloxy]benzyl]imidazo[4,5-b]pyridine and 1N sodium hydroxide solution in ethanol.

Yield: 52.0% of theory, Melting point: 134° C. $C_{28}H_{30}N_4O_4$ (486.58) Calculated: C 69.12 H 6.21N 11.51 Found: 69.03 6.11 11.36

EXAMPLE 10

2-n-Butyl-5-valeroylamino-3-[4-[(α-carboxy) benzyloxy]benzyl]imidazo[4,5-b]pyridine-semihydrate Prepared analogously to Example 1b from 2-n-butyl-5-valeroylamino-3-[4 -[(α-ethoxycarbonyl)benzyloxy]benzyl]imidazo[4,5-b]pyridine and 1N sodium hydroxide solution in ethanol.

Yield: 57.0% of theory, Melting point: sinters from 96° C. $C_{30}H_{34}N_4O_4 \times 0.5\ H_2O$ (532.65) Calculated: C 68.82 H 6.74 N 10.70 Found: 68.99 6.67 10.58

EXAMPLE 11

2-n-Propyl-5-(1-methyl-benzimidazol-2-yl)-7-methyl-3-[4 -[(α-carboxy)benzyloxy]benzyl]imidazo[4,5-b]pyridine Prepared analogously to Example 1b from 2-n-propyl-5-(1-methyl-benzimidazol-2-yl)-7-methyl-3 -[4-[(α-ethoxycarbonyl)benzyloxy]benzyl-imidazo[4,5-b]pyridine and 1N sodium hydroxide solution in ethanol.

Yield: 41.4% of theory, Melting point: 242°–244° C. $C_{33}H_{31}N_5O_3$ (545.65) Calculated: C 72.64 H 5.73 N 12.83 Found: 72.51 5.75 12.97

EXAMPLE 12

2-n-Propyl-6-(1-methyl-benzimidazol-2-yl)-4-methyl-1-[4 -[(α-carboxy)benzyloxy]benzyl]benzimidazole Prepared analogously to Example 1b from 2-n-propyl-6-(1-methyl-benzimidazol-2-yl)-4-methyl-1 -[4-[(α-ethoxycarbonyl)benzyloxy]benzyl]benzimidazole and 1N sodium hydroxide solution in ethanol.

Yield: 41.0% of theory, Melting point: amorphous $C_{34}H_{32}N_4O_3$ (544.66) Calculated: C 74.98 H 5.92 N 10.28 Found: 74.55 6.06 10.08 Mass spectrum: $(M+H)^+=545$

EXAMPLE 13

2-Methyl-4-[4'-[(α-carboxy)benzyloxy]benzyloxy] quinoline a) 2-Methyl-4-[4'-[(α-ethoxycarbonyl)benzyloxy]-benzyloxy]quinoline Prepared analogously to Example 1a from 4-hydroxyquinaldine and 4-[(α-ethoxycarbonyl)benzyloxy]benzylbromide.

Yield: 19.8% of theory, Oil, $R_f$ value: 0.55 (silica gel; eluant: methylene chloride/ethanol=19:1)

b) 2-Methyl-4-[4'-[(α-carboxy) benzyloxy]benzyloxy]- quinoline

Prepared analogously to Example 1b from 2-methyl-4-[4'-[(α-ethoxycarbonyl)benzyloxy]benzyloxy-quinoline and 1N sodium hydroxide solution in ethanol.

Yield: 66.6% of theory, Melting point: 142°–143° C. $C_{25}H_{21}NO_4$ (399.50) Calculated: C 73.17 H 5.30 N 3.51 Found: 73.56 5.25 3.34 Mass spectrum: $(M+H)^+=400$

EXAMPLE 14

2-n-Propyl-5-n-butyrylamino-3-[4-[(1-carboxy-3-methyl)butyloxy]benzyl]imidazo[4,5 -b]pyridine a) 2-n-Propyl-5-n-butyrylamino-3-[4- [(1-methoxycarbonyl-3 -methyl)butyloxy]benzyl]imidazo[4,5-b]pyridine Prepared analogously to Example 1a from 2-n-Propyl-5-n-butyrylamino-imidazo[4,5-b]pyridine and 4 -[(1-methoxycarbonyl-3-methyl)butyloxy]benzylbromide, with subsequent chromatographic separation of the 2-n-propyl-5-n-butyrylamino-1-[4-[(1-methoxycarbonyl-3 -methyl)-butyloxy]benzyl]imidazo[4,5-b]pyridine.

Yield: 47.0% of theory, Oil, $R_f$ value: 0.30 (silica gel; eluant: methylene chloride/ethanol=19:1)

b) 2-n-Propyl-5-n-butyrylamino-3-[4-(1-carboxy-3-methyl)-butyloxy]benzyl]imidazo[4,5 -b]pyridine Prepared analogously to Example 1b from 2-n-propyl-5-n-butyrylamino-3-[4-(1-methoxycarbonyl-3 -methyl)-butyloxy]benzyl]imidazo[4,5-b]pyridine and 1N sodium hydroxide solution in ethanol.

Yield: 59.0% of theory, Melting point: 147°–148° C. $C_{26}H_{34}N_4O_4$ (466.59) Calculated: C 66.93 H 7.35 N 12.01 Found: 66.69 7.48 11.85

EXAMPLE 15

2-n-Butyl-1-[4-[(α-carboxy)cyclohexylmethyloxy] benzyl]benzimidazole

Prepared analogously to Example 1b from 2-n-butyl-1-[4 -[(α-methoxycarbonyl)cyclohexylmethyloxy]benzyl]-benzimidazole and 1N sodium hydroxide solution in ethanol.

Yield: 92.0% of theory, Melting point: 208° C. (decomp.) $C_{26}H_{32}N_2O_3$ (420.56) Calculated: C 74.25 H 7.66 N 6.66 Found: 73.98 7.52 6.41

EXAMPLE 16

2-n-Butyl-4-chloro-5-hydroxymethyl-1-[4- [(α-carboxy)benzyloxy]benzyl]imidazole a) 2-n-Butyl-4-chloro-5-hydroxymethyl-1-[4- [(α-methoxycarbonyl)benzyloxy]benzyl]imidazole Prepared analogously to Example 1a from 2-n-butyl-4-chloro-5-hydroxymethyl-imidazole and 4-[(α-methoxycarbonyl]benzyloxy]benzylbromide, with subsequent chromatographic separation of the 2-n-butyl-5-chloro-4-hydroxymethyl-1-[4 -[(α-methoxycarbonyl)benzyloxy] benzyl]imidazole.

Yield: 21.0% of theory, Oil, $R_f$ value: 0.70 (silica gel; eluant: methylene chloride/methanol=6:1)

b) 2-n-Butyl-4-chloro-5-hydroxymethyl-1-[4- [(α-carboxy)-benzyloxy]benzyl]imidazole-hydrochloride Prepared analogously to Example 1b from 2-n-butyl-4-chloro-5-hydroxymethyl-1-[4 -[(α-methoxycarbonyl-benzyloxy]benzyl]imidazole and 1N sodium hydroxide solution in ethanol.

Yield: 34.0% of theory, Melting point: 176° C. $C_{23}H_{25}ClN_2O_4$ HCl (465.38) Calculated: C 59.36 H 5.63 6.02 Found: 59.53 5.43 5.97

EXAMPLE 17

2-n-Butyl-5-chloro-4-hydroxymethyl-1-[4-[(1-carboxy-3-methyl)butyloxy]benzyl]imidazole Prepared analogously to Example 1b from 2-n-butyl-5-chloro-4-hydroxymethyl-1-[4-[(1 -methoxycarbonyl-3-methyl)butyloxy]benzyl]imidazole and 1N sodium hydroxide solution in ethanol.

Yield: 66.0% of theory, Melting point: 175°–176° C. $C_{21}H_{29}ClN_2O_4$ (408.93) Calculated: C 61.68 H 7.14 N 6.84 Found: 61.34 7.11 6.58

EXAMPLE 18

2-n-Butyl-5-chloro-4-hydroxymethyl-1-[4-[(1-carboxy)-n-propyloxy]benzyl]imidazole Prepared analogously to Example 1b from 2-n-butyl-5-chloro-4-hydroxymethyl-1-[4-[(1 -methoxycarbonyl)-n-propyloxy]benzyl]imidazole and 1N sodium hydroxide solution in ethanol.

Yield: 70.0% of theory, Melting point: 182°–184° C. $C_{19}H_{25}ClN_2O_4$ (380.88) Calculated: C 59.91 H 6.61 N 7.35 Found: 59.67 6.53 7.22

EXAMPLE 19

2-n-Butyl-4-chloro-5-hydroxymethyl-1-[4-[(1-carboxy)-n-propyloxy]benzyl]imidazole Prepared analogously to Example 1b from 2-n-butyl-4-chloro-5-hydroxymethyl-1-[4-[(1 -methoxycarbonyl)-n-propyloxy]benzyl]imidazole and 1N sodium hydroxide solution in ethanol.

Yield: 66.0% of theory, Melting point: 125°–127° C. $C_{19}H_{25}ClN_2O_4$ (380.88) Calculated: C 59.91 H 6.61 N 7.35 Found: 59.74 6.60 6.90

EXAMPLE 20

2-n-Butyl-4-chloro-5-methoxymethyl-1-[4-[(α-carboxy)benzyloxy]benzyl]imidazole

Prepared analogously to Example 1b from 2-n-butyl-4-chloro-5-methoxymethyl-1-[4 -[(α-methoxycarbonyl)-benzyloxy]benzyl]imidazole and 1N sodium hydroxide solution in ethanol.

Yield: 45.0% of theory, Melting point: 156°–158° C. $C_{24}H_{27}ClN_2O_4$ (442.95) Calculated: C 65.08 H 6.14 N 6.32 Found: 64.70 6.38 6.03

EXAMPLE 21

2-n-Butyl-4-chloro-5-hydroxymethyl-1-[4-[(1-carboxy-3-methyl)butyloxy]benzyl]imidazole Prepared analogously to Example 1b from 2-n-butyl-4-chloro-5-hydroxy-methyl-1-[4 -[(1-methoxycarbonyl-3-methyl)butyloxy]benzyl]imidazole and 1N sodium hydroxide solution in ethanol.

Yield: 57.0% of theory, Melting point: 164°–165° C. $C_{21}H_{29}ClN_2O_4$ (408.93) Calculated: C 61.68 H 7.14 N 6.84 Found: 61.63 7.09 6.71

EXAMPLE 22

2-n-Butyl-4-hydroxymethyl-5-chloro-1-[4-[(α-carboxy)benzyloxy]benzyl]imidazole

Prepared analogously to Example 1b from 2-n-butyl-4-hydroxymethyl-5-chloro-1 -[4-[(α-methoxycarbonyl)benzyloxy]benzyl]imidazole and 1N sodium hydroxide solution in ethanol.

Yield: 18.0% of theory, Melting point: 193° C. $C_{23}H_{25}ClN_2O_4$ (428.92) $R_f$ value: 0.10 (silica gel; eluant: methylene chloride/methanol=9:1) Mass spectrum: $(M+H)^+$ =394/396 (Cl)

EXAMPLE 23

2-n-Butyl-5-chloro-4-hydroxymethyl-1-[4-[(1-carboxy)-n-butyloxy]benzyl]imidazole Prepared analogously to Example 1b from 2-n-butyl-5-chloro-4-hydroxymethyl-1-[4 -[(1-methoxycarbonyl)-n-butyloxy]benzyl]imidazole and 1N sodium hydroxide solution in ethanol.

Yield: 27.0% of theory, Melting point: 154° C. $C_{20}H_{27}ClN_2O_4$ (394.90) $R_f$ value: 0.20–0.30 (silica gel; eluant: methylene chloride/methanol=9:1) Mass spectrum: $(M+H)^+$=394/396 (Cl)

EXAMPLE 24

2-n-Butyl-4-hydroxymethyl-5-chloro-1-[4-[(α-carboxy)-p-phenylbenzyloxy]benzyl]imidazole Prepared analogously to Example 1b from 2-n-butyl-4-hydroxymethyl-5-chloro-1 -[4-[(α-methoxycarbonyl)-p-phenylbenzyloxy]benzyl]imidazole and 1N sodium hydroxide solution in ethanol.

Yield: 72.0% of theory, Melting point: 182° C. $C_{29}H_{29}ClN_2O_4$ (505.02) Calculated: C 68.97 H 5.78 N 5.54 Found: 68.50 5.83 5.46

EXAMPLE 25

2-n-Butyl-4-chloro-5-hydroxymethyl-1-[4-[(α-carboxy)-p-phenylbenzyloxy]benzyl]imidazole Prepared analogously to Example 1b from 2-n-butyl-4-chloro-5-hydroxymethyl-1-[4 -[(α-methoxycarbonyl)-p-phenylbenzyloxy]benzyl]imidazole and 1N sodium hydroxide solution in ethanol.

Yield: 75.0% of theory, Melting point: 185°–186° C. (decomp.) $C_{29}H_{29}ClN_2O_4$ (505.02) Calculated: C 68.97 H 5.78 N 5.54 Found: 68.87 5.80 5.42

EXAMPLE 26

2-n-Butyl-4-hydroxymethyl-5-chloro-1-[4-[(α-carboxy)-2-naphthylmethyloxy]benzyl]imidazole-semihydrate Prepared analogously to Example 1b from 2-n-butyl-4-hydroxymethyl-5-chloro-1-[4 -[(α-methoxycarbonyl)-2-naphthylmethyloxy]benzyl]imidazole and 1N sodium hydroxide solution in ethanol.

Yield: 69.0% of theory, Melting point: from 188° C. (decomp.) $C_{27}H_{27}ClN_2O_4 \times 0.5\ H_2O$ (487.99) Calculated: C 66.45 H 5.78 N 5.74 Found: 66.63 5.66 5.75

EXAMPLE 27

2-n-Butyl-4-chloro-5-hydroxymethyl-1-[4-[(α-carboxy)-2-naphthylmethyloxy]benzyl]imidazole-semihydrate Prepared analogously to Example 1b from 2-n-butyl-4-chloro-5-hydroxymethyl-1-[4 -[(α-methoxycarbonyl)-2-naphthylmethyloxy]benzyl]imidazole and 1N sodium hydroxide solution in ethanol.

Yield: 82.0% of theory, Melting point: from 142° C. (decomp.) $C_{27}H_{27}ClN_2O_4 \times 0.5\ H_2O$ (487.99) Calculated: C 66.45 H 5.78 N 5.74 Found: 66.62 5.66 6.12

EXAMPLE 28

2-n-Butyl-4-hydroxymethyl-5-chloro-1-[4-[(α-carboxy)-1-naphthylmethyloxy]benzyl]imidazole-hydrate Prepared analogously to Example 1b from 2-n-butyl-4-hydroxymethyl-5-chloro-1 -[4-[(α-methoxycarbonyl)-1-naphthylmethyloxy]benzyl]imidazole and 1N sodium hydroxide solution in ethanol.

Yield: 91.0% of theory, Melting point: from 110° C. (decomp.) $C_{27}H_{27}ClN_2O_4 \times H_2O$ (497.00) Calculated: C 65.25 H 5.88 N 5.63 Found: 65.58 5.89 5.83

EXAMPLE 29

2-n-Butyl-4-chloro-5-hydroxymethyl-1-[4-[(α-carboxy)-1-naphthylmethyloxy]benzyl]imidazole-hydrate Prepared analogously to Example 1b from 2-n-butyl-4-chloro-5-hydroxymethyl-1-[4 -[(α-methoxycarbonyl)-1-naphthylmethyloxy]benzyl]imidazole and 1N sodium hydroxide solution in ethanol.

Yield: 42.0% of theory, Melting point: from 100° C. (decomp.) $C_{27}H_{27}ClN_2O_4 \times H_2O$ (497.00) Calculated: C 65.25 H 5.88 N 5.63 Found: 65.21 5.70 6.10

EXAMPLE 30

2-n-Butyl-4-chloro-5-hydroxymethyl-1-[4-[(α-carboxy)-p-methoxybenzyloxy]benzyl]imidazole Prepared analogously to Example 1b from 2-n-butyl-4-chloro-5-hydroxymethyl-1-[4 -[(α-methoxycarbonyl)-p-methoxybenzyloxy]benzyl]imidazole and 1N sodium hydroxide solution in ethanol.

Yield: 58.0% of theory, Melting point: 165° C. $C_{24}H_{27}ClN_2O_5$ (458.95) Calculated: C 62.81 H 5.93 N 6.10 Found: 62.69 6.02 5.93

EXAMPLE 31

2-n-Butyl-4-chloro-5-methoxymethyl-1-[4-[(1-carboxy)-n-pentyloxy]benzyl]imidazole Prepared analogously to Example 1b from 2-n-butyl-4-chloro-5-methoxymethyl-1-[4 -[(1-methoxycarbonyl)-n-pentyloxy]benzyl]imidazole and 1N sodium hydroxide solution in ethanol.

Yield: 84.0% of theory, Melting point: 168° C. $C_{22}H_{31}ClN_2O_4$ (422.96) Calculated: C 62.45 H 7.38 N 6.62 Found: 62.23 7.47 6.79

EXAMPLE 32

2-n-Butyl-4-chloro-5-hydroxymethyl-1-[4-[(1-carboxy)-n-butyloxy]benzyl]imidazole Prepared analogously to Example 1b from 2-n-butyl-4-chloro-5-hydroxymethyl-1-[4 -[(1-methoxycarbonyl)-n-butyloxy]benzyl]imidazole and 1N sodium hydroxide solution in ethanol.

Yield: 50.0% of theory, Melting point: 137°–138° C. $C_{20}H_{27}ClN_2O_4$ (394.90) Calculated: C 60.83 H 6.89 N 7.09 Found: 60.67 6.94 6.67

EXAMPLE 33

2-n-Butyl-4-chloro-5-hydroxymethyl-1-[4-[(1-carboxy)-n-pentyloxy]benzyl]imidazole Prepared analogously to Example 1b from 2-n-butyl-4-chloro-5-hydroxymethyl-1-[4 -[(1-methoxycarbonyl)-n-pentyloxy]benzyl]imidazole and 1N sodium hydroxide solution in ethanol.

Yield: 61.0% of theory, Melting point: 150° C. $C_{21}H_{29}ClN_2O_4$ (408.93) Calculated: C 61.65 H 7.14 N 6.85 Found: 62.31 6.85 7.21

EXAMPLE 34

2-n-Butyl-4-hydroxymethyl-5-chloro-1-[4-[(1-carboxy)-n-pentyloxy]benzyl]imidazole Prepared analogously to Example 1b from 2-n-butyl-4-hydroxymethyl-5-chloro-1-[4 -[(1-methoxycarbonyl)-n-pentyloxy]benzyl]imidazole and 1N sodium hydroxide solution in ethanol.

Yield: 57.0% of theory, Melting point: 168° C. $C_{21}H_{29}ClN_2O_4$ (408.93) Calculated: C 61.65 H 7.14 N 6.85 Found: 61.59 7.11 6.91

EXAMPLE 35

2-n-Butyl-8-methyl-3-[4-[(α-carboxy)benzyloxy]benzyl]-quinazolin-4-one-semihydrate a) 2-n-Butyl-8-methyl-3-[4-[(α-ethoxycarbonyl)benzyloxy]benzyl]quinazolin-4-one Prepared analogously to Example 1a from 2-n-butyl-8-methyl-quinazolin-4(1H)-one and 4 -(α-ethoxycarbonylbenzyloxy)benzylbromide.

Yield: 37% of theory, Oil, $R_f$ value: 0.45 (silica gel; eluant: petroleum ether/ethyl acetate=4:1)

b) 2-n-Butyl-8-methyl-3-[4-[(α-carboxy)benzyloxy]benzyl]quinazolin-4-one-semihydrate Prepared analogously to Example 1b from 2-n-butyl-8-methyl-3 -[(α-ethoxycarbonyl)benzyloxy]benzyl]-quinazolin-4-one and 1N sodium hydroxide solution in ethanol.

Yield: 84% of theory, Melting point: 201°–204° C. $C_{28}H_{28}N_2O_4 \times 0.5\ H_2O$ (465.56) Calculated: C 72.24 H 6.28 N 6.02 Found: 72.41 6.33 5.75

EXAMPLE 36

2-n-Butyl-4-chloro-5-hydroxymethyl-1-[4-[(1-carboxy-2-cyclohexyl)ethoxy]benzyl]imidazole Prepared analogously to Example 1b from 2-n-butyl-4-chloro-5-hydroxymethyl-1-[4 -[(1-methoxycarbonyl-2-cyclohexyl)ethoxy]benzyl]imidazole and 1N sodium hydroxide solution in ethanol.

Yield: 67.1% of theory, Melting point: 145°–150° C. $C_{24}H_{33}ClN_2O_4$ (448.96) Calculated: C 64.20 H 7.40 N 6.24 Found: 63.97 7.38 6.01

EXAMPLE 37

2-n-Butyl-4-hydroxymethyl-5-chloro-1-[4-[(1-carboxy-2-cyclohexyl)ethoxy]benzyl]imidazole Prepared analogously to Example 1b from 2-n-butyl-4-hydroxymethyl-5-chloro-1-[4 -[(1-methoxycarbonyl-2-cyclohexyl)ethoxy]benzyl]imidazole and 1N sodium hydroxide solution in ethanol.

Yield: 59.1% of theory, Melting point: 180°–183° C. $C_{24}H_{33}ClN_2O_4$ (448.96) Calculated: C 64.20 H 7.40 N 6.24 Found: 63.99 7.20 6.27 Mass spectrum: m/e=448/450 (Cl)

EXAMPLE 38

2-n-Butyl-1-[4-[(1-carboxy-3-methyl)butyloxy]benzyl]benzimidazole

Prepared analogously to Example 1b from 2-n-butyl-1-[4-[(1-methoxycarbonyl-3 -methyl)butyloxy]benzyl]-benzimidazole and 1N sodium hydroxide solution in ethanol.

Yield: 82.3% of theory, Melting point: 150°–152° C. $C_{24}H_{30}N_2O_3$ (394.52) Calculated: C 73.07 H 7.66 N 7.10 Found: 72.83 7.37 7.14 Mass spectrum: m/e=394

EXAMPLE 39

2-n-Butyl-1-[4-[(1-carboxy-2-cyclohexyl)ethoxy]benzyl]benzimidazole

Prepared analogously to Example 1b from 2-n-butyl-1-[4-[(1-methoxycarbonyl-2 -cyclohexyl)ethoxy]benzyl]-benzimidazole and 1N sodium hydroxide solution in ethanol.

Yield: 82.0% of theory, Melting point: 165°–170° C. $C_{27}H_{34}N_2O_3$ (434.58) Calculated: C 74.63 H 7.88 N 6.44 Found: 74.46 7.77 6.30 Mass spectrum: m/e=434

EXAMPLE 40

2-n-Butyl-6-propionylamino-1-[4-[(1-carboxy-3-methyl)butyloxy]benzyl]benzimidazole Prepared analogously to Example 1b from 2-n-butyl-6-propionylamino-1-[4-[(1 -methoxycarbonyl-3-methyl)butyloxy]benzyl]benzimidazole and 1N sodium hydroxide solution in ethanol.

Yield: 80.3% of theory, Melting point: 120°–130° C. $C_{27}H_{35}N_3O_4$ (465.59) Calculated: C 69.65 H 7.58 N 9.02 Found: 69.30 7.84 8.83 Mass spectrum: m/e=465

EXAMPLE 41

2-n-Butyl-5-propionylamino-1-[4-[(1-carboxy-3-methyl)-butyloxy]benzyl]benzimidazole-semihydrate Prepared analogously to Example 1b from 2-n-butyl-5-propionylamino-1-[4-[(1 -methoxycarbonyl-3-methyl)butyloxy]benzyl]benzimidazole and 1N sodium hydroxide solution in ethanol.

Yield: 82.9% of theory, Melting point: 165°–170° C. $C_{27}H_{35}N_3O_4 \times 0.5\ H_2O$ (474.60) Calculated: C 68.32 H 7.64 N 8.85 Found: 68.63 7.72 8.90

EXAMPLE 42

2-n-Butyl-6-cyclohexylaminocarbonylamino-1-[4-[(1-carboxy-3-methyl)butyloxy]benzyl]benzimidazole Prepared analogously to Example 1b from 2-n-butyl-6-cyclohexylaminocarbonylamino-1-[4-[(1 -methoxycarbonyl-3-methyl)butyloxy]benzyl]benzimidazole and 1N sodium hydroxide solution in ethanol.

Yield: 90.8% of theory, Melting point: 155°–160° C. $C_{31}H_{42}N_4O_4$ (534.71) Calculated: C 69.64 H 7.92 N 10.48 Found: 69.58 8.03 10.36 Mass spectrum: $(M+H)^+=535$

EXAMPLE 43

2-n-Butyl-5-cyclohexylaminocarbonylamino-1-[4-[(1-carboxy-3-methyl)butyloxy]benzyl]benzimidazole Prepared analogously to Example 1b from 2-n-butyl-5-cyclohexylaminocarbonylamino-1-[4 -[(1-methoxycarbonyl-3-methyl)butyloxy]benzyl]benzimidazole and 1N sodium hydroxide solution in ethanol.

Yield: 95.7% of theory, Melting point: 220°–225° C. $C_{31}H_{42}N_4O_4$ (534.71) Calculated: C 69.64 H 7.92 N 10.48 Found: 69.49 7.99 10.52 Mass spectrum: $(M+H)^+=535$

EXAMPLE 44

2-n-Butyl-6-(N-propionyl-methylamino)-1-[4-[(1-carboxy-3-methyl)butyloxy]benzyl]benzimidazole Prepared analogously to Example 1b from 2-n-butyl-6-(N-propionylmethylamino)-1-[4-[(1 -methoxycarbonyl-3-methyl)butyloxy]benzyl]benzimidazole and 1N sodium hydroxide solution in ethanol.

Yield: 66.8% of theory, Melting point: 170°–175° C. $C_{28}H_{37}N_3O_4$ (479.63) Calculated: C 70.12 H 7.78 N 8.76 Found: 70.35 7.85 8.91

EXAMPLE 45

2-n-Butyl-5-(N-propionyl-methylamino)-1-[4-[(1-carboxy-3-methyl)butyloxy]benzyl]benzimidazole Prepared analogously to Example 1b from 2-n-butyl-5-(N-propionylmethylamino)-1-[4-[(1 -methoxycarbonyl-3-methyl)butyloxy]benzyl]benzimidazole and 1N sodium hydroxide solution in ethanol.

Yield: 62.0% of theory, Melting point: 172°–175° C. $C_{28}H_{37}N_3O_4$ (479.63) Calculated: C 70.12 H 7.78 N 8.76 Found: 70.11 7.80 8.63 Mass spectrum: m/e=479

EXAMPLE 46

2-n-Butyl-6-(N-cyclohexylaminocarbonyl-methylamino)-1-[4-[(1-carboxy-3 -methyl)butyloxy]benzyl]benzimidazole Prepared analogously to Example 1b from 2-n-butyl-6-(N-cyclohexylaminocarbonyl-methylamino)-1-[4 -[(1-methoxycarbonyl-3-methyl)butyloxy]benzyl]benzimidazole and 1N sodium hydroxide solution in ethanol.

Yield: 76.1% of theory, Melting point: 170°–175° C. $C_{32}H_{44}N_4O_4$ (548.73) Calculated: C 70.04 H 8.08 N 10.21 Found: 69.95 8.10 10.22

EXAMPLE 47

2-n-Butyl-5-(N-cyclohexylaminocarbonyl-methylamino)-1-[4-[(1-carboxy-3 -methyl)butyloxy]benzyl]benzimidazole Prepared analogously to Example 1b from 2-n-butyl-5-(N-cyclohexylaminocarbonyl-methylamino)-1-[4 -[(1-methoxycarbonyl-3-methyl)butyloxy]benzyl]benzimidazole and 1N sodium hydroxide solution in ethanol.

Yield: 72.9% of theory, Melting point: 178°–182° C. $C_{32}H_{44}N_4O_4$ (548.73) Calculated: C 70.04 H 8.08 N 10.21 Found: 69.77 7.97 10.04 Mass spectrum: m/e=548

EXAMPLE 48

2-n-Butyl-3-[4-[(α-carboxy)benzyloxy]benzyl]-5-methyl-6 -dimethylaminocarbonylamino-imidazo[4,5-b]pyridine Prepared analogously to Example 1b from 2-n-butyl-3-[4-[(α-ethoxycarbonyl)benzyloxy]benzyl]-5 -methyl-6-dimethylaminocarbonylamino-imidazo[4,5-b]pyridine and 2N sodium hydroxide solution in ethanol.

Yield: 80.0% of theory, Melting point: 191°–193° C. $C_{29}H_{33}N_5O_4$ (515.62) Calculated: C 67.55 H 6.45 N 13.58 Found: 67.49 6.62 13.57

EXAMPLE 49

2-n-Butyl-3-[4-[(α-carboxy)benzyloxy]benzyl]-5-methyl-6-(3-benzyl-3,4,5,6 -tetrahydro-2(1H)-pyrimidinon-1-yl)imidazo[4,5-b] pyridine Prepared analogously to Example 1b from 2-n-butyl-3-[4-[(α-ethoxycarbonyl)benzyloxy]benzyl]-5 -methyl-6-(3-benzyl-3,4,5,6-tetrahydro-2(1H)-pyrimidinon-1-yl)-imidazo[4,5 -b]pyridine and 2N sodium hydroxide solution in ethanol.

Yield: 87.5% of theory, Melting point: 157°–160° C. $C_{37}H_{39}N_5O_4$ (617.75) Calculated: C 71.94 H 6.36 N 11.34 Found: 71.71 6.36 10.96

EXAMPLE 50

2-n-Butyl-6-(N-methylaminocarbonyl-n-pentylamino)-1-[4-[(α-carboxy)benzyloxy]benzyl]benzimidazole Prepared analogously to Example 1b from 2-n-butyl-6-(N-methylaminocarbonyl-n-pentylamino)-1-[4 -[(α-methoxycarbonyl)benzyloxy]benzyl]benzimidazole and 1N sodium hydroxide solution in ethanol.

Yield: 76.0% of theory, Melting point: 170°–172° C. $C_{33}H_{40}N_4O_4$ (556.71) Calculated: C 71.20 H 7.24 N 10.07 Found: 70.80 7.34 9.96

EXAMPLE 51

2-n-Butyl-6-(N-cyclohexylaminocarbonyl-n-pentylamino)-1-[4-[(α-carboxy)benzyloxy]benzyl] benzimidazole Prepared analogously to Example 1b from 2-n-butyl-6-(N-cyclohexylaminocarbonyl-n-pentylamino)-1 -[4-[(α-methoxycarbonyl)benzyloxy]benzyl]benzimidazole and 1N sodium hydroxide solution in ethanol.

Yield: 65.0% of theory, Melting point: 83° C. $C_{38}H_{48}N_4O_4$ (624.83) Calculated: C 73.05 H 7.74 N 8.97 Found: 72.80 7.51 8.59

EXAMPLE 52

2-n-Butyl-4-hydroxymethyl-5-chloro-1-[4-[(α-carboxy-α-phenyl)benzyloxy]benzyl] benzimidazole Prepared analogously to Example 1b from 2-n-butyl-4-hydroxymethyl-5-chloro-1-[4 -[(α-methoxycarbonyl-α-phenyl)benzyloxy]benzyl]benzimidazole and 1N sodium hydroxide solution in ethanol.

Yield: 50.0% of theory, Melting point: 165° C. (decomp.) $C_{29}H_{29}ClN_2O_4$ (505.02) Calculated: C 68.97 H 5.79 N 5.55 Found: 68.50 5.72 5.51

EXAMPLE 53

2-n-Butyl-6-(p-methyl-phenylsulphonylamino)-1-[4-[(α-carboxy)benzyloxy]benzyl]benzimidazole Prepared analogously to Example 1b from 2-n-butyl-6-(p-methyl-phenylsulphonylamino)-1-[4 -[(α-methoxycarbonyl)benzyloxy]benzyl]benzimidazole and 1N sodium hydroxide solution in ethanol.

Yield: 81.0% of theory, Melting point: 150° C. $C_{33}H_{33}N_3O_5S$ (583.71) Calculated: C 67.90 H 5.70 N 7.20 Found: 67.18 5.70 6.96

EXAMPLE 54

2-n-Butyl-6-(N-methyl-p-methyl-phenylsulphonylamino)-1-[4-[(α-carboxy) benzyloxy]benzyl]benzimidazole Prepared analogously to Example 1b from 2-n-butyl-6-(N-methyl-p-methyl-phenylsulphonylamino)-1-[4 -[(α-methoxycarbonyl)benzyloxy]benzyl]benzimidazole and 1N sodium hydroxide solution in ethanol.

Yield: 96.0% of theory, Melting point: 218° C. $C_{34}H_{35}N_3O_5S$ (597.71) Calculated: C 68.32 H 5.90 N 7.03 Found: 67.82 5.84 6.85

EXAMPLE 55

2-n-Butyl-6-(N-n-pentyl-p-methyl-phenylsulphonylamino)-1-[4-[(α-carboxy)benzyloxy] benzyl]benzimidazole Prepared analogously to Example 1b from 2-n-butyl-6-(N-n-pentyl-p-methyl-phenylsulphonylamino)-1-[4 -[(α-methoxycarbonyl)benzyloxy]benzyl]benzimidazole and 1N sodium hydroxide solution in ethanol.

Yield: 94.0% of theory, Melting point: 202° C. C$_{38}$H$_{43}$N$_3$O$_5$S (653.81) Calculated: C 69.80 H 6.63 N 6.43 Found: 69.47 6.57 6.64

EXAMPLE 56

2-n-Butyl-1-[4-[(α-carboxy)benzyloxy]-(α-methyl)-benzyl]benzimidazole a) 4-[(α-Ethoxycarbonyl)benzyloxy]acetophenone Prepared analogously to Example 1a from ethyl 2-bromophenylacetate and 4-hydroxyacetophenone.

Yield: 78.0% of theory, R$_f$ value: 0.58 (silica gel; eluant: toluene/ethyl acetate=85:15)

b) 1-[4-[(α-Ethoxycarbonyl) benzyloxy]phenyl]ethanol 2.3 g (7.7 mMol) of 4-[(α-ethoxycarbonyl)benzyloxy]-acetophenone are dissolved in 50 ml of ethanol and at ambient temperature 0.28 g (7.7 mMol) of sodium borohydride are added thereto in batches. The reaction mixture is stirred at 40° C. for 2 hours. After cooling to ambient temperature it is concentrated by evaporation and the residue is mixed with water and dilute hydrochloric acid. After extraction with ethyl acetate the organic phase is dried with sodium sulphate. The solution is evaporated down and the residue is chromatographed over a silica gel column (particle size: 0.063–0.02 mm) using toluene/ethyl acetate (7:3). The uniform fractions are combined and evaporated down.

Yield: 1.0 g (43% of theory), Oil, R$_f$ value: 0.50 (silica gel; eluant: toluene/ethyl acetate=7:3)

c) 1-[4-[(α-Ethoxycarbonyl)benzyloxy]phenyl]-1-methanesulphonyloxyethane 0.5 g (1.7 mMol) of 1-[4-[(α-ethoxycarbonyl)benzyloxy] phenyl]ethanol and 0.22 g (2.2 mMol) of triethylamine are dissolved in 10 ml of methylene chloride. At 5° C., 0.23 g (2.0 mMol) of mesyl chloride are added dropwise with stirring. After one hour at ambient temperature the reaction mixture is poured onto ice water, extracted with methylene chloride and dried over sodium sulphate. The crude product obtained is reacted directly without any further purification.

d) 2-n-Butyl-1-[4-[(α-ethoxycarbonyl)benzyloxy]-(α-methyl)benzyl]benzimidazole

A mixture of 0.26 g (1.5 mMol) of 2-n-butyl-benzimidazole, 3 ml (1.7 mMol) of triethylamine and 1-[4-[(α-ethoxycarbonyl)benzyloxy]phenyl]-1-methanesulphonyloxyethane (crude) is heated to 80° C. for 30 minutes. After cooling, water is added and the mixture is extracted twice with ethyl acetate. The organic phases are combined, dried and evaporated down. The crude product is chromatographed over a silica gel column (particle size: 0.063–0.02 mm) with toluene/ethyl acetate (8:2). The uniform fractions are combined and evaporated down.

Yield: 0.10 g (15% of theory), R$_f$ value: 0.35 (silica gel; eluant: toluene/ethyl acetate=8:2)

e) 2-n-Butyl-1-[4-[(α-carboxy) benzyloxy]-(α-methyl)- benzyl]benzimidazole

Prepared analogously to Example 1b from 2-n-butyl-1-[4-[(α-ethoxycarbonyl)benzyloxy]-(α-methyl)benzyl]-benzimidazole and 1N sodium hydroxide solution in ethanol.

Yield: 82% of theory, Melting point: 109° C. C$_{27}$H$_{28}$N$_2$O$_3$ (428.51) Calculated: C 75.67 H 6.59 N 6.54 Found: 75.93 6.76 6.32

EXAMPLE 57

2-n-Butyl-1-[4-[α-(1H-tetrazol-5-yl)benzyloxy] benzyl]-6-(3-benzyl-3,4,5,6 -tetrahydro-2(1H)pyrimidinon-1-yl)-benzimidazole a) 5-Benzyl-1H-tetrazole Prepared from benzylcyanide and sodium azide/ammonium chloride in dimethylformamide.

Yield: 70% of theory, Melting point: 130°–132° C.

b) N-Triphenylmethyl-5-benzyl-tetrazole

Prepared from 5-benzyl-1H-tetrazole and triphenylmethyl-chloride.

Yield: 84% of theory, Melting point: 158°–160° C.

c) N-Triphenylmethyl-5-(α-bromo)benzyl-tetrazole 2.0 g (5 mMol) of N-triphenylmethyl-5-benzyl-tetrazole, 0.89 g (5 mMol) of N-bromosuccinimide and 30 mg of azo-bisisobutyronitrile are dissolved in 25 ml of carbon tetrachloride and heated to boiling for one hour under UV-irradiation. After cooling, the succinimide formed is filtered off and the filtrate is evaporated down.

Yield: 74.6% of theory, Melting point: 160°–162° C.

d) 2-n-Butyl-1-[(4-benzyloxy)benzyl]-6-(3-benzyl-3,4,5,6-tetrahydro-2(1 H)pyrimidinon-1-yl)-benzimidazole Prepared analogously to Example 1a from 2-n-butyl-6-(3-benzyl3,4,5,6-tetrahydro-2 (1H)pyrimidinon-1-yl)-benzimidazole and 4-benzyloxybenzyl chloride.

Yield: 65.5% of theory, R$_f$ value: 0.45 (silica gel; eluant: methylene chloride/ethanol=19:1)

e) 2-n-Butyl-1-[(4-hydroxy)benzyl]-6-(3-benzyl-3,4,5,6-tetrahydro-2(1 H)pyrimidinon-1-yl)-benzimidazole 2.4 g of 2-n-butyl-1-[(4-benzyloxy)benzyl]-6-(3-benzyl-3,4,5,6-tetrahydro-2(1 H)pyrimidinon-1-yl)-benzimidazole are dissolved in 100 ml of ethanol and 30 ml of dimethylformamide, mixed with 2.4 g of (10%) palladium on activated charcoal and hydrogenated with 5 bars of hydrogen at ambient temperature. The catalyst is filtered off, the filtrate is evaporated down and the residue is chromatographed over a silica gel column (particle size: 0.063–0.02 mm) with methylene chloride/ethanol. The uniform fractions are combined and evaporated down and the residue is triturated with ether and suction filtered.

Yield: 1.1 g (55% of theory), Melting point: 190°–191° C.

f) 2-n-Butyl-1-[4-[(α-(N-triphenylmethyl)tetrazol-5-yl)-benzyloxy]benzyl]-6 -(3-benzyl-3,4,5,6-tetrahydro-2(1H) pyrimidinon-1-yl) -benzimidazole 0.5 g (1.1 mMol) of 2-n-butyl-1-[(4-hydroxy)benzyl]-6-(3-benzyl-3,4,5,6 -tetrahydro-2(1H) pyrimidinon-1-yl) -benzimidazole, 0.74 g (5.4 mMol) of potassium carbonate and 0.93 g (1.1 mMol) of N-triphenylmethyl-5 -[(α-bromo)- benzyl]tetrazole are dissolved in 10 ml of dimethylsulphoxide and stirred for 2 hours at ambient temperature. The product is precipitated by the addition of saline solution, suction filtered, washed with water and dried.

Yield: 0.9 g (97% of theory), Melting point: from 150° C. (decomp.)

g) 2-n-Butyl-1-[4-[α-(1H-tetrazol-5-yl)benzyloxy]-benzyl]-6-(3-benzyl-3,4,5,6-tetrahydro-2(1H)-pyrimidin-1-yl)-benzimidazole 0.9 g (1.0 mMol) of 2-n-butyl-1-[4-[(α-N-triphenyl-methyl)tetrazol-5 -yl)benzyloxy]benzyl]-6-(3-benzyl-3,4,5,6-tetrahydro-2(1H)pyrimidinon-1 -yl)-benzimidazole are dissolved in 40 ml of ethanol, 10 ml of methylene chloride and 12 ml of 4N hydrochloric acid and stirred for 2 hours at ambient temperature. After the addition of 30 ml of water, the mixture is extracted with methylene chloride. The organic phase is washed with 1N sodium hydroxide solution, acidified with dilute acetic acid and dried over sodium sulphate. The crude product is chromatographed over a silica gel column (particle size: 0.063–0.02 mm) with methylene chloride/ethanol (50:1 and 19:1). The unified fractions are combined and evaporated down.

Yield: 0.22 g (34% of theory), Melting point: from 134° C. (decomp.) $C_{37}H_{38}N_8O_2$ (626.76) Calculated: C 70.90 H 6.11 N 17.88 Found: 70.72 6.00 17.68

EXAMPLE 58

2-n-Propyl-4-methyl-1-[4-[α-(1H-tetrazol-5-yl)benzyloxy]benzyl]benzimidazole a) 2-n-Propyl-4-methyl-1-[4-[α-((N-triphenylmethyl)-tetrazol-5-yl)benzyloxy]benzyl]benzimidazole Prepared analogously to Example 57f from 2-n-propyl-4-methyl-1-[(4-hydroxy)benzyl]benzimidazole and N-triphenylmethyl-5-[(α-bromo)benzyl]tetrazole.

Yield: 99% of theory, $R_f$ value: 0.68 (silica gel; eluant: methylene chloride/methanol=19:1)

b) 2-n-Propyl-4-methyl-1-[4-[α-(1H-tetrazol-5-yl)-benzyloxy]benzyl]benzimidazole Prepared analogously to Example 57g from 2-n-propyl-4-methyl-1-[4 -[α-((N-triphenylmethyl)tetrazol-5-yl)-benzyloxy]benzyl]benzimidazole and methanolic hydrochloric acid.

Yield: 63% of theory, Melting point: amorphous $C_{26}H_{26}N_6O$ (438.54) Calculated: C 71.21 H 5.98 N 19.17 Found: 70.99 5.98 18.96

EXAMPLE 59

2-n-Propyl-4-methyl-6-(1-methyl-benzimidazol-2-yl)-1-[4-[α-(1H-tetrazol-5 -yl)benzyloxy]benzyl]benzimidazole a) 2-n-Propyl-4-methyl-6-(1-methyl-benzimidazol-2-yl)- 1-[4 -[α-((N-triphenylmethyl)tetrazol-5-yl)benzyloxy]-benzyl]benzimidazole Prepared analogously to Example 57f from 2-n-propyl-4-methyl-6-1-benzimidazol-2-yl)-1 -[(4-hydroxy)-benzyl]benzimidazole (synthesised analogously to Examples 58d and 58e) and N-triphenylmethyl-5-(α-bromo)-benzyl-tetrazole.

Yield: 94% of theory, $R_f$ value : 0.70 (silica gel; eluant: methylene chloride/methanol=9:1)

2-n-Propyl-4-methyl-6-(1-methyl-benzimidazol-2-yl)-1-[4-[α-(1H-tetrazol-5 -yl)benzyloxy]benzyl-benzimidazole Prepared analogously to Example 57g from 2-n-propyl-4-methyl-6-(1-methyl-benzimidazol-2 -yl)-1-[4-[α-((N-triphenylmethyl)-tetrazol-5-yl)benzyloxy]benzyl]-benzimidazole and methanolic hydrochloric acid.

Yield: 62% of theory, Melting point: 165°–166° C. $C_{34}H_{32}N_8O$ (568.69) Calculated: C 71.81 H 5.67 N 19.71 Found: 71.68 5.60 19.55

EXAMPLE 60

2-n-Propyl-5-n-butyrylamino-3-[4-[(1-(1H-tetrazol-5-yl)-3 -methyl)butyloxy]benzyl]imidazo[4,5-b]pyridine a) 2-n-Propyl-5-n-butyrylamino-3-[4-[(1-cyano-3-methyl)-butyloxy]benzyl]imidazo[4,5 -b]pyridine Prepared analogously to Example 57f from 2-n-propyl-5-n-butyrylamino-3-[(4 -hydroxy)benzyl]imidazo[4,5-b]-pyridine and 2-bromo-4-methyl-valeronitrile.

Yield: 85% of theory, $R_f$ value: 0.40 (silica gel; eluant: ethyl acetate/petroleum ether=1:1)

b) 2-n-Propyl-5-n-butyrylamino-3-[4-[(1-(1H-tetrazol-5-yl)-3 -methyl)butyloxy]benzyl]imidazo[4,5-b]pyridine A mixture of 800 mg (1.78 mMol) of 2-n-propyl-5-n-butyrylamino-3-[4-[(1-cyano-3 -methyl)butyloxy)benzyl]-imidazo[4,5-b]pyridine, 2.2 g (3.3 mMol) of sodium azide and 1.8 g (3.3 mMol) of ammonium chloride in 8 ml of dimethylformamide is stirred for 5 hours at 130° C. with stirring. It is then stirred into ice water, the product precipitated is suction filtered, washed with water, dried and purified over a silica gel column (methylene chloride/ethanol=19:1). The fractions containing the desired substance are evaporated down, the residue obtained is triturated with ether, suction filtered and dried. When the purification step described above is repeated, 370 mg (42% of theory) of the product are obtained, m.p. 175°–177° C.

$C_{26}H_{34}N_8O_2$ (490.61) Calculated: C 63.65 H 6.99 N 22.84 Found: 63.61 7.03 22.83

EXAMPLE 61

2-n-Butyl-4-hydroxymethyl-5-chloro-1-[4-[1-(1H-tetrazol-5 -yl)propyloxy]benzyl]benzimidazole sesqui-hydrochloride Prepared analogously to Example 60b from 2-n-butyl-4-hydroxymethyl-5-chloro-1-[4 -(1-cyano-propyloxy)benzyl] -imidazole and sodium azide/ammonium chloride in dimethylformamide.

Yield: 78% of theory, Oil, $C_{19}H_{25}ClN_6O_2 \times 1.5$ HCl (459.59) Calculated: C 49.65 H 5.81 18.28 Found: 49.41 6.03 18.52

EXAMPLE 62

2-n-Butyl-5-hydroxymethyl-4-chloro-1-[4-[1-(1H-tetrazol-5 -yl)propyloxy]benzyl]benzimidazole sesqui-hydrochloride Prepared analogously to Example 60b from 2-n-butyl-5-hydroxymethyl-4-chloro-1-[4 -(1-cyano-propyloxy)benzyl]-imidazole and sodium azide/ammonium chloride in dimethylformamide.

Yield: 70% of theory, Oil, $C_{19}H_{25}ClN_6O_2 \times 1.5$ HCl (459.59) Calculated: C 49.65 H 5.81 N 18.28 Found: 49.86 5.76 18.26

EXAMPLE 63

2-n-Butyl-1-[4-[(α-carboxy)benzylamino]benzyl]-benzimidazole semihydrate a) 2-n-Butyl-1-[4-[(α-ethoxycarbonyl)benzylamino]- benzyl]benzimidazole 1.0 g (3.6 mMol) of 2-n-butyl-1-[(4-amino)benzyl]-benzimidazole, 0.87 g (3.6 mMol) of ethyl 2-bromo-phenylacetate and 0.5 g of sodium acetate-trihydrate are dissolved in 20 ml of ethanol and stirred for 18 hours at ambient temperature. Then the reaction mixture is refluxed for a further 4 hours. The solvent is evaporated down, water is added to the residue which is made alkaline with dilute ammonia solution and extracted with ethyl acetate. The combined organic phases are washed with water, dried over magnesium sulphate and concentrated by evaporation. The residue is purified over a silica gel column (particle size: 0.063–0.02 mm), using petroleum ether with 10–15% ethyl acetate as eluant. The uniform fractions are combined and evaporated down.

Yield: 1.0 g (63% of theory), $R_f$ value: 0.53 (silica gel; eluant: petroleum ether/ethyl acetate=3:1)

b) 2-n-Butyl-1-[4-[(α-carboxy)benzylamino]benzyl]- benzimidazole semihydrate Prepared analogously to Example 1b from 2-n-butyl-1-[4 -[(α-ethoxycarbonyl)benzylamino]benzyl]benzimidazole and 1N sodium hydroxide solution in ethanol.

Yield: 99% of theory, $C_{26}H_{27}N_3O_2 \times 0.5$ $H_2O$ (422.54) Calculated: C 73.91 H 6.68 N 9.95 Found: 74.05 6.55 9.91

EXAMPLE 64

2-n-Butyl-1-[4-[(α-carboxy)-N-acetyl-benzylamino] benzyl]benzimidazole a) 2-n-Butyl-1-[4-[(α-ethoxycarbonyl)-N-acetyl-benzylamino]benzyl]benzimidazole 0.5 g (1.1 mMol) of 2-n-butyl-1-[4-[(α-ethoxycarbonyl-)benzylamino]benzyl]benzimidazole are dissolved in 5 ml of aceticanhydride and stirred at 120° C. for 3 hours. The solvent is eliminated, the residue is purified over a silica gel column (particle size: 0.063–0.02 mm), using ethyl acetate as eluant. The uniform fractions are combined and evaporated down.

Yield: 0.35 g (64% of theory), $R_f$ value: 0.50 (silica gel; eluant: methylene chloride/ethanol=95:5)

b) 2-n-Butyl-1-[4-[(α-carboxy)-N-acetyl-benzylamino]- benzyl]benzimidazole

Prepared analogously to Example 1b from 2-n-butyl-1-[4 -[(α-ethoxycarbonyl)-N-acetyl-benzylamino]benzyl]-benzimidazole and 1N sodium hydroxide solution in ethanol.

Yield: 74% of theory, Melting point: 212°–214° C. $C_{28}H_{29}N_3O_3$ (455.56) Calculated: C 73.82 H 6.42 N 9.12 Found: 73.50 6.58 9.28

EXAMPLE 65

2-n-Butyl-1-[4-[(2-carboxy-3-phenyl)propyl] benzyl]-benzimidazole a) 2-n-Butyl-1-[(4-hydroxymethyl) benzyl]benzimidazole 1.2 g (30 mMol) of lithium aluminium hydride are suspended in 200 ml of absolute tetrahydrofuran. At ambient temperature a solution of 10.6 g (30 mMol) of 2-n-butyl-1-[(4-ethoxycarbonyl)benzyl] benzimidazole in 100 ml of absolute tetrahydrofuran is added dropwise. The mixture is stirred for 2 hours at ambient temperature and then slowly hydrolysed, with cooling, with aqueous sodium hydroxide solution. The crystallised salts are suction filtered and the filtrate is concentrated by evaporation. The residue is mixed with water and extracted with ethyl acetate. The combined organic phases are washed with water, dried and concentrated by evaporation. The residue is purified over a silica gel column (particle size: 0.063–0.02 mm), using methylene chloride/methanol (30:1) as eluant. The uniform fractions are combined and evaporated down.

Yield: 6.5 g (74% of theory), $R_f$ value: 0.60 (silica gel; eluant: methylene chloride/methanol=19:1)

b) 2-n-Butyl-1-[(4-chloromethyl) benzyl]benzimidazole 6.2 g (21 mMol) of 2-n-butyl-1-[(4-hydroxymethyl)benzyl]benzimidazole are dissolved in 10 ml of thionylchloride and refluxed for 10 minutes. Then the excess thionylchloride is distilled off and the residue is mixed with ice water. After neutralisation with saturated sodium hydrogen carbonate solution, the mixture is extracted with ethyl acetate. The combined organic phases are washed with water, dried and evaporated down.

Yield: 6.0 g (91% of theory), $R_f$ value: 0.65 (silica gel; eluant: methylene chloride/methanol=19:1)

c) 2-n-Butyl-1-[4-[(2,2-bis-ethoxycarbonyl-3-phenyl)-propyl]benzyl]benzimidazole 2.4 g (9.6 mMol) of diethyl benzylmalonate are dissolved in 25 ml of dimethylsulphoxide, mixed with 1.1 g (9.6 mMol) of potassium tert.butoxide and stirred for 30 minutes at ambient temperature. Then a solution of 3.0 g (9.6 mMol) of 2-n-butyl-1-[(4-chloromethyl)-benzyl]benzimidazole in 25 ml of dimethylsulphoxide is added dropwise. After one hour at ambient temperature the mixture is heated to 100° C. for 15 minutes. The reaction mixture is combined with ice water. The product which crystallises out is suction filtered and extracted with ethyl acetate. The combined organic phases are washed with water, dried and evaporated down.

Yield: 4.2 g (83% of theory), $R_f$ value: 0.15 (silica gel; eluant: methylene chloride/methanol=30:1)

d) 2-n-Butyl-1-[4-[(2-carboxy-3-phenyl)propyl]benzyl]-benzimidazole 0.44 g (0.8 mMol) of 2-n-butyl-1-[4-[(2,2-bis-ethoxycarbonyl-3-phenyl)propyl]benzyl]benzimidazole and 0.12 g of sodium hydroxide are taken up in 30 ml of water and refluxed for 8 hours. The mixture is then acidified with glacial acetic acid. The product which crystallises out is suction filtered and purified over a silica gel column (particle size: 0.063–0.02 mm), using methylene chloride/methanol (19:1) as eluant. The uniform fractions are combined, evaporated down, triturated with ether, suction filtered and dried.

Yield: 0.1 g (39% of theory), Melting point: 139°–140° C. $C_{28}H_{30}N_2O_2$ (426.56) Calculated: C 78.84 H 7.09 N 6.57 Found: 78.72 6.96 6.56

EXAMPLE 66

2-n-Butyl-1-[4-[(2-carboxy-2-phenyl)ethyl]benzyl]-benzimidazole a) 2-n-Butyl-1-[4-[(2,2-bis-ethoxycarbonyl-2-phenyl)-ethyl]benzyl]benzimidazole Prepared analogously to Example 65c from 2-n-butyl-1-[(4-chloromethyl)benzyl]benzimidazole and diethylphenylmalonate/potassium tert.butoxide.

Yield: 82% of theory, $R_f$ value: 0.20 (silica gel; eluant: methylene chloride/methanol=40:1)

b) 2-n-Butyl-1-[4-[(2-carboxy-2-phenyl)ethyl]-benzyl] benzimidazole

Prepared analogously to Example 65d from 2-n-butyl-1-[4-[(2,2-bis-ethoxycarbonyl-2-phenyl)ethyl]benzyl]-benzimidazole and aqueous sodium hydroxide solution in ethanol.

Yield: 37% of theory, Melting point: 171°–172° C. $C_{27}H_{28}N_2O_2$ (412.54) Calculated: C 78.44 H 6.66 N 6.88 Found: 78.61 6.84 6.79

EXAMPLE 67

2-n-Propyl-5-(N-ethyl-cyclohexylcarbonylamino)-3-[4-[(α-carboxy)benzyloxy]benzyl]imidazo[4,5-b]pyridine Prepared analogously to Example 1b from 2-n-propyl-5-(N-ethylcyclohexylcarbonylamino)-3-[4-[(α-ethoxycarbonyl)-benzyl]imidazo[4,5-b]pyridine and 1N sodium hydroxide solution in ethanol.

Yield: 87% of theory, Melting point: 113°–115° C. $C_{33}H_{38}N_4O_4$ (554.70) Calculated: C 71.46 H 6.91 N 10.10 Found: 71.60 6.99 10.00

EXAMPLE 68

2-n-Propyl-5-(N-cyclohexylaminocarbonyl-ethylamino)-3-[4-[(α-carboxy)benzyloxy]benzyl]imidazo[4,5-b]pyridine Prepared analogously to Example 1b from 2-n-propyl-5-(N-cyclohexylaminocarbonyl-ethylamino)-3-[4-[(α-ethoxycarbonyl)benzyloxy]benzyl]benzimidazole and 1N sodium hydroxide solution in ethanol.

Yield: 20% of theory, Melting point: 183° C. $C_{33}H_{39}N_5O_4$ (569.72) Calculated: C 69.57 H 6.90 N 12.29 Found: 69.80 6.69 11.97

EXAMPLE 69

2-n-Butyl-4-methyl-7-[α-(1H-tetrazol-5-yl)benzyloxy]-1-[4-[α-(1H-tetrazol-5-yl)benzyloxy]benzyl]benzimidazole Prepared analogously to Example 57g from 2-n-butyl-4-methyl-7-[α-(1-triphenylmethyl-tetrazol-5-yl)benzyloxy]-1-[4-[α-((1-triphenylmethyl)tetrazol-5-yl)benzyloxy]-benzyl]benzimidazole and 4N hydrochloric acid.

Yield: 52% of theory, Melting point: from 166° C. (decomp.) $C_{35}H_{34}N_{10}O_2$ (626.72) Calculated: C 67.68 H 5.46 N 22.35 Found: 67.70 5.52 22.66

EXAMPLE 70

2-n-Butyl-5-methyl-6-(3-benzyl-3,4,5,6-tetrahydro-2(1H)-pyrimidinon-1-yl)-3-[4-[α-(1H-tetrazol-5-yl)benzyloxy]benzyl]imidazo[4,5-b]pyridine Prepared analogously to Example 57g from 2-n-butyl-5-methyl-6-(3-benzyl-3,4,5,6-tetrahydro-2(1H)pyrimidinon-1-yl)-3-[4-[α-((1-triphenylmethyl)tetrazol-5-yl) benzyloxy]benzyl]imidazo[4,5-b]pyridine and 4N hydrochloric acid.

Yield: 75% of theory, Melting point: 185°–187° C. $C_{37}H_{39}N_9O_2$ (661.79) Calculated: C 69.24 H 6.12 N 19.64 Found: 68.97 6.17 19.91

EXAMPLE 71

2-n-Butyl-5-dimethylaminocarbonylamino-1-[4-[α-(1H-tetrazol-5-yl)benzyloxy]benzyl]benzimidazole Prepared analogously to Example 57g from 2-n-butyl-5-dimethylaminocarbonylamino-1-[4-[α-((1-triphenylmethyl)-tetrazol-5-yl)benzyloxy]benzyl]benzimidazole and 4N hydrochloric acid.

Yield: 66% of theory, Melting point: 207°–209° C. $C_{29}H_{32}N_8O_2$ (524.68) Calculated: C 64.19 H 6.31 N 20.65 Found: 63.95 6.33 20.44

EXAMPLE 72

2-Ethyl-5,7-dimethyl-3-[4-[α-(1H-tetrazol-5-yl)benzyloxy]benzyl]imidazo[4,5-b]pyridine semihydrate Prepared analogously to Example 57g from 2-ethyl-5,7-dimethyl-3-[4-[α-((1-triphenylmethyl)tetrazol-5-yl)benzyloxy]benzyl]imidazo[4,5-b]pyridine-semihydrate and 4N hydrochloric acid.

Yield: 83% of theory, Melting point: 104°–105° C. $C_{25}H_{25}N_7O \times 0.5\ H_2O$ (448.53) Calculated: C 66.95 H 5.89 N 21.83 Found: 67.05 5.94 22.36

EXAMPLE 73

2-n-Propyl-4-methyl-1-[4-[α-(O-ethyl-phosphono)benzylamino]benzyl]benzimidazole hydrate a) 2-n-Propyl-4-methyl-1-[4-[α-(O,O-diethyl-phosphono)-benzylamino]benzyl]benzimidazole 6.5 g (23.3 mMol) of 2-n-propyl-4-methyl-1-[(4-amino)benzyl]benzimidazole are stirred into 4.2 g (40 mMol) of benzaldehyde. The mixture is stirred at ambient temperature for 2 hours. Then 10.72 g (77.6 mMol) of diethylphosphite are added and the mixture is heated to 100° C. for 45 minutes. The precipitate formed after cooling to ambient temperature is triturated with 250 ml of ether, suction filtered and dried in air. It is then recrystallised from 150 ml of petroleum ether/isopropanol (2:1).

Yield: 8.7 g (74% of theory), Melting point: 110°–115° C.

b) 2-n-Propyl-4-methyl-1-[4-[α-(O-ethyl-phosphono)-benzylamino]benzyl]benzimidazole hydrate 0.5 g (1 mMol) of 2-n-propyl-4-methyl-1-[4 -[α-(O,O-diethylphosphono)benzylamino]benzyl]benzimidazole and 1.0 g of pulverised potassium hydroxide are dissolved in 20 ml of methanol and refluxed for 9 hours. After cooling to ambient temperature, 25 ml of ice water are added. The pH is adjusted to 6.5 by the addition of glacial acetic acid and conc. ammonia solution. After the addition of solid sodium chloride, extraction is carried out six times, each time using 100 ml of ethyl acetate. The combined organic phases are washed with saturated saline solution and dried over magnesium sulphate. After evaporation of the solvent in vacuo the residue is triturated with ether and dried over potassium hydroxide.

Yield: 0.35 g (73% of theory), Melting point: from 158° C. (decomp.) $C_{27}H_{32}N_3O_3P \times H_2O$ (495.57) Calculated: C 65.44 H 6.92 N 8.48 Found: 65.66 6.52 8.49

EXAMPLE 74

2-n-Butyl-1-[4-[α-(O-ethyl-phosphono)benzylamino]benzyl]benzimidazole a) 2-n-Butyl-1-[4-[α-(O,O-diethyl-phosphono)-benzylamino]benzyl]benzimidazole Prepared analogously to Example 73a from 2-n-butyl-1-[(4-amino)benzyl]benzimidazole, benzaldehyde and diethylphosphite.

Yield: 51% of theory, Melting point: 149°–153° C.

b) 2-n-Butyl-1-[4-[α-(O-ethyl-phosphono)benzylamino]benzyl]benzimidazole

Prepared analogously to Example 73b from 2-n-butyl-1-[4 -[α-(O,O-diethyl-phosphono)benzylamino]benzyl]-benzimidazole and methanolic potassium hydroxide solution.

Yield: 67% of theory, Melting point: 118°–123° C. (decomp.) $C_{27}H_{32}N_3O_3P$ (477.55) Calculated: C 67.91 H 6.76 N 8.80 Found: 67.74 7.02 8.64

EXAMPLE 75

2-n-Butyl-1-[4-[(α-carboxy)benzyloxy]benzyl]-benzimidazole a) 2-n-Butyl-1-[4-[(α-ethoxycarbonyl)benzyloxy]-benzyl]benzimidazole

Prepared analogously to Example 1a from 2-n-butyl-benzimidazole and 4-[(α-ethoxycarbonylbenzyloxy)-benzyl]bromide.

Yield: 22.0% of theory, Oil, $R_f$ value: 0.65 (silica gel; eluant: ethyl acetate/ethanol=9:1) $C_{28}H_{30}N_2O_3$ (442.60) Calculated: C 75.99 H 6.83 N 6.33 Found: 75.97 6.79 5.99 b) 2-n-Butyl-1-[4-[(α-carboxy)benzyloxy]benzyl]-benzimidazole

Prepared analogously to Example 1b from 2-n-butyl-1-[4-[(α-ethoxycarbonyl)benzyloxy]benzyl]benzimidazole and 1N sodium hydroxide solution in ethanol.

Yield: 38.0% of theory, Melting point: 223°–225° C. $C_{26}H_{26}N_2O_3$ (414.51) Calculated: C 75.34 H 6.32 N 6.76 Found: 75.03 6.34 6.73

EXAMPLE 76

2-n-Propyl-7-methyl-3-[4-[(α-carboxy)benzyloxy]benzyl]-imidazo[4,5-b]pyridine a) 2-n-Propyl-7-methyl-3-[4-[(α-ethoxycarbonyl)-benzyloxy]benzyl]imidazo[4,5-b]pyridine Prepared analogously to Example 1a from 2-n-propyl-7-methylimidazo[4,5-b]pyridine and 4-[(α-ethoxycarbonyl)-benzylbromide.

Yield: 34.0% of theory, Oil, $R_f$ value: 0.40 (silica gel; eluant: methylene chloride/ethanol=25:1)

b) 2-n-Propyl-7-methyl-3-[4-[(α-carboxy)benzyloxy]benzyl]imidazo[4,5-b]pyridine Prepared analogously to Example 1b from 2-n-propyl-7-methyl-3-[4 -[(α-ethoxycarbonyl)benzyloxy]benzyl]-imidazo[4,5-b]pyridine and 1N sodium hydroxide solution in ethanol.

Yield: 66.4% of theory, Melting point: 108° C. $C_{25}H_{25}N_3O_3$ (415.50) Calculated: C 72.27 H 6.06 N 10.11 Found: 72.25 6.03 9.87

EXAMPLE 77

5,7-Dimethyl-2-ethyl-3-[4-[(α-carboxy)benzyloxy]benzyl]imidazo[4,5-b]pyridine semihydrate Prepared analogously to Example 1b from 5,7-dimethyl-2-ethyl-3 -[4-[(α-ethoxycarbonyl)benzyloxy]benzyl]-imidazo[4,5-b]pyridine and 1N sodium hydroxide solution in ethanol.

Yield: 89.3% of theory, Melting point: 251°–253° C. $C_{25}H_{25}N_3O_3 \times 0.5 H_2O$ (424.50) Calculated: C 70.73 H 6.17 N 9.89 Found: 71.00 5.97 9.79

EXAMPLE 78

2-n-Butyl-1-[4-[(α-carboxy)benzyloxy]-3,5-dichloro-benzyl]-6-cyclohexylaminocarbonylamino-benzimidazole Prepared analogously to Example 1b from 2-n-butyl-1-[4-[(α-ethoxycarbonyl)benzyloxy]-3,5 -dichlorobenzyl]-6-cyclohexylaminocarbonylamino-benzimidazole and 1N sodium hydroxide solution in ethanol.

Yield: 95.6% of theory, Melting point: 251°–253° C. $C_{33}H_{36}Cl_2N_4O_4$ (623.58) Calculated: C 63.56 H 5.82 N 8.98 $Cl$ 11.37 Found: 63.39 5.88 8.87 11.85

EXAMPLE 79

2-n-Butyl-1-[4-[(α-carboxy)benzyloxy]-3-methoxybenzyl]-6-dimethylaminocarbonylamino-benzimidazole Prepared analogously to Example 1b from 2-n-butyl-1-[4-[(α-ethoxycarbonyl)benzyloxy]-3 -methoxybenzyl]-6-dimethylaminocarbonylamino-benzimidazole and 2N sodium hydroxide solution in ethanol.

Yield: 87.5% of theory, Melting point: 170°–172° C. $C_{30}H_{34}N_4O_5$ (530.62) Calculated: C 67.90 H 6.46 N 10.56 Found: 67.64 6.25 10.33

EXAMPLE 80

2-n-Butyl-1-[4-[(α-carboxy)benzyloxy]-3-methoxybenzyl]-5-dimethylaminocarbonylamino-benzimidazole Prepared analogously to Example 1b from 2-n-butyl-1-[4-[(α-ethoxycarbonyl)benzyloxy]-3 -methoxybenzyl]-5-dimethylaminocarbonylamino-benzimidazole and 2N sodium hydroxide solution in ethanol.

Yield: 78.6% of theory, Melting point: 154°–156° C. $C_{30}H_{34}N_4O_5$ (530.62) Calculated: C 67.90 H 6.46 N 10.56 Found: 67.74 6.37 10.24

EXAMPLE 81

2-n-Propyl-1-[4-[(α-carboxy)benzyloxy]-3,5-dimethoxybenzyl]-6-(1 -methyl-benzimidazol-2-yl)-4-methyl-benzimidazole hydrate Prepared analogously to Example 1b from 2-n-propyl-1-[4 -[(α-ethoxycarbonyl)benzyloxy]-3,5-dimethoxybenzyl]-6-(1-methylbenzimidazol-2-yl)-4 -methyl-benzimidazole and 2N sodium hydroxide solution in ethanol.

Yield: 91.4% of theory, Melting point: 148°–150° C. $C_{36}H_{36}N_4O_5 \times H_2O$ (622.72) Calculated: C 69.44 H 6.25 N 9.00 Found: 69.77 6.09 8.92

EXAMPLE 82

2-n-Propyl-1-[4-[(α-carboxy)benzyloxy]-3,5-dibromobenzyl]-6-(1-methyl-benzimidazol-2 -yl)-4-methyl-benzimidazole hydrate Prepared analogously to Example 1b from 2-n-propyl-1-[4-[(α-ethoxycarbonyl)benzyloxy]-3,5 -dibromobenzyl]-6-(1-methyl-benzimidazol-2-yl)-4-methyl-benzimidazole and 2N sodium hydroxide solution in ethanol.

Yield: 58.4% of theory, Melting point: 229°–230° C. $C_{34}H_{30}Br2N_4O_3 \times H_2O$ (720.46) Calculated: C 56.68 H 4.47 N 7.77 Found: 56.78 4.64 7.75

EXAMPLE 83

2-n-Propyl-6-(2,3-dimethylsuccinimino)-1-[4-[(α-carboxy)benzyloxy]-3,5 -dimethoxybenzyl]-benzimidazole semihydrate Prepared analogously to Example 1b from 2-n-propyl-6-(2,3-dimethylsuccinimino)-1-[4 -[(α-ethoxycarbonyl)-benzyloxy]-3,5-dimethoxybenzyl]-benzimidazole and 2N sodium hydroxide solution in ethanol.

Yield: 13.8% of theory, Melting point: 129°–131° C. $C_{34}H_{37}N_3O_7 \times 0.5\ H_2O$ (608.69) Calculated: C 67.09 H 6.29 N 6.90 Found: 67.29 6.37 6.86

EXAMPLE 84

2-n-Butyl-6-(1-cyclohexen-1,2-dicarbonylimino)-1-[4 -[(α-carboxy)benzyloxy]benzyl]benzimidazole semihydrate Prepared analogously to Example 1b from 2-n-butyl-6-(1-cyclohexen-1,2-dicarbonylimino)-1 -[4-[(α-ethoxycarbonyl)benzyloxy]benzyl]benzimidazole and 1N sodium hydroxide solution in ethanol.

Yield: 23.3% of theory, Melting point: 247°–249° C. $C_{34}H_{33}N_3O_5 \times 0.5\ H_2O$ (572.66) Calculated: C 71.30 H 5.98 N 7.33 Found: 71.47 6.05 7.15

EXAMPLE 85

2-n-Propyl-4-methyl-1-[4-[(α-carboxy)-2-chlorobenzyloxy]benzyl]benzimidazole

Prepared analogously to Example 1b from 2-n-propyl-4-methyl-1-[4-[(α-ethoxycarbonyl)-2 -chlorobenzyloxy]-benzyl]benzimidazole and 2N sodium hydroxide solution in ethanol.

Yield: 40.7% of theory, Melting point: sinters from 105° C. $C_{26}H_{25}ClN_2O_3$ (448.97) Calculated: C 70.00 H 5.62 N 6.28 Cl 7.91 Found: 69.94 5.72 6.29 7.92

EXAMPLE 86

2-n-Propyl-4-chloro-6-(1-oxo-2-isoindolin-2-yl)-1-[4 -[(α-carboxy)benzyloxy]benzyl]benzimidazole Prepared analogously to Example 1b from 2-n-propyl-4-chloro-6-(1-oxo-2 -isoindolin-2-yl)-1-[4-[(α-ethoxycarbonyl)benzyloxy]benzyl]benzimidazole and 2N sodium hydroxide solution in ethanol.

Yield: 61.0% of theory, Melting point: 252°–254° C. $C_{33}H_{28}ClN_3O_4$ (566.06) Calculated: C 70.00 H 5.02 N 7.42 Cl 6.25 Found: 69.81 5.22 7.87 6.54

EXAMPLE 87

2-n-Butyl-6-(1-cyclohexen-1,2-dicarbonylimino)-1-[4-[α-(1H-tetrazol-5 -yl)benzyloxy]benzyl]benzimidazole Prepared analogously to Example 57g from 2-n-butyl-6-(1-cyclohexen-1,2-dicarbonylimino)-1 -[4-[(α-(N-triphenylmethyl)tetrazol-5-yl)benzyloxy]benzyl]-benzimidazole and 85% formic acid in methylene chloride.

Yield: 43.7% of theory, Melting point: 149°–151° C. $C_{34}H_{33}N_7O_3$ (587.68) Calculated: C 69.49 H 5.66 N 16.68 Found: 69.40 5.83 16.31

EXAMPLE 88

2-n-Butyl-5-methyl-6-dimethylaminocarbonylamino-3-[4-[α-(1H-tetrazol-5 -yl)benzyloxy]benzyl]imidazol[4,5-b]-pyridine Prepared analogously to Example 57g from 2-n-butyl-5-methyl-6-dimethylaminocarbonylamino-3-[4 -[(α-(N-triphenylmethyl)tetrazol-5-yl)benzyloxy]benzyl]imidazo-[4,5-b] pyridine and 4N hydrochloric acid in ethanol.

Yield: 75% of theory, Melting point: 198°–200° C. $C_{29}H_{33}N_9O_2$ (539.64) Calculated: C 64.54 H 6.16 N 23.36 Found: 64.37 6.24 23.57

EXAMPLE 89

2-n-Butyl-6-(cyclohexylaminocarbonyl-N-methylamino)-1-[4-[α-(1H-tetrazol-5 -yl)benzyloxy]benzyl]benzimidazole Prepared analogously to Example 57g from 2-n-butyl-6-(cyclohexylaminocarbonyl-N-methylamino)-1 -[4-[(α-(N-triphenylmethyl)-tetrazol-5-yl)benzyloxy]benzyl]-benzimidazole and 4N hydrochloric acid in ethanol.

Yield: 85.7% of theory, Melting point: 195°–197° C. $C_{34}H_{40}N_8O_2$ (592.74) Calculated: C 68.89 H 6.80 N 18.90 Found: 68.82 6.91 18.77

EXAMPLE 90

5,7-Dimethyl-2-ethyl-3-[4-[α-(1H-tetrazol-5-yl)-benzyloxy]-3,5 -dichlorobenzyl]imidazo[4,5-b]pyridine hydrate Prepared analogously to Example 57g from 5,7-dimethyl-2-ethyl-3-[4 -[(α-(N-triphenylmethyl)tetrazol-5-yl)benzyloxy]-3,5-dichlorobenzyl]imidazo[4,5-b]pyridine and 85% formic acid in methylene chloride.

Yield: 77.2% of theory, Melting point: 143°–145° C. $C_{25}H_{23}Cl_2N_7O \times H_2O$ (526.42) Calculated: C 57.04 H 4.78 N 18.62 Cl 13.47 Found: 57.51 4.82 19.03 13.38

EXAMPLE 91

2-n-Butyl-6-cyclohexylaminocarbonylamino-1-[4-[α-(1H-tetrazol-5-yl)benzyloxy]-3,5 -dichlorobenzyl]-benzimidazole semihydrate Prepared analogously to Example 57g from 2-n-butyl-6-cyclohexylaminocarbonylamino-1-[4 -[(α-(N-triphenyl-methyl)tetrazol-5-yl)benzyloxy]-3,5-dichlorobenzyl]-benzimidazole and 85% formic acid in methylene chloride.

Yield: 83% of theory, Melting point: 129°–131° C. $C_{33}H_{36}Cl_2N_8O_2 \times 0.5\ H_2O$ (655.62) Calculated: C 60.36 H 5.68 N 17.07 Found: 60.40 5.78 17.19

EXAMPLE 92

2-n-Butyl-6-dimethylaminocarbonylamino-1-[4-[α-(1H-tetrazol-5-yl)benzyloxy]-3 -methoxybenzyl]benzimidazole Prepared analogously to Example 57g from 2-n-butyl-6-dimethylaminocarbonylamino-1-[4 -[(α-(N-triphenylmethyl)-tetrazol-5-yl)benzyloxy]-3-methoxybenzyl]benzimidazole and 4N hydrochloric acid in ethanol.

Yield: 75% of theory, Melting point: 158°–162° C. $C_{30}H_{34}N_8O_3$ (554.65) Calculated: C 64.97 H 6.18 N 20.20 Found: 64.71 6.20 19.91

EXAMPLE 93

2-n-Propyl-4-methyl-6-(1-methyl-benzimidazol-2-yl)-1-[4-[α-(1H-tetrazol-5 -yl)benzyloxy]-3,5-dimethoxybenzyl]-benzimidazole hydrate Prepared analogously to Example 57g from 2-n-propyl-4-methyl-6-(1-methyl-benzimidazol-2 -yl)-1-[4-[(α-(N-triphenylmethyl)tetrazol-5-yl)benzyloxy]-3,5-dimethoxy-benzyl]benzimidazole and 85% formic acid in methylene chloride.

Yield: 83% of theory, Melting point: 152°–154° C. $C_{36}H_{36}N_8O_3 \times H_2O$ (646.75) Calculated: C 66.86 H 5.97 N 17.33 Found: 67.08 5.99 16.97

EXAMPLE 94

2-n-Propyl-4-methyl-6-(2,3-dimethylsuccinimino)-1-[4-[α-(1H-tetrazol-5 -yl)benzyloxy]-3,5-dimethoxybenzyl]-benzimidazole semihydrate Prepared analogously to Example 57g from 2-n-propyl-4-methyl-6-(2,3-dimethylsuccinimino) -1-[4 -[(α-(N-triphenylmethyl) tetrazol-5-yl)benzyloxy]-3,5-dimethoxybenzyl] benzimidazole and 85% formic acid in methylene chloride.

Yield: 74.6% of theory, Melting point: 192°–144 ° C. $C_{34}H_{37}N_7O_5 \times 0.5\ H_2O$ (632.71) Calculated: C 64.54 H 6.05 N 15.50 Found: 64.46 6.10 15.25

EXAMPLE 95

2-n-Propyl-4-methyl-6-(1-methyl-benzimidazol-2-yl)-1-[4-[α-(1H-tetrazol-5 -yl)benzyloxy]-3,5-dibromobenzyl]-benzimidazole Prepared analogously to Example 57g from 2-n-propyl-4-methyl-6(1-methyl-benzimidazol-2 -yl)-1-[4-[(α-(N-triphenylmethyl)tetrazol-5-yl)benzyloxy]-3,5dibromobenzyl]benzimidazole and 85% formic acid in methylene chloride.

Yield: 21.6% of theory, Melting point: 132°–134° C. $C_{34}H_{30}Br_2N_8O$ (726.47) Calculated: C 56.21 H 4.16 N 15.42 Br 21.99 Found: 56.53 4.50 15.42 22.03

EXAMPLE 96

2-n-Butyl-5-dimethylaminocarbonylamino-1-[4-[α-(1H-tetrazol-5-yl)benzyloxy]-3 -methoxybenzyl]-benzimidazole Prepared analogously to Example 57g from 2-n-butyl-5-dimethylaminocarbonylamino-1-[4 -[(α-(N-triphenylmethyl)-tetrazol-5-yl)benzyloxy]-3-methoxybenzyl]benzimidazole and 4N hydrochloric acid in ethanol.

Yield: 88.2% of theory, Melting point: 181°–185° C. $C_{30}H_{34}N_8O_3$ (554.66) Calculated: C 64.96 H 6.18 N 20.20 Found: 65.18 5.92 19.97

EXAMPLE 97

5,7-Dimethyl-2-ethyl-3-[4-[α-(O-ethyl-phosphono) benzyloxy]benzyl]imidazo[4,5 -b]pyridine sodium salt-semihydrate Prepared analogously to Example 73b from 5,7-dimethyl-2-ethyl-3-3[4 -[α-(O,O-diethylphosphono)benzyloxy]benzyl]imidazo[4,5-b]pyridine and potassium hydroxide in methanol.

Yield: 52% of theory, Melting point: from 150° C. (decomp.) $C_{26}H_{30}N_4NaO_3P\times0.5$ $H_2O$ (509.52) Calculated: C 61.29 H 6.33 N 11.00 Found: 60.95 6.34 10.98

EXAMPLE 98

2-n-Propyl-4-methyl-1-[4-[α-(O-ethyl-phosphono)-N-methylbenzylamino]benzyl]benzimidazole semihydrate a)
2-n-Propyl-4-methyl-1-[4-[α-(O,O-diethylphosphono)-N-methyl-benzylamino]benzyl]benzimidazole 1.1 g (2 mMol) of 2-n-propyl-4-methyl-1-[4 -[α-(O,O-diethylphosphono)-benzylamino]benzyl]benzimidazole are dissolved in 1 ml of formic acid and mixed with 2 ml of a 37% formalin solution. The mixture is stirred for 2 hours at 100° C., cooled and poured onto ice. After the addition of conc. ammonia the mixture is extracted twice with ethyl acetate. The combined organic phases are washed with saturated saline solution and dried over magnesium sulphate. The organic phase is evaporated down in vacuo and the residue obtained is purified over a silica gel column (particle size: 0.063–0.02 mm, ethyl acetate/petroleum ether=1:1 to 1:2). The uniform fractions are combined and evaporated down in vacuo.

Yield: 0.60 g (58% of theory), $R_f$ value: 0.45 (silica gel; eluant: petroleum ether/ethyl acetate=1:1)

b) 2-n-Propyl-4-methyl-1-[4 -[α-(O-ethyl-phosphono)-N-methyl-benzylamino] benzyl]benzimidazole semihydrate Prepared analogously to Example 73b from 2-n-propyl-4-methyl-1-[4 -[α-(O,O-diethylphosphono)-N-methylbenzylamino]benzyl]benzimidazole and potassium hydroxide in methanol.

Yield: 77% of theory, Melting point: from 106° C. (decomp.) $C_{28}H_{34}N_3O_3P\times0.5$ $H_2O$ (500.59) Calculated: C 67.18 H 7.05 N 8.40 Found: 67.25 7.02 8.42

EXAMPLE 99

2-n-Propyl-4-methyl-1-[4-[α-(O-ethyl-phosphono) benzylamino]benzyl]benzimidazole hydrobromide 0.5 g (1.0 mMol) of 2-n-propyl-4-methyl-1-[4 -[α-(O,O-diethylphosphono)benzylamino]benzyl]benzimidazole are dissolved in 10 ml of 48% hydrobromic acid and refluxed for 5 hours. After cooling at ambient temperature, the pH is adjusted to 6 by the addition of concentrated ammonia and glacial acetic acid. The precipitate formed is suction filtered and dried over potassium hydroxide at 40° C.

Yield: 47% of theory, Melting point: from 140° C. (decomp.) $C_{25}H_{28}N_3O_3P\times HBr$ (530.42) Calculated: C 56.61 H 5.51 N 7.92 Found: 56.48 5.80 8.05

EXAMPLE 100

2-n-Propyl-4-methyl-1-[4-[(α-methanesulphonylaminocarbonyl)benzyloxy]benzyl] benzimidazole 410 mg (1 mMol) of 2-n-propyl-4-methyl-1-[4-[(α-carboxy)benzyloxy]benzyl]benzimidazole are dissolved in 100 ml of thionylchloride, mixed with 1 drop of dimethylformamide and refluxed for 1 hour. Then, after the addition of toluene, the mixture is evaporated to dryness and taken up in 30 ml of acetone. After the addition of 1 ml of triethylamine and 150 mg (1.58 mMol) of methanesulphonic acid amide the mixture is stirred for 2 hours at ambient temperature. The reaction mixture is then evaporated down and the residue is purified over a silica gel column (particle size: 0.063–0.02 mm; methylene chloride/ethanol=50:1, 19:1, 9:1 and 4:1). The uniform fractions are combined, evaporated down and the residue obtained is triturated with ether and dried.

Yield: 15.3% of theory, Melting point: 139°–141° C. $C_{27}N_{29}N_3O_4S$ (491.60) Calculated: C 65.95 H 5.94 N 8.54 Found: 65.67 6.27 8.89

EXAMPLE 101

2-Ethyl-4-methyl-1-[4-[(α-carboxy)benzyloxy]benzyl]-6-(n-butanesultam-1-yl)benzimidazole Prepared analogously to Example 1b from 2-ethyl-4-methyl-1-[4 -[(α-ethoxycarbonyl)benzyloxy]benzyl]-6-(n-butanesultam-1-yl)benzimidazole and 2N sodium hydroxide solution in ethanol.

EXAMPLE 102

2-Ethyl-4-methyl-1-[4-[α-(1H-tetrazol-5-yl)benzyloxy]-benzyl]-6 -(n-butanesultam-1-yl)benzimidazole Prepared analogously to Example 57g from 2-ethyl-4-methyl-1-[4-[(α-(N-triphenylmethyl)tetrazol-5 -yl)-benzyloxy]benzyl]-6-(n-butanesultam-1-yl)-benzimidazole and 4N hydrochloric acid in ethanol.

EXAMPLE 103

2-n-Butyl-1-[4-[α-(ethoxycarbonyl)-α-(2-pyridyl)-methoxy]benzyl]-6 -(N-cyclohexylaminocarbonyl-methylamino)-benzimidazole Prepared analogously to Example 1a from 2-n-butyl-1-(4-hydroxybenzyl)-6 -(N-cyclohexylaminocarbonyl-methylamino)benzimidazole and ethyl α-bromo-pyridyl-2-acetate.

Yield: 90.0% of theory, $R_f$ value: 0.70 (silica gel; ethyl acetate/ethanol/ammonia=90:10:1) $C_{33}H_{44}N_5O_4$ (574.76) Calculated: C 70.20 H 7.40 N 11.69 Found: 69.97 7.26 11.21

EXAMPLE 104

2-n-Butyl-3-[4-[(α-carboxy)benzyloxy]-3-methoxybenzyl]-5-methyl-6 -dimethylaminocarbonylamino-imidazo[4,5-b]-pyridine Prepared analogously to Example 1b from 2-n-butyl-3-[4-[(α-ethoxycarbonyl)benzyloxy]-3 -methoxybenzyl]-5-methyl-6-dimethylaminocarbonylamino-imidazo[4,5-b]pyridine and 2N sodium hydroxide solution in ethanol.

Yield: 91.8% of theory, Melting point: 174°–176° C. $R_f$ value: 0.60 (silica gel; ethyl acetate/ethanol/ammonia= 50:45:5) $C_{30}H_{35}N_5O_5$ (545.65) Calculated: C 66.04 H 6.47 N 12.84 Found: 66.25 6.39 12.95

EXAMPLE 105

2-n-Butyl-1-[4-[α-(ethoxycarbonyl)-α-(2-pyridyl)meth-oxy]benzyl]-6-dimethylaminocarbonylamino-benzimidazole Prepared analogously to Example 1a from 2-n-butyl-1-(4-hydroxybenzyl)-6-dimethylaminocarbonylamino-benzimidazole and ethyl α-bromo-pyridyl-2-acetate.

Yield: 87.5% of theory, $R_f$ value: 0.50 (silica gel; ethyl acetate/ethanol/ammonia=90:10:1) $C_{30}H_{35}N_5O_4$ (529.65) Calculated: C 68.03 H 6.66 N 13.22 Found: 68.09 6.83 13.06

EXAMPLE 106

2-n-Butyl-1-[4-[α-(ethoxycarbonyl)-α-(2-pyridyl)meth-oxy]benzyl]-6-cyclohexylcarbonylamino-benzimidazole Prepared analogously to Example 1a from 2-n-butyl-1-(4-hydroxybenzyl)-6-cyclohexylcarbonylamino-benzimidazole and ethyl α-bromopyridyl-2-acetate.

Yield: 75.3% of theory, $R_f$ value: 0.50 (silica gel; ethyl acetate/ethanol/ammonia=90:10:1) $C_{34}H_{40}N_4O_4$ (568.73) Calculated: C 71.80 H 7.09 N 9.35 Found: 71.82 7.2 1 9.83

EXAMPLE 107

2-n-Butyl-3-[4-[α-(1H-tetrazol-5-yl)benzyloxy]-3-methoxybenzyl]-5-methyl-6-dimethylaminocarbonylamino-imidazo[4,5-b]pyridine Prepared analogously to Example 57g from 2-n-butyl-3-[4-[α-((N-triphenylmethyl)-tetrazol-5-yl)benzyloxy]-3-methoxybenzyl]-5-methyl-6-dimethylaminocarbonylamino-imidazo[4,5-b]pyridine and 4N hydrochloric acid in ethanol.

Yield: 60.0% of theory, Melting point: 197°–199° C. $R_f$ value: 0.60 (silica gel; ethyl acetate/ethanol/ammonia= 50:45:5) $C_{30}H_{35}N_9O_3$ (569.68) Calculated: C 63.25 H 6.19 N 22.13 Found: 62.94 6.13 21.87

EXAMPLE 108

2-n-Butyl-1-[4-[α-(1H-tetrazol-5-yl)-α-(2-pyridyl)methoxy]benzyl]-6-dimethylaminocarbonylamino-benzimidazole Prepared analogously to Example 57g from 2-n-butyl-1-[4-[α-((N-triphenylmethyl)-tetrazol-5-yl)-α-(2-pyridyl)methoxy]benzyl]-6-dimethylaminocarbonylamino-benzimidazole and 4N hydrochloric acid in ethanol.

Yield: 25.0% of theory, Melting point: 197°–203° C. $R_f$ value: 0.50 (silica gel; ethyl acetate/ethanol/ammonia= 50:45:5) $C_{28}H_{31}N_9O_2$ (525.63) Mass spectrum: (M+H)=526

EXAMPLE 109

2-Ethyl-3-[4-[α-(1H-tetrazol-5-yl)benzyloxy]benzyl]-5-methyl-6-dimethylaminocarbonylamino-imidazo[4,5-b]-pyridine Prepared analogously to Example 57g from 2-ethyl-3-[4-[α-((N-triphenylmethyl)-tetrazol-5-yl)benzyloxy]benzyl]-5-methyl-6-dimethylaminocarbonylamino-imidazo[4,5-b]-pyridine and 4N hydrochloric acid in ethanol.

Yield: 50.0% of theory, Melting point: 234°–236° C. $C_{27}H_{29}N_9O_2$ (511.60) Calculated: C 63.39 H 5.71 N 24.64 Found: 63.36 5.87 24.52

EXAMPLE 110

2-n-Butyl-4-methyl-1-[4-[α-(1H-tetrazol-5-yl)benzyloxy]-benzyl]-6-(2,3-dimethylsuccinimino)benzimidazole Prepared analogously to Example 57g from 2-n-butyl-4-methyl-1-[4-[α-((N-triphenylmethyl)-tetrazol-5-yl)-benzyloxy]benzyl]-6-(2,3-dimethylsuccinimino)-benzimidazole and 4N hydrochloric acid in ethanol.

Yield: 80.0% of theory, Melting point: 175°–177° C. $C_{33}H_{35}N_7O_3$ (577.70) Calculated: C 68.61 H 6.11 N 16.97 Found: 68.45 6.24 17.00

EXAMPLE 111

2-n-Butyl-4-methyl-1-[4-[(α-carboxy)benzyloxy]benzyl]-6-cyclohexylcarbonylamino-benzimidazole Prepared analogously to Example 1b from 2-n-butyl-4-methyl-1-[4-[(α-ethoxycarbonyl)benzyloxy]benzyl]-6-cyclohexylcarbonylaminobenzimidazole and 2N sodium hydroxide solution in ethanol.

Yield: 81.8% of theory, Melting point: 191°–193° C. $C_{34}H_{39}N_3O_4$ (553.70) Calculated: C 73.75 H 7.10 N 7.58 Found: 73.70 6.94 7.48

EXAMPLE 112

2-n-Butyl-4-methyl-1-[4-[α-(1H-tetrazol-5-yl)benzyloxy]-benzyl]-6-cyclohexylcarbonylamino-benzimidazole Prepared analogously to Example 57g from 2-n-butyl-4-methyl-1-[4-[α-((N-triphenylmethyl)-tetrazol-5-yl)-benzyloxy]benzyl]-6-cyclohexylcarbonylamino-benzimidazole and 4N hydrochloric acid in ethanol.

Yield: 85.0% of theory, Melting point: 195°–198° C. $C_{34}H_{39}N_7O_2$ (577.72) Calculated: C 70.68 H 6.80 N 16.97 Found: 70.81 6.98 16.97

EXAMPLE 113

2-n-Butyl-4-methyl-1-[4-[α-(carboxy)benzyloxy]benzyl]-6-tert.butylcarbonylamino-benzimidazole Prepared analogously to Example 1b from 2-n-butyl-4-methyl-1-[4-[(α-ethoxycarbonyl)benzyloxy]benzyl]-6-tert.butylcarbonylamino-benzimidazole and 2N sodium hydroxide solution in ethanol.

Yield: 78.6% of theory, Melting point: 179°–181° C. $C_{32}H_{37}N_3O_4$ (527.67) Calculated: C 72.34 H 7.07 N 7.96 Found: 72.51 6.95 7.65

EXAMPLE 114

2-n-Butyl-4-methyl-1-[4-[α-(tetrazol-5-yl)benzyloxy]-benzyl]-6-tert.butylcarbonylamino-benzimidazole Prepared analogously to Example 57g from 2-n-butyl-4-methyl-1-[4-[∝-((N-triphenylmethyl)-tetrazol-5-yl)benzyloxy]benzyl]-6-tert.butylcarbonylamino-benzimidazole and 4N hydrochloric acid in ethanol.

Yield: 75.0% of theory, Melting point: 191°–193° C. $C_{32}H_{37}N_7O_2$ (551.70) Calculated: C 69.67 H 7.76 N 17.77 Found: 69.42 7.80 17.68

EXAMPLE 115

2-Ethoxy-7-ethoxycarbonyl-1-[4-[(α-ethoxycarbonyl)benzyloxy]benzyl]benzimidazole Prepared analogously to Example 63a from 2-ethoxy-7-ethoxycarbonyl-1-(4-hydroxy)benzyl-benzimidazole and ethyl 2-bromo-phenylacetate.

Yield: % of theory, Melting point: —°C. $R_f$ value: 0. (silica gel); $C_{29}H_{30}N_2O_6$ (488.57) Calculated: C H N Found:

EXAMPLE 116

2-Ethoxy-7-carboxy-1-[4-(α-carboxy)benzyloxy]benzyl]benzimidazole

Prepared analogously to Example 1b from 2-ethoxy-7-ethoxycarbonyl-1-[4 -[(α-ethoxycarbonyl)benzyloxy]-benzyl]benzimidazole and 2N sodium hydroxide solution in ethanol.

Yield: % of theory, Melting point: —°C. $R_f$ value: 0. (silica gel;) $C_{25}H_{22}N_2O_6$ (446.46) Calculated: C H N Found:

EXAMPLE 117

2-Ethoxy-7-ethoxycarbonyl-1-[4-[α-(1H-tetrazol-5-yl)benzyloxy]benzyl]benzimidazole Prepared analogously to Example 57g from 2-ethoxy-7-ethoxycarbonyl-1-[4 -[α-((N-triphenylmethyl)tetrazol-5-yl)benzyloxy]benzyl]benzimidazole and methanolic hydrochloric acid.

Yield: % of theory, Melting point: —°C. $R_f$ value: 0. (silica gel;) $C_{27}H_{26}N_6O_4$ (498.55) Calculated: C H N Found:

EXAMPLE 118

2-Ethoxy-7-carboxy-1-[4-[α-(1H-tetrazol-5-yl)benzyloxy]benzyl]benzimidazole

Prepared analogously to Example 1b from 2-ethoxy-7-ethoxycarbonyl-1-[4-[α-(1 H-tetrazol-5-yl)benzyloxy]benzyl]benzimidazole and 2N sodium hydroxide solution in ethanol.

Yield: % of theory, Melting point: —°C. $R_f$ value: 0. (silica gel;) $C_{25}H_{22}N_6O_4$ (470.49) Calculated: C H N Found:

In the Examples of pharmaceutical Formulations which follow, any suitable compound of formula I, particularly compounds A to I of the pharmacological test report, may be used as the active substance:

EXAMPLE I

Ampoules containing 50 mg of active substance per 5 ml

| Active substance | 50 mg |
|---|---|
| $KH_2PO_4$ | 2 mg |
| $Na_2HPO_4 \times 2H_2O$ | 50 mg |
| NaCl | 12 mg |
| Water for injections ad | 5 ml |

Preparation:

The buffer substances and isotonic substance are dissolved in some of the water. The active substance is added and, once it has been completely dissolved, water is added to make up the required volume.

EXAMPLE II

Ampoules containing 100 mg of active substance per 5 ml

| Active substance | 100 mg |
|---|---|
| Methyl glucamine | 35 mg |
| Glycofurol | 1000 mg |
| Polyethyleneglycol-polypropyleneglycol block polymer | 250 mg |
| Water for injections ad | 5 ml |

Preparation:

Methyl glucamine is dissolved in some of the water and the active substance is dissolved with stirring and heating. After the addition of solvents, water is added to make up the desired volume.

EXAMPLE III

Tablets containing 50 mg of active substance

| Active substance | 50.0 mg |
|---|---|
| Calcium phosphate | 70.0 mg |
| Lactose | 40.0 mg |
| Corn starch | 35.0 mg |
| Polyvinylpyrrolidone | 3.5 mg |
| Magnesium stearate | 1.5 mg |
| | 200.0 mg |

Preparation:

The active substance, $CaHPO_4$, lactose and corn starch are uniformly moistened with an aqueous PVP solution. The mass is passed through a 2 mm screen, dried at 50° C. in a circulating air dryer and screened again.

After the lubricant has been added, the granules are compressed in a tablet making machine.

EXAMPLE IV

Coated tablets containing 50 mg of active substance

| Active substance | 50.0 mg |
|---|---|
| Lysine | 25.0 mg |
| Lactose | 60.0 mg |
| Corn starch | 34.0 mg |
| Gelatin | 10.0 mg |
| Magnesium stearate | 1.0 mg |
| | 180.0 mg |

Preparation:

The active substance is mixed with the excipients and moistened with an aqueous gelatin solution. After screening and drying the granules are mixed with magnesium stearate and compressed to form tablet cores.

The cores thus produced are covered with a coating by known methods. A colouring may be added to the coating suspension or solution.

EXAMPLE V

Coated tablets containing 100 mg of active substance

| Active substance | 100.0 mg |
|---|---|
| Lysine | 50.0 mg |
| Lactose | 86.0 mg |
| Corn starch | 50.0 mg |
| Polyvinylpyrrolidone | 2.8 mg |
| Microcrystalline cellulose | 60.0 mg |
| Magnesium stearate | 1.2 mg |
| | 350.0 mg |

Preparation:

The active substance is mixed with the excipients and moistened with an aqueous PVP solution. The moist mass is passed through a 1.5 mm screen and dried at 45° C. After drying, it is screened again and the magnesium stearate is added. This mixture is compressed into cores.

The cores thus produced are covered with a coating by known methods. Colourings may be added to the coating suspension or solution.

EXAMPLE VI

Capsules containing 250 mg of active substance

| Active substance | 250.0 mg |
|---|---|
| Corn starch | 68.5 mg |
| Magnesium stearate | 1.5 mg |
| | 320.0 mg |

Preparation:

The active substance and corn starch are mixed together and moistened with water. The moist mass is screened and dried. The dry granules are screened and mixed with magnesium stearate. The final mixture is packed into size 1 hard gelatine capsules.

EXAMPLE VII

Oral suspension containing 50 mg of active substance per 5 ml

| Active substance | 50.0 mg |
|---|---|
| Hydroxyethylcellulose | 50.0 mg |
| Sorbic acid | 5.0 mg |
| 70% sorbitol | 600.0 mg |
| Glycerol | 200.0 mg |
| Flavouring | 15.0 mg |
| Water ad | 5.0 ml |

Preparation:

Distilled water is heated to 70° C. Hydroxyethyl-cellulose is dissolved therein with stirring. By the addition of sorbitol solution and glycerol the mixture is cooled to ambient temperature. At ambient temperature, sorbic acid, flavouring and active substance are added. The suspension is evacuated with stirring to remove any air. One dose of 50 mg is contained in 5.0 ml.

EXAMPLE VIII

Suppositories containing 100 mg of active substance

| Active substance | 100.0 mg |
|---|---|
| Solid fat | 1600.0 mg |
| (adeps solidus) | 1700.0 mg |

Preparation:

The hard fat is melted. At 40° C. the ground active substance is homogeneously dispersed in the melt. It is cooled to 38° C. and poured into slightly chilled suppository moulds.

What is claimed is:

1. 2-n-Propyl-6-(1-methyl-benzimidazol-2-yl)-4-methyl-1-[4 -[($\alpha$-carboxy)benzyoxy]benzyl]benzimidazole or the pharmaceutically acceptable salts thereof.

2. 2-n-Propyl-4-methyl-6-(1-methyl-benzimidazol-2-yl)-4-methyl-1-[4 -[($\alpha$-1H-tetrazol-5-yl)benzyoxy]benzyl]benzimidazole or the pharmaceutically acceptable salts thereof.

3. A phenylalkyl compound of formula (Ia)

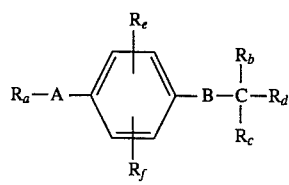

wherein

A is selected from the group consisting of a methylene group, ethylene group or a ethylidene group, B is selected from the group consisting of an oxygen atom, a methylene group, imino group, methylamino group or an acetylimino group, $R_a$ is a group of the formula (II)

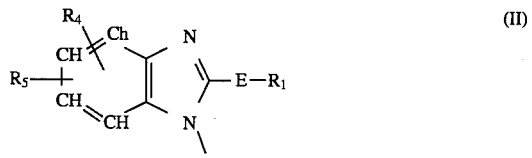

wherein

E is an oxygen atom or a carbon-carbon bond, $R_1$ is a straight or branched $C_{1-6}$-alkyl group, $R_4$ is a hydrogen atom or a $C_{1-3}$-alkyl group and $R_5$ is selected from the group consisting of a hydrogen atom, fluorine atom, chlorine atom, bromine atom, a straight-chained or branched $C_{1-3}$-alkyl group, an $\alpha$-(1H-tetrazol-5-yl)-benzyloxy group, an amino group, a nitro group, a carboxy group, an alkoxycarbonyl group with a total of 2 to 4 carbon atoms, an acylamino group or an acylamino substituted at the nitrogen atom by a $C_{1-5}$ alkyl group, wherein each acyl moiety is selected from the group consisting of a $C_{1-5}$-alkanoyl group, a benzenesulphonyl group, a benzene sulphonyl group mono- or di-substituted by a methyl or methoxy group wherein the substituents are identical or different, a 5-, 6- or 7-membered alkyleneimino group or a 5-, 6- or 7-membered akyleneimino group substituted by one or two methyl groups wherein a methylene group of each alkyleneimino moiety can be replaced by a group selected from a carbonyl group or a sulphonyl group, a 2,3-dimethylsuccinimido group, a phthalimino group, a homophthalimino group, an isoindolin-1-on-yl group, or a benzimidazol-2-yl group, a benzimidazol-2-yl group substituted in the 1-position by a $C_{1-3}$-alkyl group, an $R_{11}$—$NR_{10}$—CO—$NR_9$ group, wherein $R_9$ is selected from a hydrogen atom, a $C_{1-5}$-alkyl group, or a phenylalkyl group, $R_{10}$ is selected from a hydrogen atom, a $C_{1-5}$-alkyl group, and a cyclohexyl group, $R_{11}$ is selected from a hydrogen atom, a benzyl group or a $C_{1-5}$-alkyl group or $R_9$ and $R_{11}$ together are $C_{2-4}$-alkylene group, and $R_{10}$ is defined hereinabove, $R_b$ is selected from a carboxyl group, 1H-tetrazolyl group, ($C_{1-3}$-alkyl-O)phosphono group, and ($C_{1-3}$-alkyl)sulphonylaminocarbonyl group, $R_c$ is a hydrogen atom or a phenyl group, $R_d$ is selected from a straight-chained or branched $C_{1-4}$-alkyl group, a cyclohexyl group, a cyclohexylmethyl group, a phenyl group, a biphenyl group, a methoxyphenyl group, a chlorophenyl group, a pyridyl group, and a naphthyl group, $R_e$ and $R_f$ are hydrogen atoms with the proviso that where $R_5$ is selected from a benzimidazol-2-yl group, a benzimidazol-2-yl group substituted in the 1-position by a $C_{1-3}$-alkyl group, a 2,3-dimethylsuccinimo group or a 5-, 6- or 7-membered alkyleneimino group, or a 5-, 6- or 7-membered alkyleneimino group substituted by one or two methyl groups wherein a methylene group of each akyleneimino moiety can additionally be replaced by a group selected from a carbonyl group or a sulphonyl group, and an $R_{11}$—$NR_{10}$—CO—$NR_9$ group, wherein $R_9$ to $R_{11}$ are defined hereinabove, then Re is selected from a hydrogen atom, chlorine atom, bromine atom, a methoxy group, and $R_f$ is selected from a chlorine atom, bromine atom and a methoxy group, the isomer mixtures thereof, the tautomers, enantiomers or pharmaceutically acceptable salts thereof.

4. The phenylalkyl compound as recited in claim 3, wherein

A is selected from a methylene group, ethylene group, and ethylidene group,

B is selected from an oxygen atom, a methylene group, imino group, methylimino group, and acetylimino group, $R_a$ is a group of the Formula II

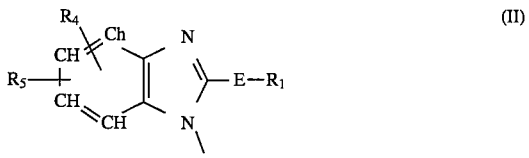

wherein

E is an oxygen atom or a carbon-carbon bond $R_1$ is straight-chained or branched $C_{1-6}$-alkyl group, $R_4$ is a hydrogen atom or a $C_{1-3}$-alkyl group, and $R_5$ is a benzimidazol-2-yl group or a benzimidazol-2-yl group substituted in the 1-position by a $C_{1-3}$-alkyl group, $R_b$ is selected from a carboxyl group, 1H-tetrazolyl group, ($C_{1-3}$-alkyl-O)phosphono group, and ($C_{1-3}$-alkyl)sulphonylaminocarbonyl group, $R_c$ is a hydrogen atom or a phenyl group, $R_d$ is selected from a straight-chained or branched $C_{1-4}$-alkyl group, a cyclohexyl group, a cyclohexylmethyl group, a phenyl group, a biphenyl group, a methoxyphenyl group, a chlorophenyl group, a pyridyl group, or naphthyl group, $R_e$ is selected from a hydrogen atom, chlorine atom, bromine atom, or a methoxy group, and $R_f$ is selected from a hydrogen atom, chlorine atom, bromine atom, or a methoxy group, the isomer mixtures thereof, the tautomers, enantiomers or pharmaceutically acceptable salts thereof.

5. The phenylalkyl compound as recited in claim 3, wherein

A is a methylene group,

B is an oxygen atom, $R_a$ is a group of the formula II,

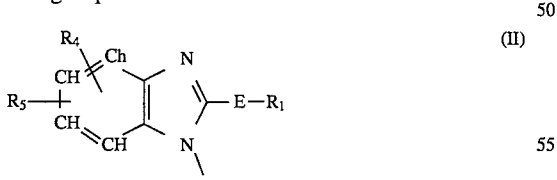

wherein

E is an oxygen atom or a carbon-carbon bond $R_1$ is straight-chained or branched $C_{1-6}$-alkyl group, $R_4$ is a hydrogen atom or a $C_{1-3}$-alkyl group, and $R_5$ is a benzimidazol-2-yl group or a benzimidazol-2-yl group substituted in the 1-position by a $C_{1-3}$-alkyl group, $R_b$ is a carboxyl group or a 1H-tetrazolyl group, $R_c$ is a hydrogen atom, $R_d$ is a phenyl group, $R_e$ is a hydrogen atom, and $R_f$ is a hydrogen atom, the isomer mixtures thereof, the tautomers, enantiomers or pharmaceutically acceptable salts thereof.

6. A phenylalkyl derivative as recited in claim 3 selected from the group consisting of:

(a) 2-n-propyl-4-methyl-1-[4-[(α-carboxy)benzyloxy]benzyl]benzimidazole, (b) 2-n-butyl-1-[4-[(α-carboxy)benzyloxy]benzyl]-6-dimethylaminocarbonylamino-benzimidazole, (c) 2-n-propyl-6-(1-methyl-benzimidazol-2-yl)-4-methyl-1-[4 -[(α-carboxy)benzyloxy]benzyl]benzimidazole, (d) 2-methyl-4-[4'-[(α-carboxy)benzyloxy]benzyloxy]-quinoline, (e) 2-n-butyl-8-methyl-3-[4-[(α-carboxy)benzyloxy]-benzyl]-quinazolin-4-one semihydrate, (f) 2-n-propyl-4-methyl-6-(1-methyl-benzimidazol-2-yl)-1-[4-[α-(1H-tetrazol-5 -yl)benzyloxy]benzyl]-benzimidazole, (g) 2-n-butyl-6-(N-propionyl-methylamino)-1-[4-[(1-carboxy-3 -methyl)butyloxy]benzyl]benzimidazole, (h) 2-n-butyl-5-methyl-6-(3-benzyl-3,4,5,6-tetrahydro-2(1H)-pyrimidinon-1-yl)-3 -[4-[α-(1H-tetrazol-5-yl)benzyloxy]benzyl]imidazol[4,5-b]pyridine, (i) 2-n-butyl-1-[4-[α-(α-ethyl-phosphono)benzylamino]benzyl]benzimidazole, and a salt thereof with an inorganic or organic acid or base.

* * * * *